(12) United States Patent
Hixson et al.

(10) Patent No.: US 9,539,053 B2
(45) Date of Patent: Jan. 10, 2017

(54) VESSEL SEALER AND DIVIDER FOR LARGE TISSUE STRUCTURES

(71) Applicant: COVIDIEN LP, Mansfield, MA (US)

(72) Inventors: David Hixson, Longmont, CO (US); Jeremy S. James, Westminster, CO (US); Jeffrey R. Unger, Longmont, CO (US); Chelsea Shields, Portland, OR (US)

(73) Assignee: COVIDIEN LP, Mansfield, MA (US)

( * ) Notice: Subject to any disclaimer, the term of this patent is extended or adjusted under 35 U.S.C. 154(b) by 322 days.

(21) Appl. No.: 14/274,445

(22) Filed: May 9, 2014

(65) Prior Publication Data

US 2014/0249528 A1 Sep. 4, 2014

Related U.S. Application Data

(63) Continuation of application No. 12/233,951, filed on Sep. 19, 2008, now Pat. No. 8,734,443, which is a (Continued)

(51) Int. Cl.
*A61B 18/12* (2006.01)
*A61B 18/14* (2006.01)
(Continued)

(52) U.S. Cl.
CPC ............ *A61B 18/1445* (2013.01); *A61B 17/32* (2013.01); *A61B 18/1402* (2013.01);
(Continued)

(58) Field of Classification Search
CPC . A61B 17/32; A61B 18/1402; A61B 18/1442; A61B 18/1445; A61B 2017/2945; A61B 2018/00345; A61B 2018/00404; A61B 2018/00607; A61B 2018/00619; A61B 2018/0063; A61B 2018/1412; A61B 2018/1432; A61B 2018/1455; A61B 2018/1467; A61B 2018/1861
See application file for complete search history.

(56) References Cited

U.S. PATENT DOCUMENTS 371,664 A 10/1887 Brannan et al.
702,472 A 6/1902 Pignolet
(Continued)

FOREIGN PATENT DOCUMENTS

CA 2104423 A1 2/1994
DE 2415263 A1 10/1975
(Continued)

OTHER PUBLICATIONS

Int'l Search Report EP 04027705 dated Feb. 3, 2005.
(Continued)

*Primary Examiner* — Daniel Fowler

(57) ABSTRACT

An endoscopic bipolar forceps includes a housing having a shaft affixed thereto, the shaft including jaw members at a distal end thereof. The shaft includes jaw members adapted to connect to a source of electrosurgical energy such that the jaw members are capable of conducting energy through tissue held therebetween to effect a tissue seal. The forceps include a drive assembly that moves the jaw members relative to one another from a first position to a second position for manipulating tissue. A movable handle is included that is rotatable about a pivot. A knife assembly is also included having a movable knife rod to operatively engage a knife blade, the knife rod having a first longitudinal section having a first predetermined shape, and a second longitudinal section having a second predetermined shape. The first predetermined shape is different than the second predetermined shape.

8 Claims, 34 Drawing Sheets

Related U.S. Application Data continuation-in-part of application No. 11/595,194, filed on Nov. 9, 2006, now Pat. No. 7,766,910.

(60) Provisional application No. 60/761,442, filed on Jan. 24, 2006, provisional application No. 60/994,348, filed on Sep. 19, 2007.

(51) Int. Cl.
    *A61B 17/32* (2006.01)
    *A61B 17/29* (2006.01)
    *A61B 18/00* (2006.01)
    *A61B 18/18* (2006.01)

(52) U.S. Cl.
    CPC ... *A61B 18/1442* (2013.01); *A61B 2017/2945* (2013.01); *A61B 2018/0063* (2013.01); *A61B 2018/00345* (2013.01); *A61B 2018/00404* (2013.01); *A61B 2018/00607* (2013.01); *A61B 2018/00619* (2013.01); *A61B 2018/1412* (2013.01); *A61B 2018/1432* (2013.01); *A61B 2018/1455* (2013.01); *A61B 2018/1467* (2013.01); *A61B 2018/1861* (2013.01)

(56) References Cited

U.S. PATENT DOCUMENTS

| | | | |
|---|---|---|---|
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |
| 2,279,753 | A | 4/1942 | Knopp |
| 2,305,156 | A | 12/1942 | Grubel |
| 2,327,353 | A | 8/1943 | Karle |
| 2,632,661 | A | 3/1953 | Cristofv |
| 2,668,538 | A | 2/1954 | Baker |
| 2,796,065 | A | 6/1957 | Kapp |
| 3,073,311 | A | 1/1963 | Tibbs et al. |
| 3,372,288 | A | 3/1968 | Wigington |
| 3,459,187 | A | 8/1969 | Pallotta |
| 3,643,663 | A | 2/1972 | Sutter |
| 3,648,001 | A | 3/1972 | Anderson et al. |
| 3,651,811 | A | 3/1972 | Hildebrandt et al. |
| 3,678,229 | A | 7/1972 | Osika |
| 3,720,896 | A | 3/1973 | Beierlein |
| 3,763,726 | A | 10/1973 | Hildebrand |
| 3,779,918 | A | 12/1973 | Ikeda et al. |
| 3,798,688 | A | 3/1974 | Wasson |
| 3,801,766 | A | 4/1974 | Morrison, Jr. |
| 3,862,630 | A | 1/1975 | Balamuth |
| 3,863,339 | A | 2/1975 | Reaney et al. |
| 3,866,610 | A | 2/1975 | Kletschka |
| 3,911,766 | A | 10/1975 | Fridolph et al. |
| 3,920,021 | A | 11/1975 | Hiltebrandt |
| 3,921,641 | A | 11/1975 | Hulka |
| 3,938,527 | A | 2/1976 | Rioux et al. |
| 3,952,749 | A | 4/1976 | Fridolph et al. |
| 3,970,088 | A | 7/1976 | Morrison |
| 3,987,795 | A | 10/1976 | Morrison |
| 4,005,714 | A | 2/1977 | Hiltebrandt |
| 4,016,881 | A | 4/1977 | Rioux et al. |
| 4,041,952 | A | 8/1977 | Morrison, Jr. et al. |
| 4,043,342 | A | 8/1977 | Morrison, Jr. |
| 4,074,718 | A | 2/1978 | Morrison, Jr. |
| 4,076,028 | A | 2/1978 | Simmons |
| 4,080,820 | A | 3/1978 | Allen |
| 4,088,134 | A | 5/1978 | Mazzariello |
| 4,112,950 | A | 9/1978 | Pike |
| 4,127,222 | A | 11/1978 | Adams |
| 4,128,099 | A | 12/1978 | Bauer |
| 4,165,746 | A | 8/1979 | Burgin |
| 4,187,420 | A | 2/1980 | Piber |
| 4,233,734 | A | 11/1980 | Bies |
| 4,236,470 | A | 12/1980 | Stenson |
| 4,300,564 | A | 11/1981 | Furihata |
| 4,311,145 | A | 1/1982 | Esty et al. |
| D263,020 | S | 2/1982 | Rau, III |
| 4,370,980 | A | 2/1983 | Lottick |
| 4,375,218 | A | 3/1983 | DiGeronimo |
| 4,416,276 | A | 11/1983 | Newton et al. |
| 4,418,692 | A | 12/1983 | Guay |
| 4,443,935 | A | 4/1984 | Zamba et al. |
| 4,452,246 | A | 6/1984 | Bader et al. |
| 4,470,786 | A | 9/1984 | Sano et al. |
| 4,492,231 | A | 1/1985 | Auth |
| 4,493,320 | A | 1/1985 | Treat |
| 4,503,855 | A | 3/1985 | Maslanka |
| 4,506,669 | A | 3/1985 | Blake, III |
| 4,509,518 | A | 4/1985 | McGarry et al. |
| 4,552,143 | A | 11/1985 | Lottick |
| 4,574,804 | A | 3/1986 | Kurwa |
| 4,597,379 | A | 7/1986 | Kihn et al. |
| 4,600,007 | A | 7/1986 | Lahodny et al. |
| 4,624,254 | A | 11/1986 | McGarry et al. |
| 4,655,215 | A | 4/1987 | Pike |
| 4,655,216 | A | 4/1987 | Tischer |
| 4,657,016 | A | 4/1987 | Garito et al. |
| 4,662,372 | A | 5/1987 | Sharkany et al. |
| 4,671,274 | A | 6/1987 | Sorochenko |
| 4,685,459 | A | 8/1987 | Koch et al. |
| 4,733,662 | A | 3/1988 | DeSatnick et al. |
| D295,893 | S | 5/1988 | Sharkany et al. |
| D295,894 | S | 5/1988 | Sharkany et al. |
| 4,754,892 | A | 7/1988 | Retief |
| 4,763,669 | A | 8/1988 | Jaeger |
| 4,827,929 | A | 5/1989 | Hodge |
| 4,829,313 | A | 5/1989 | Taggart |
| 4,846,171 | A | 7/1989 | Kauphusman et al. |
| 4,887,612 | A | 12/1989 | Esser et al. |
| 4,938,761 | A | 7/1990 | Ensslin |
| 4,947,009 | A | 8/1990 | Osika et al. |
| 4,985,030 | A | 1/1991 | Melzer et al. |
| 5,007,908 | A | 4/1991 | Rydell |
| 5,026,370 | A | 6/1991 | Lottick |
| 5,026,371 | A | 6/1991 | Rydell et al. |
| 5,035,695 | A | 7/1991 | Weber, Jr. et al. |
| 5,037,433 | A | 8/1991 | Wilk et al. |
| 5,042,707 | A | 8/1991 | Taheri |
| 5,047,046 | A | 9/1991 | Bodoia |
| 5,078,716 | A | 1/1992 | Doll |
| 5,084,057 | A | 1/1992 | Green et al. |
| 5,085,659 | A | 2/1992 | Rydell |
| 5,099,840 | A | 3/1992 | Goble et al. |
| 5,100,430 | A | 3/1992 | Avellanet et al. |
| 5,108,392 | A | 4/1992 | Spingler |
| 5,112,343 | A | 5/1992 | Thornton |
| 5,116,332 | A | 5/1992 | Lottick |
| 5,147,357 | A | 9/1992 | Rose et al. |
| 5,151,102 | A | 9/1992 | Kamiyama et al. |
| 5,151,978 | A | 9/1992 | Bronikowski et al. |
| 5,176,695 | A | 1/1993 | Dulebohn |
| 5,190,541 | A | 3/1993 | Abele et al. |
| 5,196,009 | A | 3/1993 | Kirwan, Jr. |
| 5,197,964 | A | 3/1993 | Parins |
| 5,209,747 | A | 5/1993 | Knoepfler |
| 5,211,655 | A | 5/1993 | Hasson |
| 5,215,101 | A | 6/1993 | Jacobs et al. |
| 5,217,457 | A | 6/1993 | Delahuerga et al. |
| 5,217,458 | A | 6/1993 | Parins |
| 5,217,460 | A | 6/1993 | Knoepfler |
| 5,219,354 | A | 6/1993 | Choudhury et al. |
| 5,244,462 | A | 9/1993 | Delahuerga et al. |
| 5,250,047 | A | 10/1993 | Rydell |
| 5,250,063 | A | 10/1993 | Abidin et al. |
| 5,258,001 | A | 11/1993 | Corman |
| 5,258,006 | A | 11/1993 | Rydell et al. |
| 5,261,918 | A | 11/1993 | Phillips et al. |

(56) References Cited

U.S. PATENT DOCUMENTS

| | | |
|---|---|---|
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Heidmueller nee Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,501,654 A | 3/1996 | Failla et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |

(56) References Cited

U.S. PATENT DOCUMENTS

| | | |
|---|---|---|
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,735,849 A * | 4/1998 | Baden .............. A61B 18/1442 606/205 |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Austin et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |

(56) References Cited

U.S. PATENT DOCUMENTS

| | | |
|---|---|---|
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Van De Moer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,759 B1 * | 7/2001 | Quick ............ A61B 17/32002 204/620 |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |

(56) References Cited

U.S. PATENT DOCUMENTS

| | | |
|---|---|---|
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 8,734,443 B2 | 5/2014 | Hixson et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |

(56) References Cited

U.S. PATENT DOCUMENTS

| | | |
|---|---|---|
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sartor et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0254573 A1 | 12/2004 | Dycus et al. |
| 2004/0260281 A1 | 12/2004 | Baxter et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0119655 A1* | 6/2005 | Moses ............... A61B 18/1442 606/51 |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 02514501 A1 | 10/1976 |
| DE | 2627679 A1 | 1/1977 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |

(56) References Cited

FOREIGN PATENT DOCUMENTS

| | | |
|---|---|---|
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19738457 B4 | 1/2009 |
| EP | 0467501 A1 | 1/1992 |
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0624348 A3 | 6/1995 |
| EP | 0364216 B1 | 1/1996 |
| EP | 0518230 B1 | 5/1996 |
| EP | 0517243 B1 | 9/1997 |
| EP | 0541930 B1 | 3/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1 159 926 A2 | 12/2001 |
| EP | 1177771 | 2/2002 |
| EP | 0717966 B1 | 4/2003 |
| EP | 1301135 | 4/2003 |
| EP | 0887046 B1 | 7/2003 |
| EP | 1330991 | 7/2003 |
| EP | 1486177 | 6/2004 |
| EP | 1472984 | 11/2004 |
| EP | 0754437 B2 | 12/2004 |
| EP | 1025807 B1 | 12/2004 |
| EP | 0774232 B1 | 1/2005 |
| EP | 0853922 B1 | 2/2005 |
| EP | 1527747 | 5/2005 |
| EP | 1530952 | 5/2005 |
| EP | 1532932 | 5/2005 |
| EP | 1535581 | 6/2005 |
| EP | 1609430 | 12/2005 |
| EP | 1034746 B1 | 3/2006 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 0875209 B1 | 5/2006 |
| EP | 1707143 | 10/2006 |
| EP | 1769765 | 4/2007 |
| EP | 1769766 | 4/2007 |
| EP | 1810625 | 7/2007 |
| EP | 1929970 | 6/2008 |
| EP | 1683496 | 12/2008 |
| GB | 623316 | 5/1949 |
| GB | 1490585 | 11/1977 |
| GB | 2213416 A | 8/1989 |
| GB | 2214430 A | 9/1989 |
| JP | 61-501068 | 9/1984 |
| JP | 65-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| RU | 401367 | 11/1974 |
| WO | 89/00757 | 1/1989 |
| WO | 92/04873 | 4/1992 |
| WO | 92/06642 | 4/1992 |
| WO | 93/21845 | 11/1993 |
| WO | 94/08524 | 4/1994 |
| WO | 94/20025 | 9/1994 |
| WO | 95/02369 | 1/1995 |
| WO | 95/07662 | 3/1995 |
| WO | 95/15124 | 6/1995 |
| WO | 96/05776 | 2/1996 |
| WO | 96/22056 | 7/1996 |
| WO | 96/13218 | 9/1996 |
| WO | 97/00646 | 1/1997 |
| WO | 97/00647 | 1/1997 |
| WO | 97/10764 | 3/1997 |
| WO | 97/24073 | 7/1997 |
| WO | 97/24993 | 7/1997 |
| WO | 98/27880 | 7/1998 |
| WO | 99/03407 | 1/1999 |
| WO | 99/03408 | 1/1999 |
| WO | 99/03409 | 1/1999 |
| WO | 99/12488 | 3/1999 |
| WO | 99-23933 A2 | 5/1999 |
| WO | 99/40857 | 8/1999 |
| WO | 99/40861 | 8/1999 |
| WO | 99/51158 | 10/1999 |
| WO | 99/66850 | 12/1999 |
| WO | 00/24330 | 5/2000 |
| WO | 00/24331 | 5/2000 |
| WO | 0036986 A1 | 6/2000 |
| WO | 00/41638 | 7/2000 |
| WO | 00/47124 | 8/2000 |
| WO | 00/53112 | 9/2000 |
| WO | 01/17448 | 3/2001 |
| WO | 0154604 A1 | 8/2001 |
| WO | 02/07627 | 1/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080793 | 10/2002 |
| WO | 02/080794 | 10/2002 |
| WO | 02/080795 | 10/2002 |
| WO | 02/080796 | 10/2002 |
| WO | 02/080797 | 10/2002 |
| WO | 02/080798 | 10/2002 |
| WO | 02/080799 | 10/2002 |
| WO | 02/081170 | 10/2002 |
| WO | 03/061500 | 7/2003 |
| WO | 03/101311 | 12/2003 |
| WO | 03/090630 A3 | 4/2004 |
| WO | 2004/032776 A1 | 4/2004 |
| WO | 2004/032777 A1 | 4/2004 |
| WO | 2004/052221 A1 | 6/2004 |
| WO | 2004/073488 A2 | 9/2004 |
| WO | 2004/073490 A2 | 9/2004 |
| WO | 2004/073753 A2 | 9/2004 |
| WO | 2004/082495 A1 | 9/2004 |
| WO | 2004/098383 A2 | 11/2004 |
| WO | 2004/103156 A2 | 12/2004 |
| WO | 2005/004734 A1 | 1/2005 |
| WO | 2005/004735 A1 | 1/2005 |
| WO | 2005/110264 A2 | 11/2005 |
| WO | 2008/045348 A2 | 4/2008 |
| WO | 2008/045350 A2 | 4/2008 |

OTHER PUBLICATIONS

Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.

(56) References Cited

OTHER PUBLICATIONS

Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report EP 09 152267.2 dated Jun. 15, 2009.
Int'l Search Report EP 09 152898.4 dated Jun. 10, 2009.
Int'l Search Report PCT/US09/032690 dated Jun. 16, 2009.
Extended European Search Report from EP 10 18 5405 dated Jan. 5, 2011.
Extended European Search Report from EP 10 18 5386 dated Jan. 10, 2011.
European Search Report dated Aug. 31, 2011 for EP Appln. No. EP 10 16 7655.
International Search Report EP 09 005051.9 dated Jul. 6, 2009.
European Search Report completed Sep. 2, 2009 and issued by European Patent Office in coresponding European Patent Application No. 09004491 filed Mar. 27, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

(56) References Cited

OTHER PUBLICATIONS

Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Australian Examination Report issued Apr. 28, 2015 from Application No. AU 2013206054.

\* cited by examiner

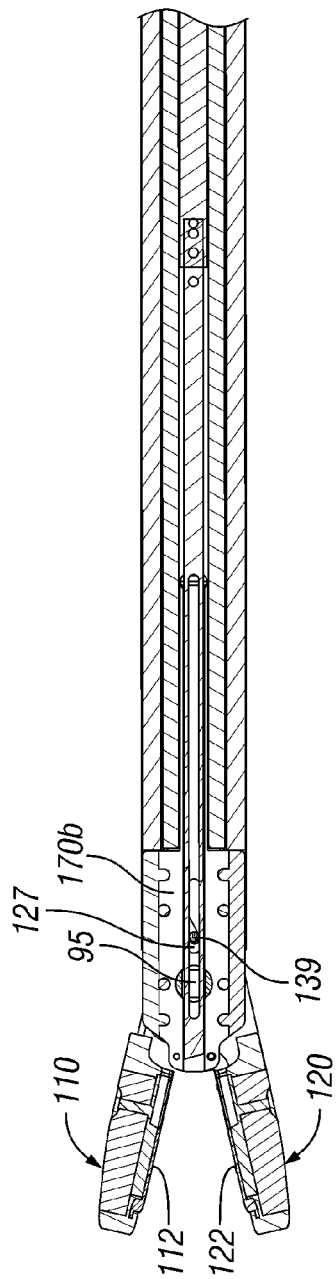
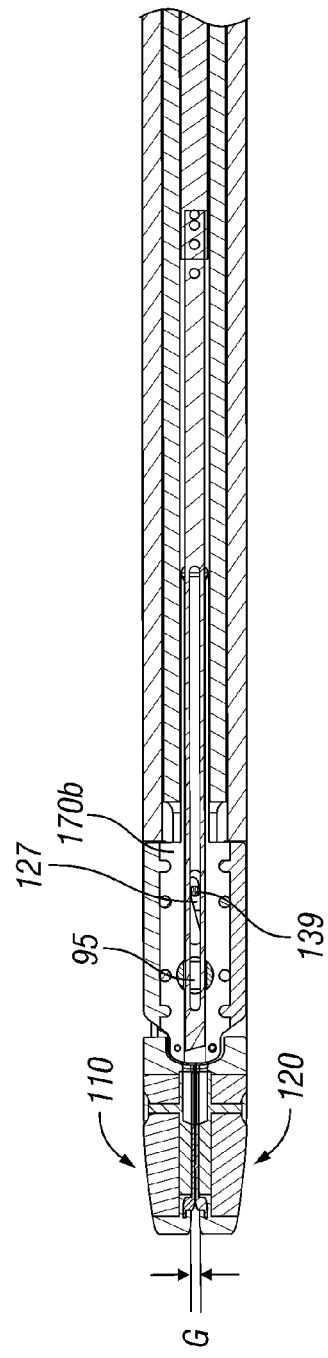
FIG. 8B
FIG. 8C

VESSEL SEALER AND DIVIDER FOR LARGE TISSUE STRUCTURES

CROSS REFERENCE TO RELATED APPLICATIONS

This application is a continuation of U.S. patent application Ser. No. 12/233,951 filed on Sep. 19, 2008 (now U.S. Pat. No. 8,734,443) entitled "VESSEL SEALER AND DIVIDER FOR LARGE TISSUE STRUCTURES" by Hixson et al., which claims the benefit of priority to U.S. Provisional Application Ser. No. 60/994,348 entitled "VESSEL SEALER AND DIVIDER FOR LARGE TISSUE STRUCTURES" filed on Sep. 19, 2007 by Hixson et al. Both of the above applications are incorporated herein by reference.

BACKGROUND

The present disclosure relates to an electrosurgical forceps and more particularly, the present disclosure relates to an endoscopic bipolar electrosurgical forceps for sealing and/or cutting large tissue structures.

TECHNICAL FIELD

Electrosurgical forceps utilize both mechanical clamping action and electrical energy to affect hemostasis by heating the tissue and blood vessels to coagulate, cauterize and/or seal tissue. Many surgical procedures require cutting and/or ligating large blood vessels and large tissue structures. Due to the inherent spatial considerations of the surgical cavity, surgeons often have difficulty suturing vessels or performing other traditional methods of controlling bleeding, e.g., clamping and/or tying-off transected blood vessels or tissue. By utilizing an elongated electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, larger vessels can be more difficult to close using these standard techniques.

In order to resolve many of the known issues described above and other issues relevant to cauterization and coagulation, a recently developed technology has been developed by Valleylab, Inc. of Boulder, Colo., a division of Tyco Healthcare LP called vessel or tissue sealing. The process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass with limited demarcation between opposing tissue structures. Coagulation of small vessels is sufficient to permanently close them, while larger vessels and tissue need to be sealed to assure permanent closure.

In order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal.

As mentioned above, in order to properly and effectively seal larger vessels or tissue, a greater closure force between opposing jaw members is required. It is known that a large closure force between the jaws typically requires a large moment about the pivot for each jaw. This presents a design challenge because the jaw members are typically affixed with pins that are positioned to have small moment arms with respect to the pivot of each jaw member. A large force, coupled with a small moment arm, is undesirable because the large forces may shear the pins. As a result, designers compensate for these large closure forces by either designing instruments with metal pins and/or by designing instruments that at least partially offload these closure forces to reduce the chances of mechanical failure. As can be appreciated, if metal pivot pins are employed, the metal pins should be insulated to avoid the pin acting as an alternate current path between the jaw members that may prove detrimental to effective sealing.

Increasing the closure forces between electrodes may have other undesirable effects, e.g., it may cause the opposing electrodes to come into close contact with one another that may result in a short circuit and a small closure force may cause pre-mature movement of the tissue during compression and prior to activation.

As a result thereof, providing an instrument that consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal for large vessels and tissue structures is between about 3 kg/cm$^2$ to about 16 kg/cm$^2$ and, desirably, within a working range of 7 kg/cm$^2$ to 13 kg/cm$^2$. As can be appreciated, manufacturing an instrument that is capable of consistently providing a closure pressure within these working ranges is quite a design challenge for instrument manufacturers.

Various force-actuating assemblies have been developed in the past for providing the appropriate closure forces to affect vessel sealing. For example, one such actuating assembly has been developed by Valleylab, Inc. of Boulder, Colo., a division of Tyco Healthcare LP, for use with Valleylab's vessel sealing and dividing instrument for sealing large vessels and tissue structures commonly sold under the trademark LIGASURE ATLAS®. The LIGASURE ATLAS® is presently designed to fit through a 10 mm cannula and includes a bi-lateral jaw closure mechanism and is activated by a foot switch. Co-pending U.S. application Ser. Nos. 10/179,863 and 10/116,944 and PCT Application Serial Nos. PCT/US01/01890 and PCT/7201/11340 describe in detail the operating features of the LIGASURE ATLAS® and various methods relating thereto. The contents of all of these applications are hereby incorporated by reference herein.

Other force-actuating assemblies have also been developed by the Valleylab, Inc. of Boulder, Colo., a division of Tyco Healthcare LP, for use with Valleylab's vessel sealing and dividing instrument for sealing large vessels and tissue structures commonly sold under the trademark LIGASURE 5 mm.™ The LIGASURE 5 mm™ is presently designed to fit through a 5 mm cannula and includes a unilateral jaw closure mechanism and is activated by a hand switch. Co-pending U.S. application Ser. Nos. 10/460,926 and 10/953,757 describe in detail the operating features of the LIGASURE 5 mm™ and various methods relating thereto. The entire contents of both of these applications are hereby incorporated by reference herein.

It would be desirous to develop a vessel sealing instrument that consistently produces the required mechanical forces necessary to close the jaw members about very large tissue structures within a preferred pressure range. It would also be desirous for the instrument to provide a mechanical advantage for manipulating the jaw members and clamping tissue, such that, for example, the jaw members can be closed on tissue, easier, quicker and with less user force than previously envisioned to clamp the tissue.

SUMMARY

The forceps includes a housing, a shaft having a longitudinal axis defined therethrough, a drive assembly and a movable handle. The shaft includes an end effector assembly having a pair of jaw members attached to a distal end thereof. The jaw members are movable from a first position in spaced relation to one another to at least a second position closer to one another. The jaw members are for grasping tissue therebetween. Each of the jaw members is adapted to connect to an electrosurgical energy source, thus enabling the jaw members to conduct energy through tissue held between the jaw members to create a tissue seal.

The drive assembly moves the jaw members relative to one another from a first position wherein the jaw members are disposed in spaced relation relative to one another to a second position wherein the jaw members are closer to one another for manipulating tissue. The movable handle is rotatable about a pivot to force a drive flange of the drive assembly to move the jaw members between the first and second positions. The pivot is located a fixed distance above the longitudinal axis and the drive flange is located generally along the longitudinal axis. This mechanical arrangement creates level-like mechanical advantage about the pivot to facilitate closing the jaw members about tissue. The forceps also includes a knife assembly having a generally t-shaped movable knife bar that is dimensioned to operatively engage a corresponding slot defined within the housing. The slot guides the movement of the knife bar during translation thereof.

In one embodiment, the knife bar is operatively coupled to a knife slidingly disposed within the shaft. The forceps further includes a finger actuator operatively coupled to the knife assembly wherein movement of the finger actuator moves the knife bar which, in turn, moves the knife to cut tissue disposed between the jaw members. In another embodiment, the shaft includes a drive sleeve slidingly disposed therein that operatively connects to the drive assembly for moving the jaw members and the knife assembly includes a cuff at the distal end of the knife bar. The cuff is dimensioned to encapsulate and move atop the drive sleeve upon movement of the knife bar. The forceps may also include a finger actuator operatively connected to the knife assembly. The finger actuator includes two generally u-shaped flanges that rotate about a pivot to abut and force the cuff distally which, in turn, results in distal translation of the knife bar.

In yet another embodiment, a spring is included that biases the knife assembly in a proximal-most orientation. A rotating assembly is also included and is configured to rotate the jaw members about the longitudinal axis defined through the shaft. A hand switch may also be included within the housing that is adapted to connect to the source of electrosurgical energy. The hand switch allows a user to selectively supply bipolar energy to the jaw members to affect a tissue seal. At least one of the jaw members includes a series of stop members disposed thereon for regulating the distance between the jaw members during sealing.

The present disclosure also relates to a bipolar forceps that includes a housing having a shaft affixed thereto. The shaft includes jaw members attached at a distal end thereof having a longitudinal axis defined therethrough. The jaw members are adapted to connect to a source of electrosurgical energy such that the jaw members are capable of conducting energy through tissue held therebetween to effect a tissue seal. The forceps also includes a drive assembly that moves the jaw member relative to one another about a pivot from a first position wherein the jaw members are disposed in spaced relation relative to one another to a second position wherein the jaw members are closer to one another for manipulating tissue.

A movable handle is included that is rotatable about a pivot to force a drive flange of the drive assembly to move the jaw members between the first and second positions. The pivot is located a fixed distance above the longitudinal axis and the drive flange is located generally along the longitudinal axis. A trigger assembly is included that is operatively coupled to the housing and operatively coupled to a knife assembly. The knife assembly includes a drive rod which, upon actuation of the trigger assembly, selectively translates a knife through tissue disposed between the jaw members. A knife guide may also be included that is dimensioned to facilitate alignment and translation of the knife through and into a knife channel defined between the jaw members.

In one embodiment, the knife guide includes two engageable halves that insulate the jaw members from one another. The knife guide may also include one or more apertures defined therein that allow the pivot to extend therethrough. The drive assembly may also include a cam pin at a distal end thereof that operatively engages the jaw members and the knife guide may be configured to include one or more slots defined therein that allow the cam pin to extend therethrough.

In another embodiment, the pivot includes an aperture defined therein that allows the knife to extend therethrough. The pivot may include a stem and a cap that matingly engage on opposite sides of the shaft to secure the jaw members during assembly.

In still yet another embodiment, the trigger assembly selectively translates the knife through tissue disposed between the jaw members and the knife assembly includes a knife carriage having a t-shaped distal end that engages the trigger assembly and a proximal end that engages a knife bar slidingly mounted within the housing. The knife bar may include a cuff at a distal end thereof that defines an aperture located therethrough. The shaft is dimensioned to rotate and slide through the aperture of the cuff.

The drive assembly may further include a cam pin that operatively couples the distal end of the drive sleeve to the jaw members for actuation thereof. The knife may be dimensioned to include a slot defined therein that allows the cam pin to extend therethrough.

In embodiments, bipolar forceps include a housing, a shaft affixed to the housing having jaw members at a distal end thereof, the shaft having a longitudinal axis defined therethrough. The jaw members are adapted to connect to a source of electrosurgical energy such that the jaw members are capable of conducting energy through tissue held therebetween to effect a tissue seal.

The drive assembly moves the jaw members relative to one another from a first position wherein the jaw members are disposed in spaced relation relative to one another to a second position wherein the jaw members are closer to one another for manipulating tissue. The movable handle is rotatable about a pivot to force a drive flange of the drive assembly to move the jaw members between the first and second positions. The pivot is located a fixed distance above the longitudinal axis. Moreover, the drive flange is located generally along the longitudinal axis.

The knife assembly has a movable knife rod to operatively engage a knife blade, the knife rod having a first longitudinal section having a first predetermined shape, and a second longitudinal section having a second predetermined shape. In embodiments, the first predetermined shape is different than the second predetermined shape.

In some alternative embodiments, the first longitudinal section of the knife rod has a solid or hollow profile. The first predetermined shape may have a uniform cross-section along the length of the first longitudinal section of the knife rod. The cross-section of the first longitudinal section of the knife rod may be in the shape of a circle, square, rectangle, triangle, quadrilateral, or polygon (e.g., pentagon, hexagon, heptagon, octagon, nonagon, or decagon).

In another particular embodiment, the first longitudinal section of the knife rod has three or more peripheral edges rounded along the length thereof. The first longitudinal section of the knife rod may have one or more longitudinal flanges along the length thereof, and may include a length of about 2.0 inches to about 5.0 inches along its longitudinal axis, and a width of about 0.07 inches to about 0.2 inches.

In embodiments, the knife blade is made of a material such as razor blade stainless steel, high carbon steel, high carbon stainless steel, surgical stainless steel, titanium, ceramic materials, zirconium oxide, aluminum, beryllium copper, brass, copper alloys, nickel silver, phosphorous bronze, stainless steel, steel, and combinations thereof.

In embodiments, the knife rod is operatively coupled to a knife slidingly disposed within the shaft and the forceps further includes a finger actuator operatively coupled to the knife rod wherein movement of the finger actuator moves the knife rod which, in turn, moves the knife to cut tissue disposed between the jaw members. The finger actuator may be in the shape of a wheel on the distal portion of the housing, a lever on the distal portion of the housing, or a wheel having a first rack, a pinion that rotates about a pivot to abut and force the second longitudinal section distally which, in turn, results in distal translation of the knife.

The bipolar forceps may also include a knife guide dimensioned to prevent tissue from entering the knife channel during activation. Suitable knife guides may include a solid body that insulates the jaw members from one another.

BRIEF DESCRIPTION OF THE DRAWINGS

Various embodiments of the subject instrument are described herein with reference to the drawings wherein:

FIG. 8B is an enlarged, side cross-sectional view showing the jaw members in a spaced apart orientation;

FIG. 8C is an enlarged, side cross-sectional view showing the jaw members in a closed orientation;

DETAILED DESCRIPTION

Figure 1A:
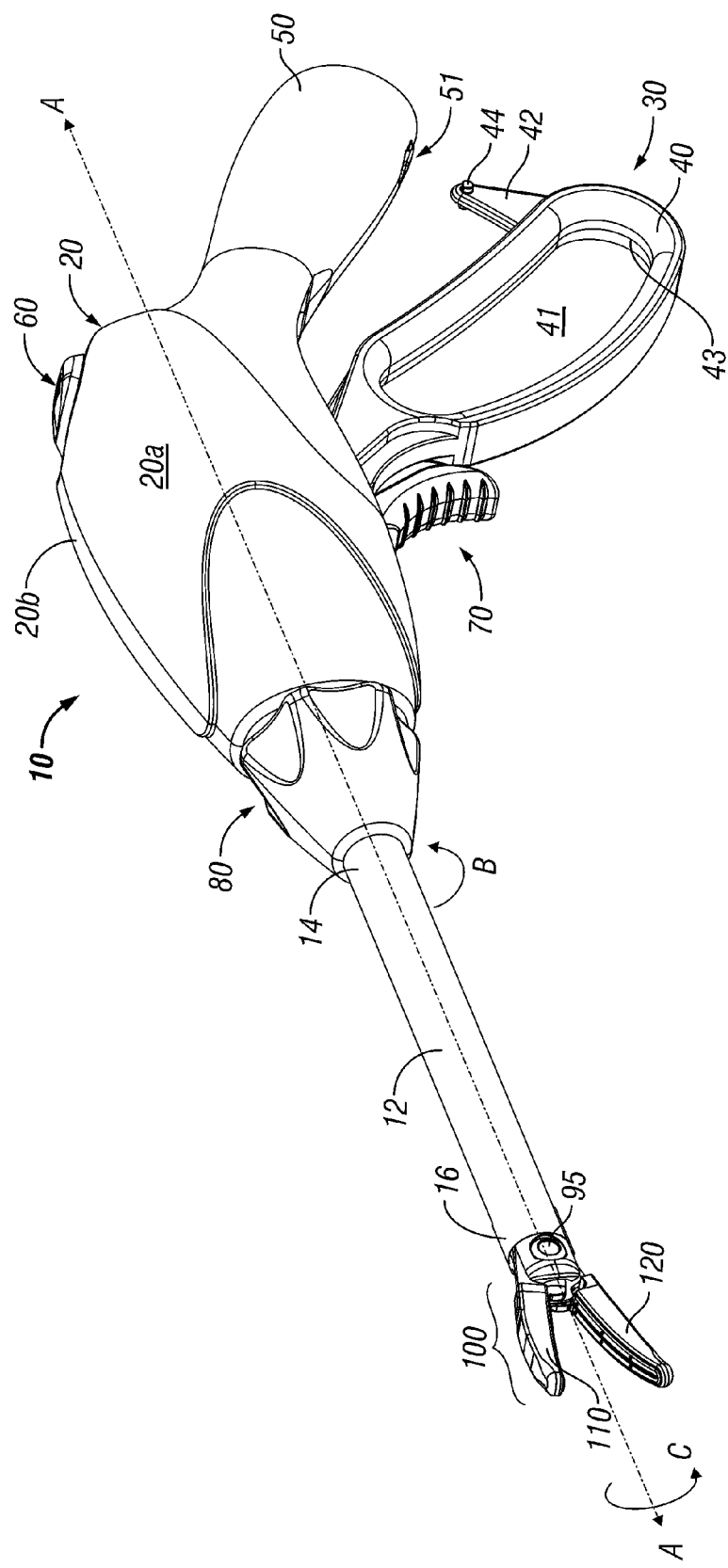
FIG. 1A is a perspective view of a bipolar forceps shown in open configuration and including a housing, a shaft, handle assembly, trigger assembly and an end effector assembly according to the present disclosure.
Figure 1B:
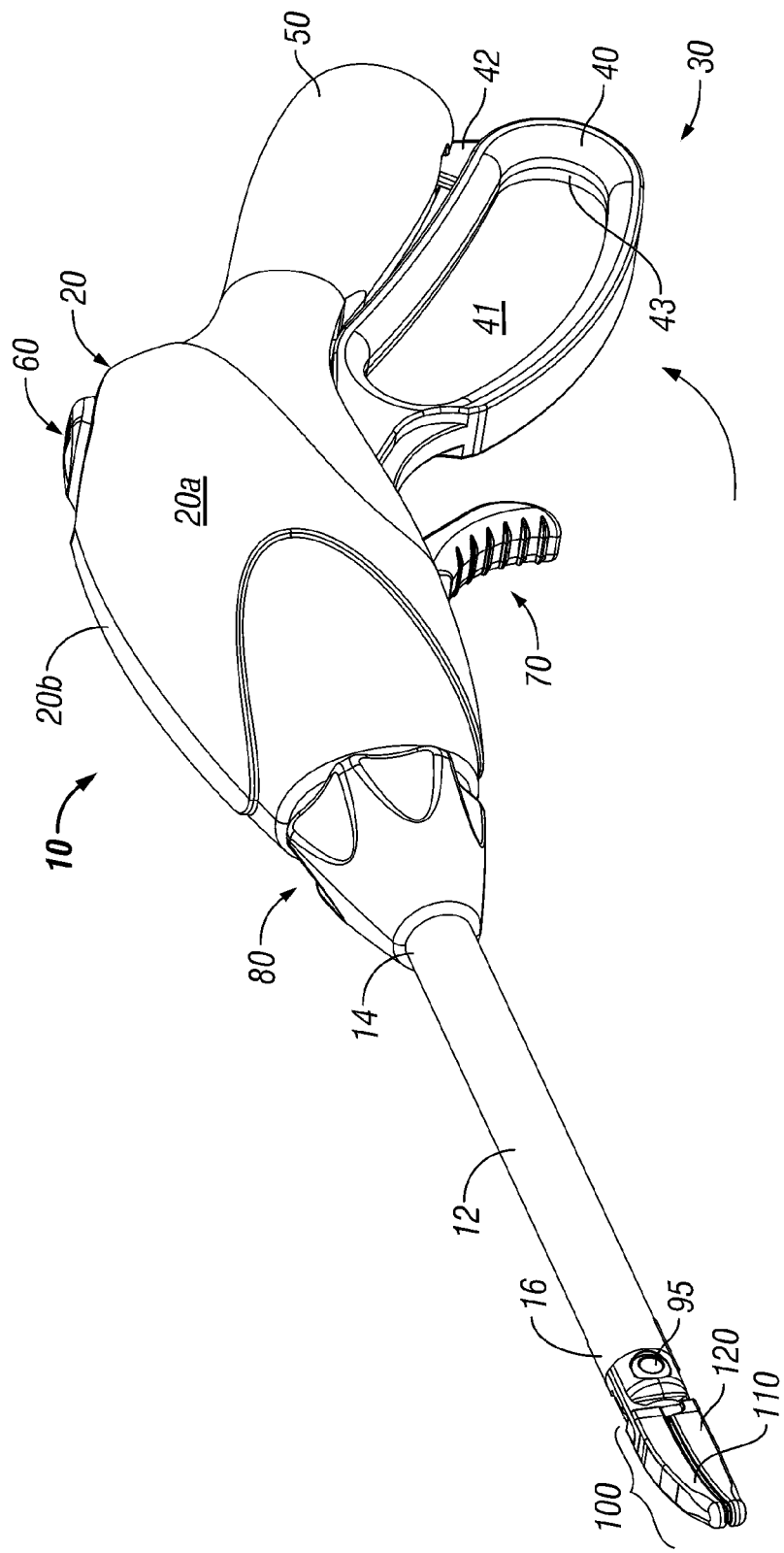
FIG. 1B is a perspective view of the bipolar forceps of FIG. 1A shown in closed configuration.
Figure 2:
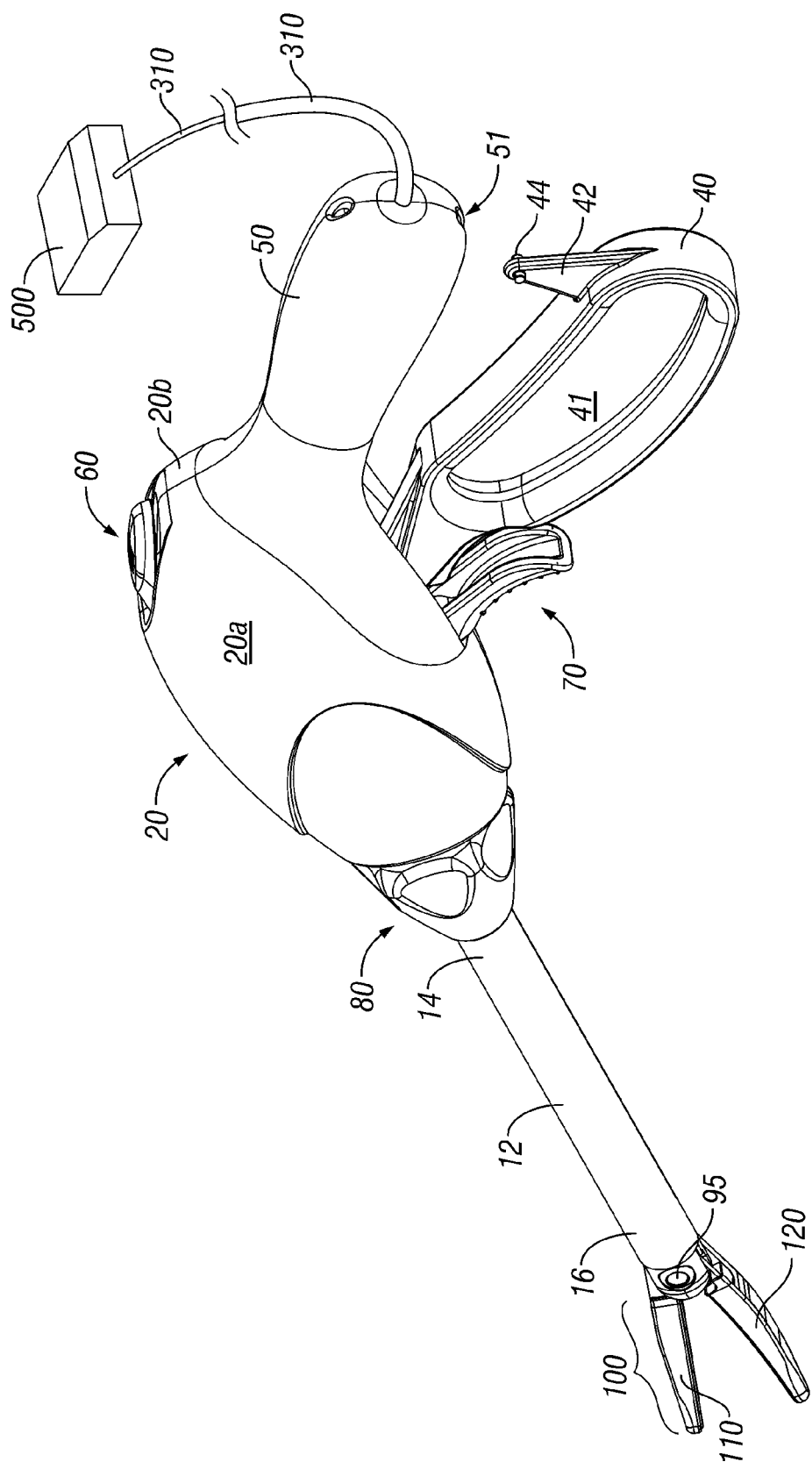
FIG. 2 is a rear view of the forceps of FIG. 1A.

Turning now to FIGS. 1A-2, one embodiment of a bipolar forceps 10 is shown for use with various surgical procedures and generally includes a housing 20, a handle assembly 30, a rotating assembly 80, a trigger assembly 70 and an end effector assembly 100 that mutually cooperate to grasp, seal and divide large tubular vessels and large vascular tissues. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

Forceps 10 includes a shaft 12 that has a distal end 16 dimensioned to mechanically engage the end effector assembly 100 and a proximal end 14 that mechanically engages the housing 20. Details of how the shaft 12 connects to the end effector are described in more detail below with respect to FIGS. 13 and 14. The proximal end 14 of shaft 12 is received within the housing 20 and the connections relating thereto are also described in detail below with respect to FIGS. 11 and 12. In the drawings and in the descriptions that follow, the term "proximal," as is traditional, will refer to the end of the forceps 10 that is closer to the user, while the term "distal" will refer to the end that is farther from the user.

As best seen in FIGS. 1A and 2, forceps 10 also includes an electrosurgical cable 310 that connects the forceps 10 to a source of electrosurgical energy, e.g., a generator 500 (shown schematically). It is contemplated that generators such as those sold by Valleylab—a division of Tyco Healthcare LP, located in Boulder Colo. may be used as a source of electrosurgical energy, e.g., Ligasure™ Generator, FORCE EZ™ Electrosurgical Generator, FORCE FX™ Electrosurgical Generator, FORCE 1C™, FORCE 2™ Generator, SurgiStat™ II or other envisioned generators that may perform different or enhanced functions. One such system is described in commonly-owned U.S. Pat. No. 6,033,399 entitled "ELECTROSURGICAL GENERATOR WITH ADAPTIVE POWER CONTROL" the entire contents of that are hereby incorporated by reference herein. Other systems have been described in commonly-owned U.S. Pat. No. 6,187,003 entitled "BIPOLAR ELECTROSURGICAL INSTRUMENT FOR SEALING VESSELS" the entire contents of which are also incorporated by reference herein.

In one embodiment, the generator 500 includes various safety and performance features including isolated output, independent activation of accessories. It is envisioned that the electrosurgical generator includes Valleylab's Instant Response™ technology features that provides an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;
Reduced thermal spread and risk of collateral tissue damage;
Less need to "turn up the generator"; and
Designed for the minimally invasive environment.

Cable 310 is internally divided into cable leads 310a, 310b and 325b that are designed to transmit electrical potentials through their respective feed paths through the forceps 10 to the end effector assembly 100. More particularly, cable feed 325b connects through the forceps housing 20 and through the rotating assembly to jaw member 120. Lead 310a connects to one side of the switch 60 and lead 310c connects to the opposite side of the switch 60 such that upon activation of the switch energy is transmitted from lead 310a to 310c. Lead 310c is spliced with lead 310b that connects through the rotating assembly to jaw member 110 (See FIG. 6C). Details relating to the electrical connections are explained in more detail below with the discussion of the switch 60.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Fixed handle 50 is oriented approximately 30 degrees relative a longitudinal axis "A-A defined through shaft 12. Fixed handle 50 may include one or more ergonomic enhancing elements to facilitate handling, e.g., scallops, protuberances, elastomeric material, etc.

Rotating assembly 80 is operatively associated with the housing 20 and is rotatable approximately 180 degrees about a longitudinal axis "A-A" (See FIG. 1A). Details of the rotating assembly 80 are described in more detail with respect to FIG. 11.

As mentioned above, end effector assembly 100 is attached at the distal end 14 of shaft 12 and includes a pair of opposing jaw members 110 and 120. Movable handle 40 of handle assembly 30 is ultimately connected to a drive assembly 130 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

Turning now to the more detailed features of the present disclosure as described with respect to FIGS. 1A-21, movable handle 40 includes a finger loop 43 that has an aperture 41 defined therethrough that enables a user to grasp and move the handle 40 relative to the fixed handle 50. Finger loop 43 is typically ergonomically enhanced and may include one or more gripping elements (not shown) disposed along the inner peripheral edge of aperture 41 that are designed to facilitate gripping of the movable handle 40 during activation, e.g., a so called "soft touch" material. Gripping elements may include one or more protuberances, scallops and/or ribs to enhance gripping.

Figure 5A:
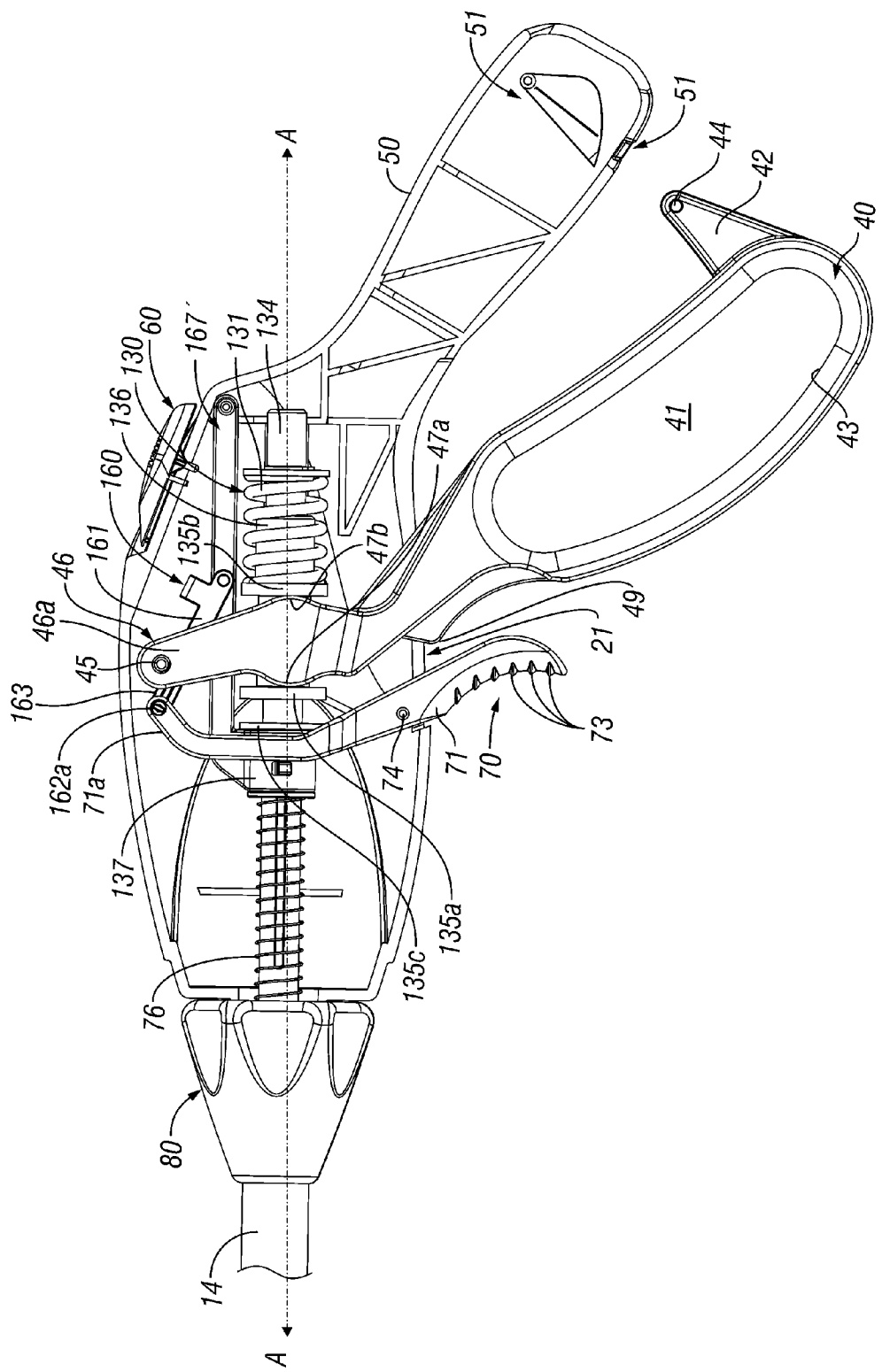
FIG. 5A is side view of the endoscopic forceps of FIG. 1A with the internal working components of the forceps exposed.
Figure 5B:
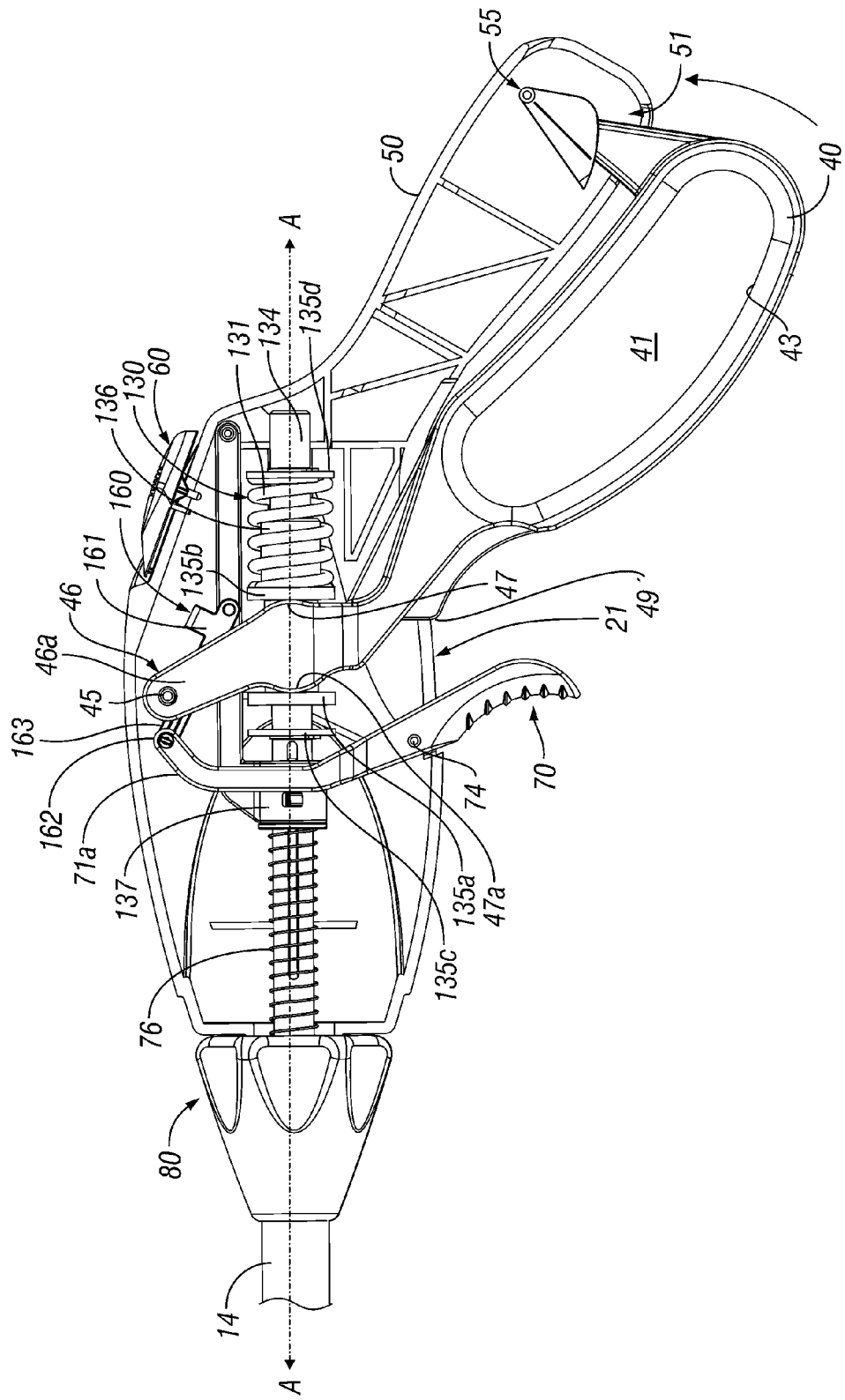
FIG. 5B is side view of the endoscopic forceps of FIG. 1B with the internal working components of the forceps exposed.

As best seen in FIGS. 5A and 5B, movable handle 40 is selectively movable about a pivot pin 45a from a first position relative to fixed handle 50 to a second position in closer proximity to the fixed handle 50 which, as explained below, imparts movement of the jaw members 110 and 120 relative to one another. The movable handle includes a clevis 46 that forms a pair of upper flanges 46a and 46b each having an aperture at an upper end thereof for receiving a pivot pin 45 (See FIG. 12) therethrough and mounting the upper end of the handle 40 to the housing 20. In turn, pivot pin 45 mounts to respective housing halves 20a and 20b. Pivot pin 45 is dimensioned to mount within socket 45a of housing half 20b.

Each upper flange 46a and 46b also includes a force-actuating flange or drive flange 47a and 47b (See FIG. 7), respectively, that are aligned along longitudinal axis "A" and that abut the drive assembly 130 such that pivotal movement of the handle 40 forces actuating flanges 47a and 47b against the drive assembly 130 which, in turn, closes the jaw members 110 and 120 (See FIGS. 5A and 5B). For the purposes herein, 47a and 47b that act simultaneously on the drive assembly 130 are referred to as "driving flange 47". A more detailed explanation of the inter-cooperating components of the handle assembly 30 and the drive assembly 130 is discussed below.

Figure 5C:
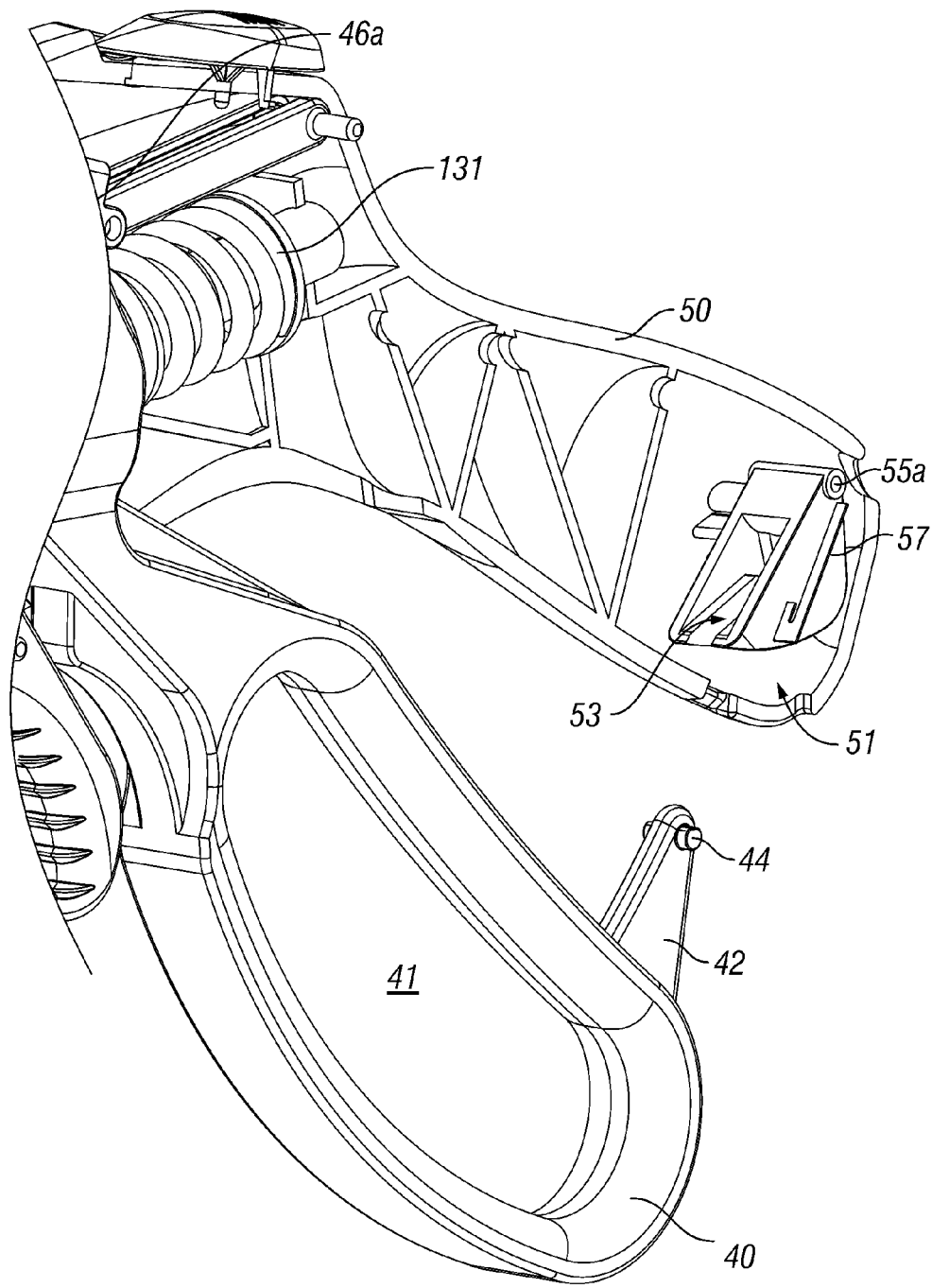
FIG. 5C is a greatly-enlarged, perspective view of the handle assembly in open configuration.

As best shown in FIG. 5C, the lower end of the movable handle 40 includes a flange 42 that is typically integrally associated with or operatively connected to movable handle 40. Flange 42 is typically T-shaped and includes a pin-like element 44 that projects laterally or transversely from a distal end thereof and is configured to engage a corresponding railway 55 disposed within fixed handle 50. More particularly, the pin 44 is configured to ride within a pre-defined channel 53 disposed within the railway 55 to lock the movable handle 40 relative to the fixed handle 50 upon reciprocation thereof. Additional features with respect to the t-shaped pin 44 are explained below in the detailed discussion of the operational features of the forceps 10.

Movable handle 40 is designed to provide a distinct mechanical advantage over conventional handle assemblies due to the unique position of the pivot pin 45 (i.e., pivot point) relative to the longitudinal axis "A" of the shaft 12 and the disposition of the driving flange 47 along longitudinal axis "A". In other words, it is envisioned that by positioning the pivot pin 45 above the driving flange 47, the user gains lever-like mechanical advantage to actuate the jaw members 110 and 120 enabling the user to close the jaw members 110 and 120 with lesser force while still generating the required forces necessary to effect a proper and effective tissue seal.

As shown best in FIGS. 3A-3F, 13 and 14, the end effector assembly 100 includes opposing jaw members 110 and 120 that cooperate to effectively grasp tissue for sealing purposes. The end effector assembly 100 is designed as a bilateral assembly, i.e., both jaw members 110 and 120 pivot relative to one another about a pivot pin 95 disposed therethrough. The jaw members 110 and 120 are curved to facilitate manipulation of tissue and to provide better "line of sight" for accessing organs and large tissue structures.

Figure 13:
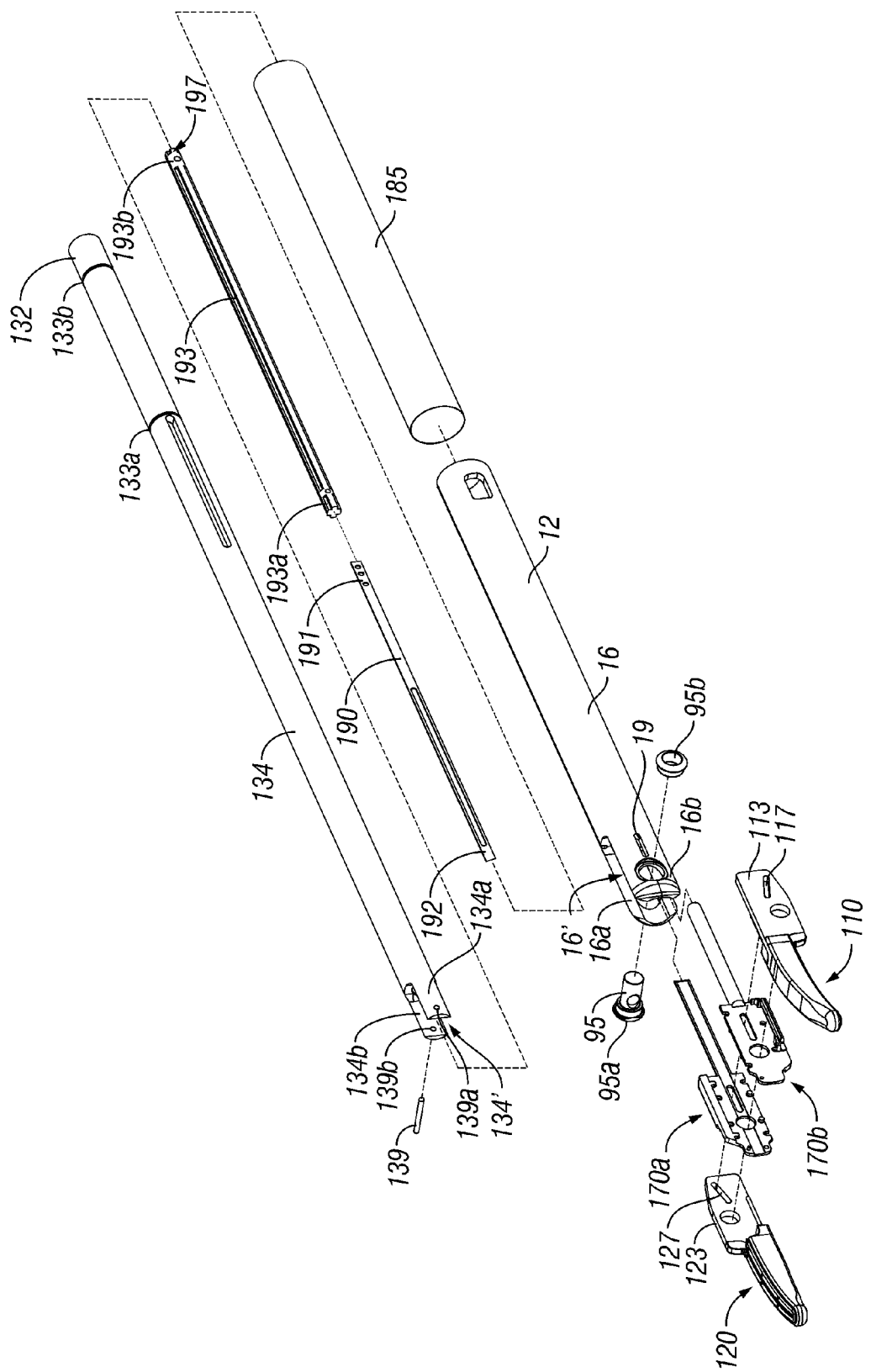
FIG. 13 is an enlarged, exploded perspective view of the end effector assembly and the shaft.
Figure 14:
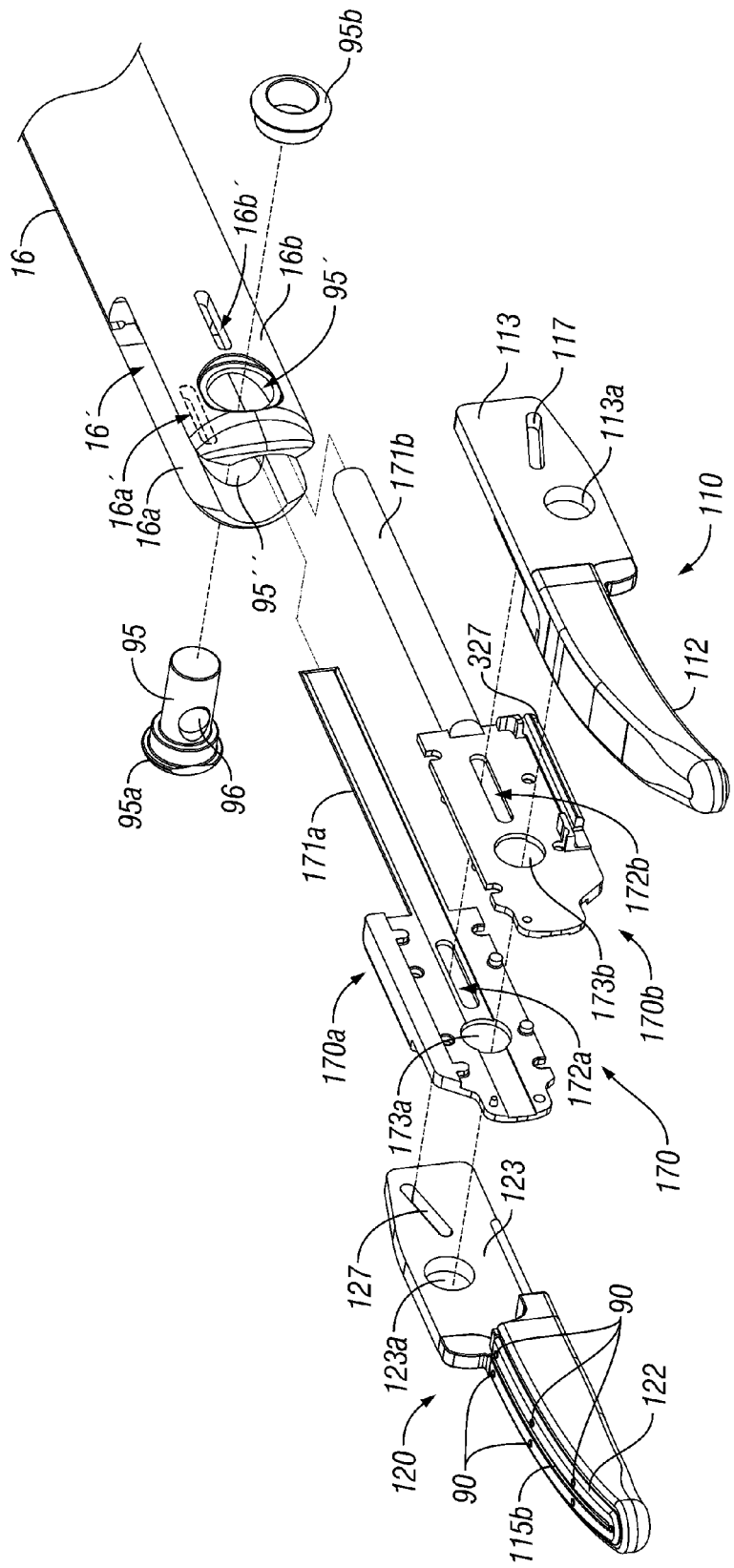
FIG. 14 is a greatly enlarged, exploded perspective view of the end effector assembly.

A reciprocating drive sleeve 134 is slidingly disposed within the shaft 12 and is remotely operable by the drive assembly 130 as explained in more detail below. Drive sleeve 134 includes a bifurcated distal end composed of halves 134a and 134b, respectively, that define a cavity 134' therebetween for receiving jaw members 110 and 120. More particularly and as best illustrated in FIGS. 13 and 14, jaw members 110 and 120 include proximal flanges 113 and 123, respectively, that each include an elongated angled slot 117 and 127, respectively, defined therethrough. A drive pin 139 (See FIG. 13) mounts jaw members 110 and 120 to the end of a sleeve 134 and within cavity 134' disposed between flanges 134a and 134b. Cam pin or drive pin 139 mounts through apertures 139a and 139b defined in flanges 134a and 134b, respectively, and is reciprocable within slots 16a' and 16b' disposed at the distal ends 16a and 16b of shaft 12 (See FIG. 14). It is envisioned that slots 16a' and 16b' may extend into aperture 95' and 95" to facilitate assembly of pin 139. Pin 139 may be composed of two mechanically interfacing elements that are dimensioned to frictionally receive one another to retain pin 139 in place once assembled. Alternatively or in addition, pin 139 may be held in place by one of several known manufacturing techniques including: laser or heat-based welding, press-fit mechanical interaction (or other mechanically interlocking geometry, adhesives, chemical bonding, etc. A component disposed on the outside of shaft 12 may also be utilized to retain the pin 139 in place once assembled. For example, a heat shrink material, adhesive tape, rubber or other insulating boot or silicone may be used for this purpose. It is also envisioned that a varying diameter version of pin 139 may be utilized to prevent the pin from coming loose once assembled. It is also envisioned that a cap or stem (not shown) arrangement may be employed for this purpose as well.

Drive sleeve 134, that ultimately connects to the drive assembly 130, is dimensioned to slidingly receive knife drive rod 193, knife 190 and posts 171a and 171b of halves 170a and 170b of knife guide 170. Drive sleeve 134, in turn, is received within shaft 12. Upon actuation of the drive assembly 130, the drive sleeve 134 reciprocates which, in turn, causes the drive pin 139 to ride within slots 117 and 127 to open and close the jaw members 110 and 120 as desired. The jaw members 110 and 120, in turn, pivot about pivot pin 95 disposed through respective pivot holes 113a and 123a disposed within flanges 113 and 123. As can be appreciated, squeezing handle 40 toward handle 50 pulls drive sleeve 134 and drive pin 139 proximally to close the jaw members 110 and 120 about tissue grasped therebetween and pushing the sleeve 134 distally opens the jaw members 110 and 120 for grasping purposes.

Turning back to the details of the jaw member 110 and 120 as best shown in FIGS. 3A-3F, jaw member 110 includes a support base 119 that extends distally from flange 113 and that is dimensioned to support an insulative plate 119' thereon. Insulative plate 119', in turn, is configured to support an electrically conductive tissue engaging surface or sealing plate 112 thereon. It is contemplated that the sealing plate 112 may be affixed atop the insulative plate 119' and support base 119 in any known manner in the art, snap-fit, over-molding, stamping, ultrasonically welded, etc. Support base 119 together with the insulative plate 119' and electrically conductive tissue engaging surface 112 are encapsulated by an outer insulative housing 116. Outer housing 116 includes a cavity 116a that is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate or other more common methods known in the art (i.e., a conductive surface bound to a structural support via an insulating material). All of these manufacturing techniques produce jaw member 110 having an electrically conductive surface 112 that is substantially surrounded by an insulating housing or substrate 116.

Figure 3A:
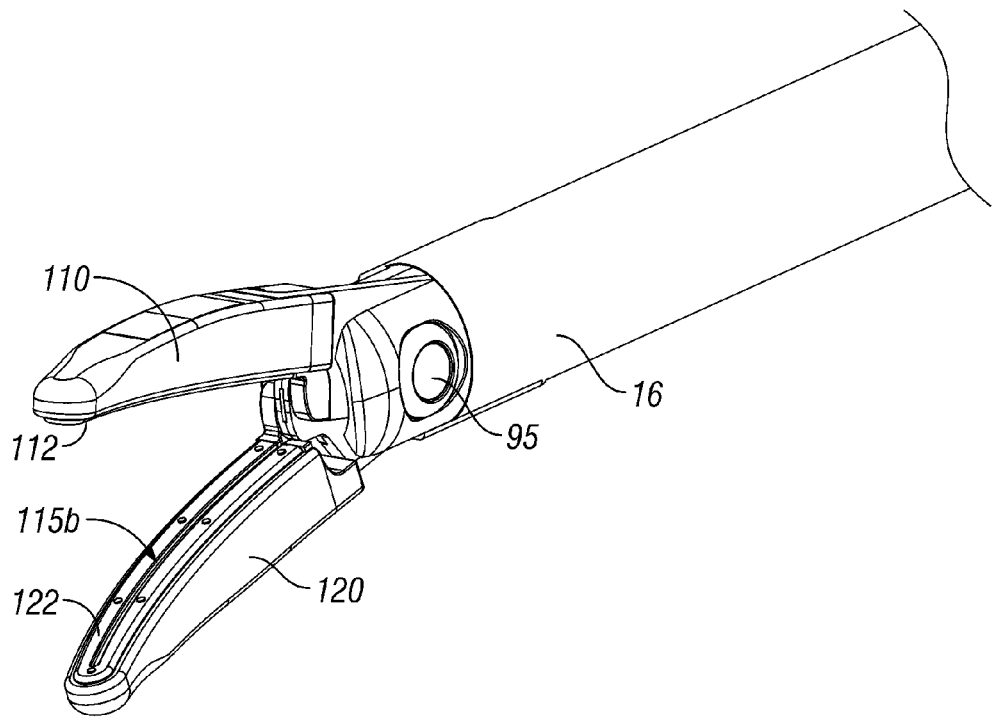
FIG. 3A is an enlarged, front perspective view of the end effector assembly of FIG. 1A shown in an open configuration.
Figure 3B:
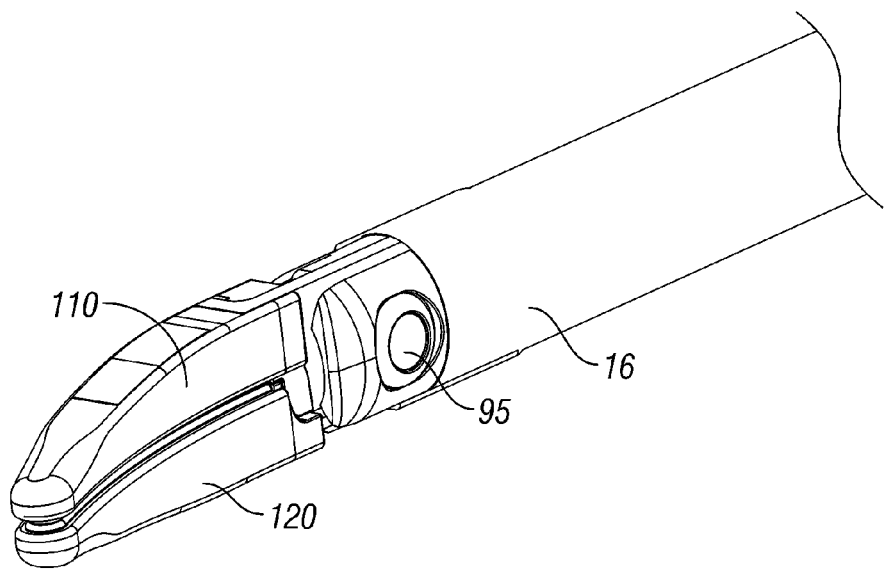
FIG. 3B is an enlarged, front perspective view of the end effector assembly of FIG. 1A shown in a closed configuration.
Figure 3C:
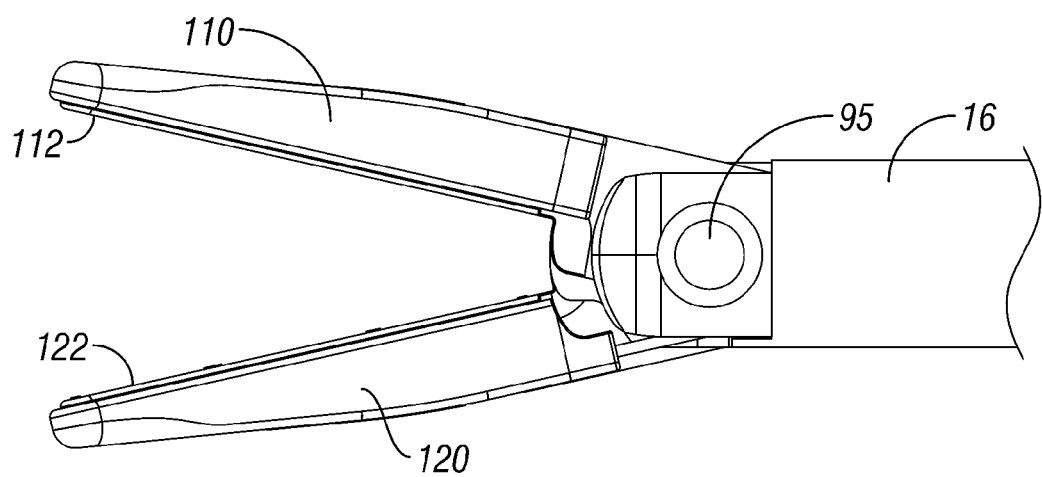
FIG. 3C is an enlarged, side view of the end effector assembly of FIG. 1A shown in open configuration.
Figure 3D:
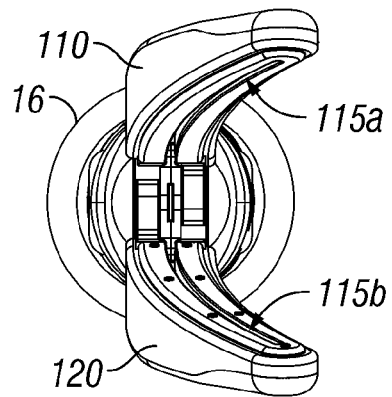
FIG. 3D is an enlarge, front view of the end effector assembly of FIG. 1A shown in open configuration.
Figure 3E:
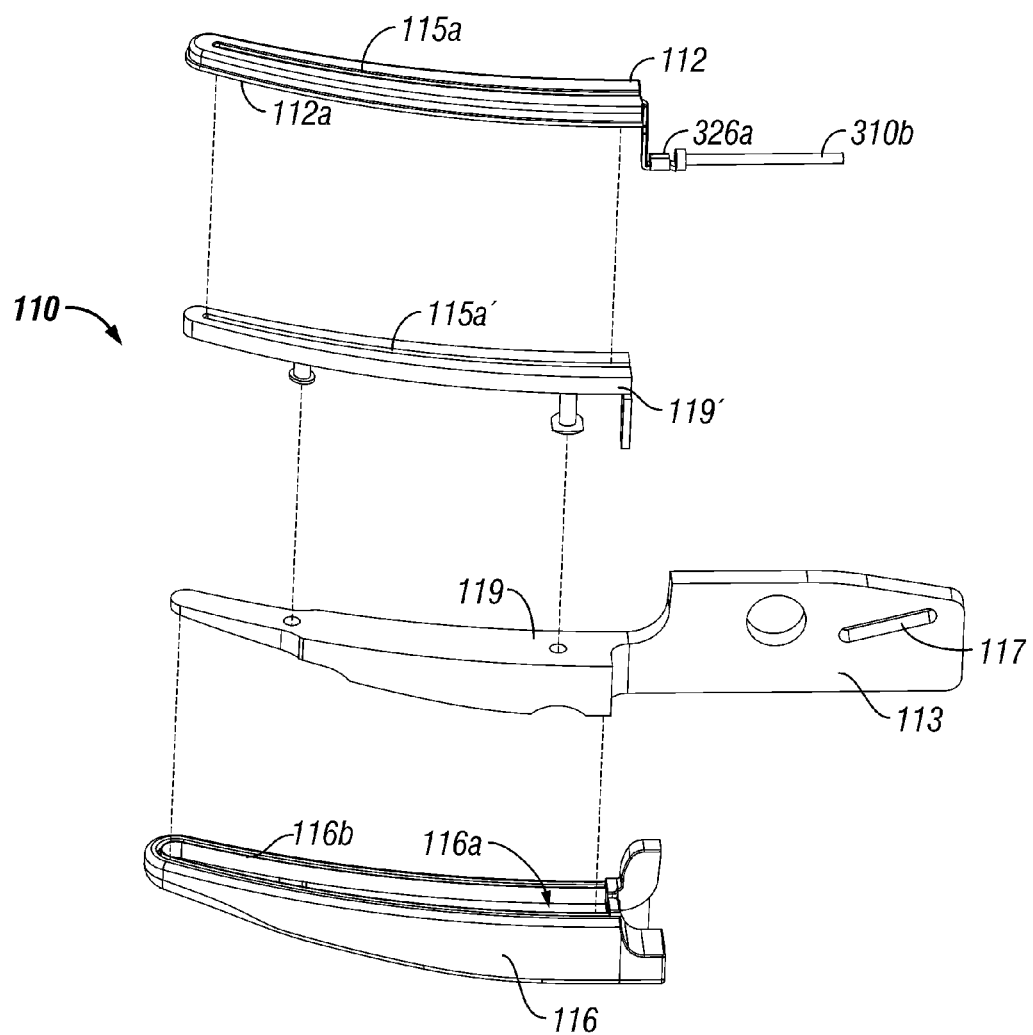
FIG. 3E is a greatly-enlarged, exploded perspective view of the top jaw member.

For example and as shown in FIG. 3E, the electrically conductive sealing plate 112 includes a peripheral flange 112a that surrounds the periphery of the sealing plate 112. Flange 112a is designed to matingly engage an inner lip 116b of the outer insulator 116. Again, this may be accomplished by any of the aforementioned known processes, e.g., overmolding. It is envisioned that lead 310b that extends from switch 60 (See FIG. 6C) terminates within the outer insulator 116 and is designed to electro-mechanically couple to the sealing plate 112 by virtue of a crimp-like connection 326a. Insulator 119', electrically conductive sealing surface 112 and the outer, non-conductive jaw housing 116 are preferably dimensioned to limit and/or reduce many of the known undesirable effects related to tissue sealing, e.g., flashover, thermal spread and stray current dissipation.

It is envisioned that the electrically conductive sealing surface 112 may also include an outer peripheral edge that has a pre-defined radius and the outer housing 116 meets the electrically conductive sealing surface 112 along an adjoining edge of the sealing surface 112 in a generally tangential position. At the interface, the electrically conductive surface 112 is raised relative to the outer housing 116. These and other envisioned embodiments are discussed in co-pending, commonly assigned Application Serial No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned Application Serial No. PCT/US01/11411 entitled "ELECTROSURGICAL INSTRUMENT WHICH IS DESIGNED TO REDUCE THE INCIDENCE OF FLASHOVER" by Johnson et al., the entire contents of both of which being hereby incorporated by reference herein.

The electrically conductive surface or sealing plate 112 and the outer housing 116, when assembled, form a longitudinally-oriented slot 115a defined therethrough for reciprocation of the knife blade 190 (See FIG. 13). It is envisioned that knife slot 115a cooperates with a corresponding knife slot 115b defined in jaw member 120 to facilitate longitudinal extension of the knife blade 190 along a preferred cutting plane to effectively and accurately separate the tissue along the formed tissue seal. Together, knife slots 115a and 115b form knife channel 115 for reciprocation of the knife 190. As best illustrated in FIGS. 3A-3F, knife channel 115 runs through the center of the jaw members 110 and 120, respectively, such that a blade 190 from the knife assembly 70 can cut the tissue grasped between the jaw members 110 and 120 when the jaw members 110 and 120 are in a closed position. As described in more detail below, handle 30a includes a passive lockout flange 49' that prevents actuation of the knife assembly 70 when the handle 40 is open thus preventing accidental or premature activation of the blade 190 through the tissue. In addition, the passive lockout flange 49' is dimensioned to force the trigger 70 to retract the knife 190 when the handle 40 is moved to an open position.

As explained above and as illustrated in FIGS. 3F, 8B, 8C, 10C and 10D, the knife channel 115 is formed when the jaw members 110 and 120 are closed. In other words, the knife channel 115 includes two knife channel halves—knife slot 115a disposed in sealing plate 112 of jaw member 110 and knife slot 115b disposed sealing plate 122 of jaw member 120. It is envisioned that the knife channel 115 may be dimensioned to include some degree of curvature to cause the knife 190 to move through tissue in a curved fashion. Alternatively, the knife channel 115 may be configured as a straight slot with no degree of curvature which, in turn, causes the knife 190 to move through the tissue in a substantially straight fashion. Insulating plate 119' also forms part of the knife channel 115 and includes slot 115a' defined therein that extends along insulating plate 119' and that aligns in vertical registration with knife slot 115a to facilitate translation of distal end 192 of the knife 190 therethrough.

As mentioned above, end effector assembly 100 also includes knife guide 170 that is dimensioned to facilitate alignment and translation of the knife 190 through and into the knife channel 115. More particularly, knife guide 170 includes half 170a and half 170b that mechanically interface to encapsulate the knife 190 upon assembly (See FIG. 13). It is envisioned that knife guide 170, once assembled, aligns the knife 190 for facile translation through knife channel 115 upon reciprocation of a knife drive rod 193 (FIG. 13). The operation of the drive rod 193 is described below with reference to the operational features of the forceps 10. Each half 170a and 170b of the knife guide 170 includes various interfaces thereon and apertures defined therein that allow unencumbered movement of the various operating features of the end effector assembly 100, e.g., pivot 95, drive pin 139 and knife 190. More particularly, halves 170a and 170b include apertures 173a and 173b, respectively, defined therethrough that allow passage of the pivot 95 during assembly. Halves 170a and 170b also include laterally-aligned slots 172a and 172b defined therein that allow reciprocation of the drive pin 139 upon opening and closing of the jaw members 110 and 120. One or more guides 327 (FIG. 14) may also be included to guide leads, e.g., lead 325a, along knife guide 170 and to the electrically conductive plates, e.g., plate 122. Knife guide halves 170a and 170b also include posts 171a and 171b that extend proximally into slot 16' upon assembly to engage knife 190. In embodiments, knife guide is a single molded part assembled around the blade 193 and/or pivot 95. As best shown in FIG. 13, knife guide 170a and 170b include a shaped flange portion 700. Here, flange portion 700 is of a predetermined shape designed to push tissue away from the knife channel 115 during use of the device.

Knife channel 115 runs through the center of the jaw members 110 and 120, respectively, such that a distal end 192 of the knife 190 can cut the tissue grasped between the jaw members 110 and 120 when the jaw members 110 and 120 are in a closed position. More particularly and as described in more detail below with respect to the operation of the forceps 10, the knife 190 can only be advanced through the tissue when the jaw members 110 and 120 are closed thus preventing accidental or premature activation of the knife 190 through the tissue. Passive lockout flange 49' detailed below prevents unintended translation of the knife 190 while the jaw members 110 and 120 are disposed in an open configuration. It is also envisioned that the knife 190 be dimensioned to allow other components to pass therethrough that additionally creates the benefit of enhancing the overall flexibility of the knife to facilitate passage through the knife channel 115.

Alternatively, one or both jaw members may also include a safety lockout to prevent the knife 190 from advancing while the jaw members are in an open configuration. Various safety lockout configurations are disclosed in commonly owned, co-pending U.S. application Ser. No. 10/962,116 entitled "OPEN VESSEL SEALING INSTRUMENT WITH CUTTING MECHANISM AND DISTAL LOCKOUT" and commonly owned, co-pending U.S. Provisional Application Ser. No. 60/722,177 entitled "IN-LINE VESSEL SEALER AND DIVIDER", the entire contents of which are both incorporated by reference herein.

Jaw member 120 includes similar elements to jaw member 110 such as jaw housing 126 that encapsulates a support plate 129, an insulator plate 129' and an electrically conductive sealing surface 122. Likewise, the electrically conductive surface 122 and the insulator plate 129', when assembled, include respective longitudinally-oriented knife slots 115b and 115b' defined therethrough for reciprocation of the knife blade 190. As mentioned above, when the jaw members 110 and 120 are closed about tissue, knife slots 115a and 115b form a complete knife channel 115 to allow longitudinal extension of the knife 190 in a distal fashion to sever tissue along a tissue seal. It is also envisioned that the knife channel 115 may be completely disposed in one of the two jaw members, e.g., jaw member 120, depending upon a particular purpose. It is also envisioned that jaw member 120 may be assembled in a similar manner as described above with respect to jaw member 110. More particularly, the sealing plate 122 may be dimensioned to include an outer peripheral rim 122a that is dimensioned to mechanically interface with an inner lip 126b of housing 126 to secure the sealing plate 122 to the housing 126 with plates 129 and 129' encapsulated therein.

Figure 3F:
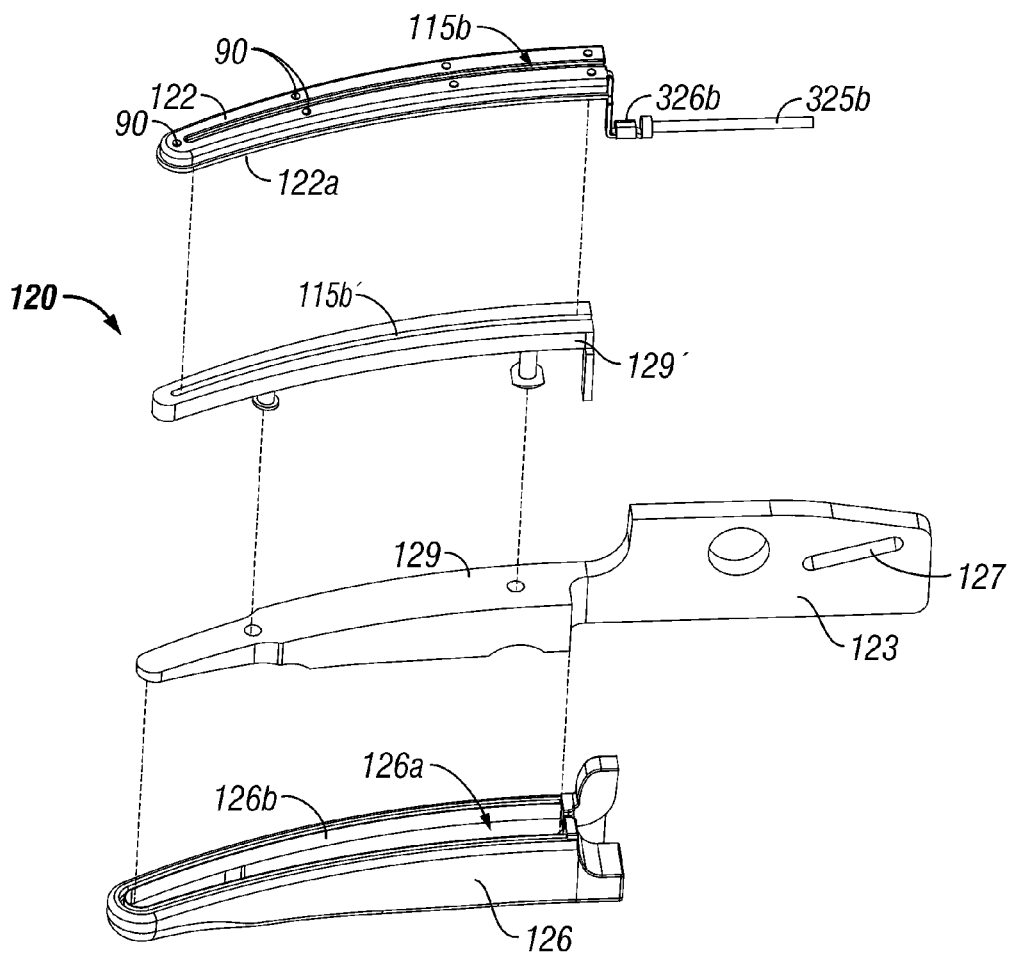
FIG. 3F is a greatly-enlarged, exploded perspective view of the bottom jaw member.
Figure 4:
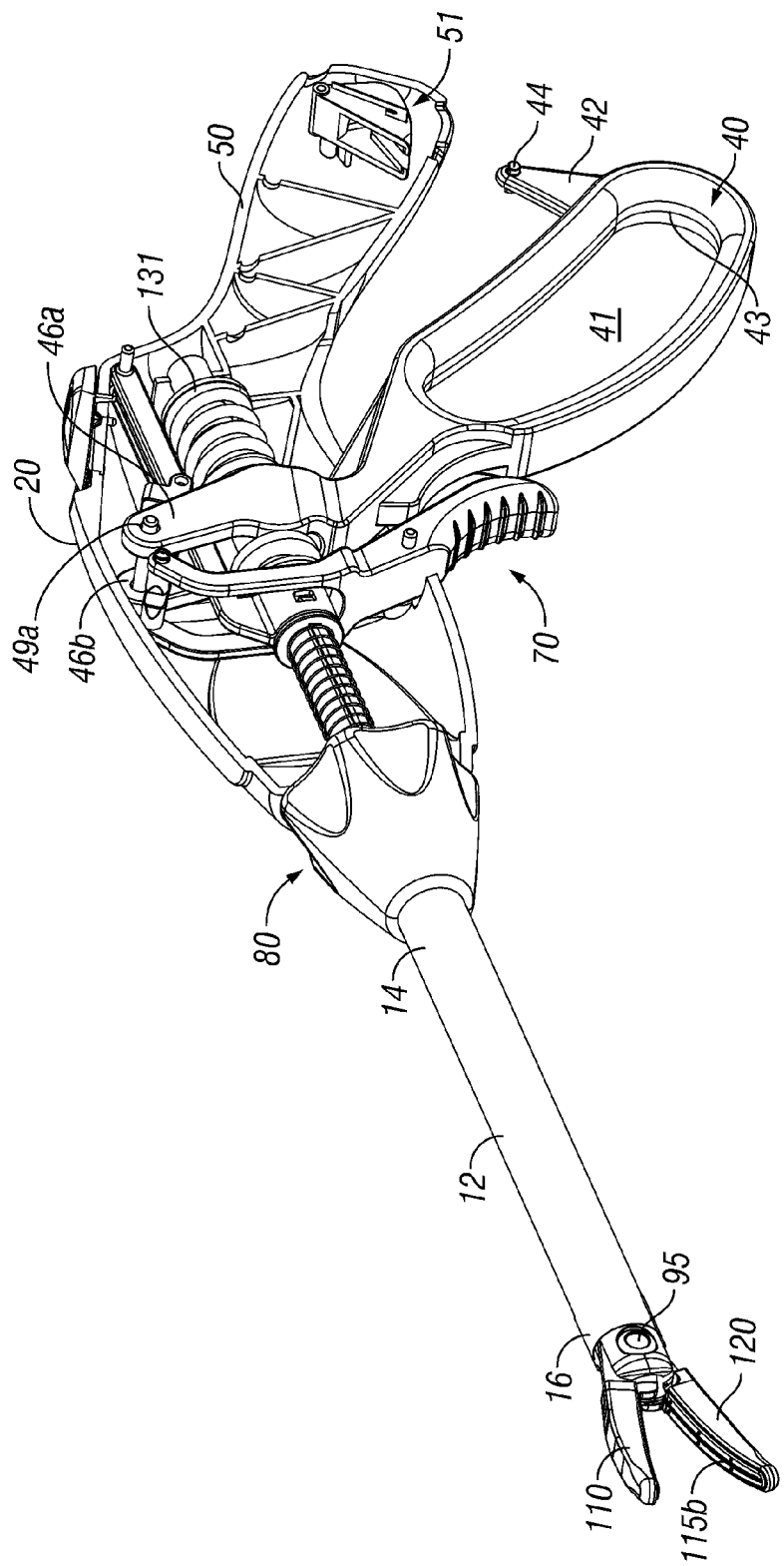
FIG. 4 is a perspective view of the endoscopic forceps of FIG. 1A with the internal working components of the forceps exposed.

As best seen in FIG. 3F, jaw member 120 includes a series of stop members 90 disposed on the inner facing surface of the electrically conductive sealing surface 122 to facilitate gripping and manipulation of tissue and to define a gap "G" (FIG. 10B) between opposing jaw members 110 and 120 during sealing and cutting of tissue. It is envisioned that the series of stop members 90 may be employed on one or both jaw members 110 and 120 depending upon a particular purpose or to achieve a desired result. A detailed discussion of these and other envisioned stop members 90 as well as various manufacturing and assembling processes for attaching and/or affixing the stop members 90 to the electrically conductive sealing surfaces 112, 122 are described in commonly-assigned, co-pending U.S. Application Serial No. PCT/US01/11413 entitled "VESSEL SEALER AND DIVIDER WITH NON-CONDUCTIVE STOP MEMBERS" by Dycus et al. which is hereby incorporated by reference in its entirety herein.

Jaw member 120 is connected to a second electrical lead 325b extending from switch 60 (See FIG. 6B) that terminates within the jaw housing 126 and is designed to electromechanically couple to the sealing plate 122 by virtue of a crimp-like connection 326b. As explained in more detail below, leads 310b and 325b allow a user to selectively supply bipolar electrosurgical energy to the jaw members 110 and 120 as needed during surgery.

Jaw members 110 and 120 are electrically isolated from one another such that electrosurgical energy can be effectively transferred through the tissue to form a tissue seal. For example and as best illustrated in FIGS. 3A-3F, each jaw member 110 and 120 includes a uniquely-designed electrosurgical cable path that transmits electrosurgical energy through the cable leads 310b and 325b to the electrically conductive sealing surfaces 112 and 122, respectively. Cable leads 310b and 325b are held loosely but securely along the cable path to permit rotation of the jaw members 110 and 120. As can be appreciated, this isolates electrically conductive sealing surfaces 112 and 122 from the remaining operative components of the end effector assembly 100 and shaft 12. The two electrical potentials are isolated from one another by virtue of the insulative sheathing surrounding the cable leads 310b and 325b.

Jaw members 110 and 120 are engaged to the end of rotating shaft 12 by pivot pin 95 such that rotation of the rotating assembly 80 correspondingly rotates shaft 12 (along with sleeve 134 and knife 190) which, in turn, rotates end effector assembly 100 (See FIG. 1A). More particularly, the distal end of rotating shaft 12 is bifurcated to include ends 16a and 16b that define a channel 16' therein for receiving jaw members 110 and 120. Pivot pin 95 includes a stem 95a and cap 95b arrangement that is dimensioned to engage through aperture 95' and 95" disposed in ends 16b and 16a, respectively. Upon assembly and as best illustrated in FIGS. 13 and 14, the stem 95a of pivot pin 95 extends, in order, through end 16a of shaft 12, aperture 123a of jaw member 120, aperture 173a of half 170a or knife guide 170, aperture 173b of half 170b of knife guide 170, aperture 113a of jaw member 110 and end 16b of shaft 12 to engage cap 95b. Slots 16a' and 16b' are defined within distal ends 16a and 16b and are dimensioned to allow reciprocation of drive pin 139 therein. Stem 95a includes a pass through hole 96 defined therein that allows passage of the knife 190 therethrough for severing tissue while still allowing a large rotational surface area for the jaw members during loading.

Figure 11:
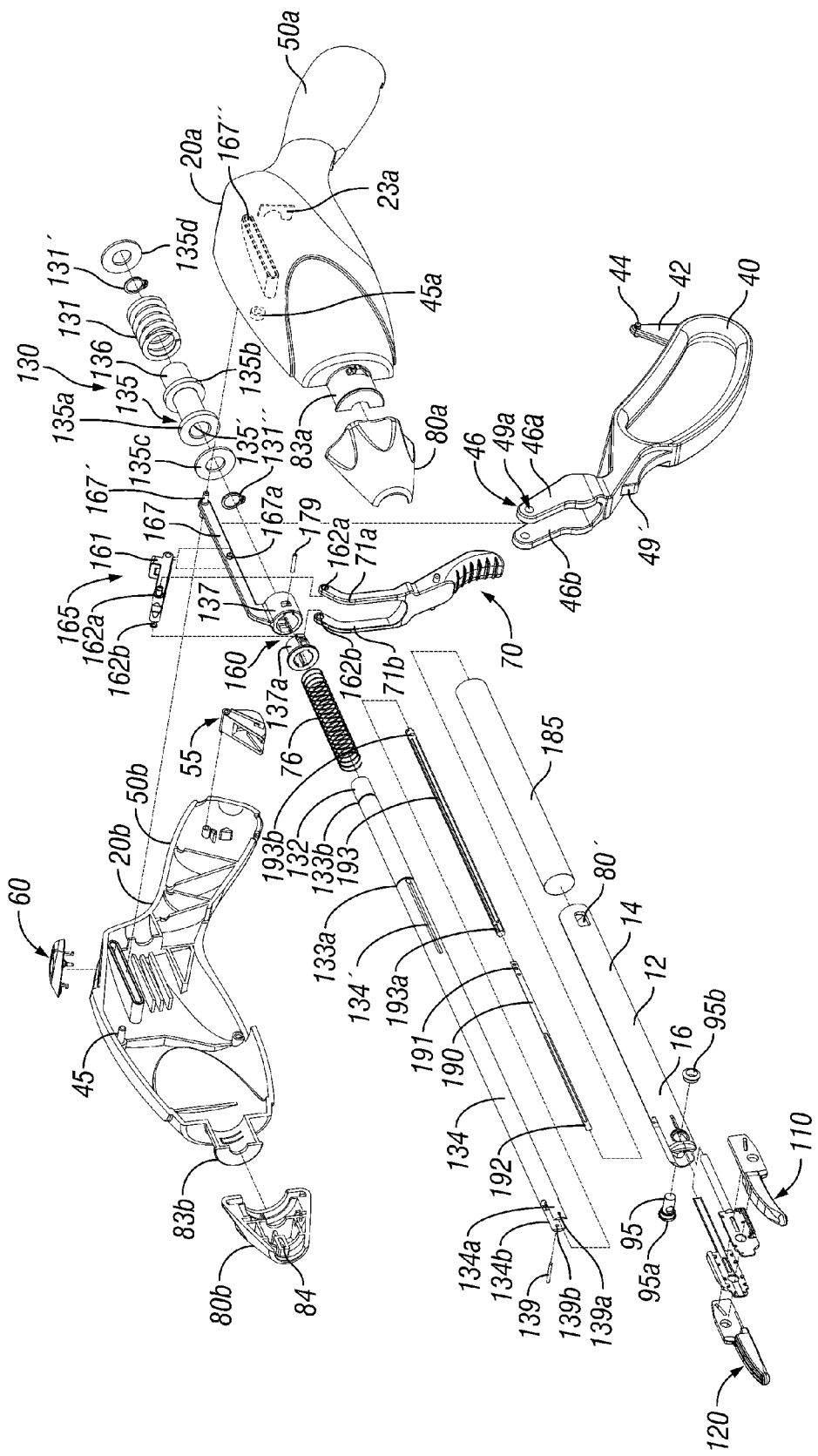
FIG. 11 is an exploded, perspective view of the forceps of FIG. 1A.
Figure 12:
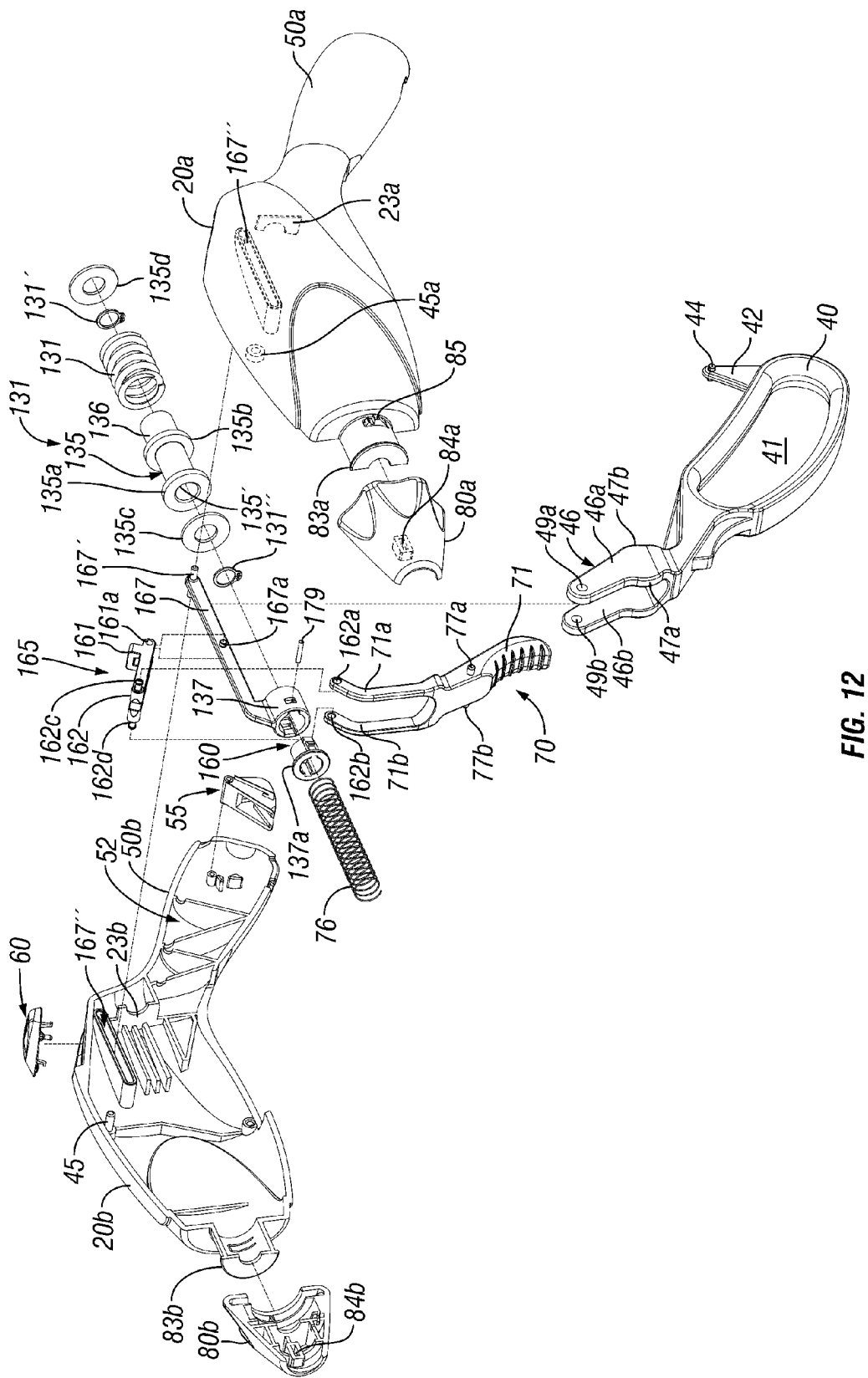
FIG. 12 is an enlarged, exploded perspective view of the housing.

Turning now to the cooperating components of the housing, FIGS. 5A, 5B, 6A, 6B, 11 and 12 show the details of the housing 20 and the component features thereof, namely, the drive assembly 130, the rotating assembly 80, the knife actuating assembly 160, the trigger assembly 70 and the handles 40 and 50. More particularly, FIGS. 5A and 5B show the above-identified assemblies and components in an assembled form in the housing 20 and FIGS. 11 and 12 show an exploded view of each of the above-identified assemblies and components.

As mentioned above and as best shown in FIGS. 11 and 12, the proximal end of shaft 12 is mechanically engaged to the housing 20. Housing 20 is formed from two (2) housing halves 20a and 20b that each include a plurality of interfaces that are dimensioned to mechanically align and engage one another to form housing 20 and enclose the internal working components of forceps 10. As can be appreciated, fixed handle 50 which, as mentioned above, is integrally associated with housing 20, includes halves 50a and 50b that take the shape of handle 50 upon the assembly of the housing halves 20a and 20b.

It is envisioned that a plurality of additional interfaces (not shown) may disposed at various points around the periphery of housing halves 20a and 20b for ultrasonic welding purposes, e.g., energy direction/deflection points. It is contemplated that ultrasonic welding provides better dimensional stability, strength and joint reliability that other, more traditional, methods. For example, the housing halves may be ultrasonically welded utilizing a combination of a primary weld joint using traditional triangular (or similar) energy directors to form a bonded joint coupled with a secondary hard stop surface (removed from the primary joint surface) for preventing over compression of the joint. A tertiary set of alignment pins may be utilized throughout the housing halves 20a and 20b that are configured to both accurately align the halves 20a and 20b during assembly and provide strength and stability during manufacture, handling and transport.

It is also contemplated that housing halves 20a and 20b (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

As best seen in FIGS. 11 and 12, rotating assembly 80 includes two C-shaped halves 80a and 80b which, when assembled, form the rotating assembly 80 which, in turn, house the drive assembly 130 and the knife actuating assembly 160. Half 80a includes a series of detents/flanges (not shown) that are dimensioned to engage a pair of corresponding sockets or other mechanical interfaces (not shown) disposed within rotating half 80b. Half 80a also includes a tab 84a (phantomly illustrated) that together with a corresponding tab 84b disposed on half 80b cooperate to matingly engage slot 80' disposed on shaft 12. As can be appreciated, this permits selective rotation of the shaft 12 about axis "A-A" by manipulating the rotating member 80 in the direction of the arrow "B", which, in turn, rotates the end effector assembly in the direction of arrow "C" (See FIG. 1A). The rotating assembly may include one or more mechanical interfaces that essentially lock the rotating assembly in a fully counter-clock wise rotational position or a fully clockwise rotational position. It is envisioned that this will allow left-handed or right-handed orientations for the end effector assembly for particular users.

As mentioned above and as best illustrated in FIGS. 5A, 5B, 6A and 6B, the movable handle 40 includes clevis 46 that forms upper flanges 46a and 46b that pivot about pins 45a and 45b to pull the reciprocating sleeve 134 along longitudinal axis "A-A" and force driving flanges 47a and 47b against the drive assembly 130 which, in turn, closes the jaw members 110 and 120. The various moving relationships of the flanges 47a and 47b and the drive assembly 130 are explained in more detail below with respect to the operation of the forceps 10. The arrangement of the driving flanges 47a and 47b and the pivot point 45 of the movable handle 40 provides a distinct mechanical advantage over conventional handle assemblies due to the unique position of the pivot pins 45a and 45b (i.e., pivot point) relative to the longitudinal axis "A-A" of the driving flanges 47a and 47b. In other words, by positioning the pivot pins 29a and 29b above the driving flanges 47a and 47b, the user gains lever-like mechanical advantage to actuate the jaw members 110 and 120. This reduces the overall amount of mechanical force necessary to close the jaw members 110 and 120 to affect a tissue seal. A similar mechanical arrangement is disclosed in commonly-owned U.S. patent application Ser. No. 10/460,926 the entire contents of which are incorporated by reference herein.

Handle 40 also includes a finger loop 43 that defines opening 41 that is dimensioned to facilitate grasping the handle 40. In one embodiment, finger loop 43 includes a rubber insert that enhances the overall ergonomic "feel" of the handle member 40. A locking flange 49' is disposed on the outer periphery of the handle member 40 above the finger loop 43. Locking flange 49' may be designed as a safety lock out mechanism to prevent the trigger assembly 70 from firing when the handle member 40 is oriented in a non-actuated position, i.e., the jaw members 110 and 120 are open. As can be appreciated, this would prevent accidental or premature severing of tissue prior to completion of the tissue seal.

Fixed handle 50 includes halves 50a and 50b which, when assembled, form handle 50. Fixed handle 50 includes a channel 51 defined therein that is dimensioned to receive flange 42 in a proximal moving manner when movable handle 40 is actuated. The t-shaped pin 44 of handle 40 is dimensioned for facile reception within channel 51 of handle 50. It is envisioned that flange 42 may be dimensioned to allow a user to selectively, progressively and/or incrementally move jaw members 110 and 120 relative to one another from the open to closed positions. For example, it is also contemplated that flange 42 may include a ratchet-like interface that lockingly engages the movable handle 40 and, therefore, jaw members 110 and 120 at selective, incremental positions relative to one another depending upon a particular purpose. Other mechanisms may also be employed to control and/or limit the movement of handle 40 relative to handle 50 (and jaw members 110 and 120) such as, e.g., hydraulic, semi-hydraulic, linear actuator(s), gas-assisted mechanisms and/or gearing systems.

Figure 5D:
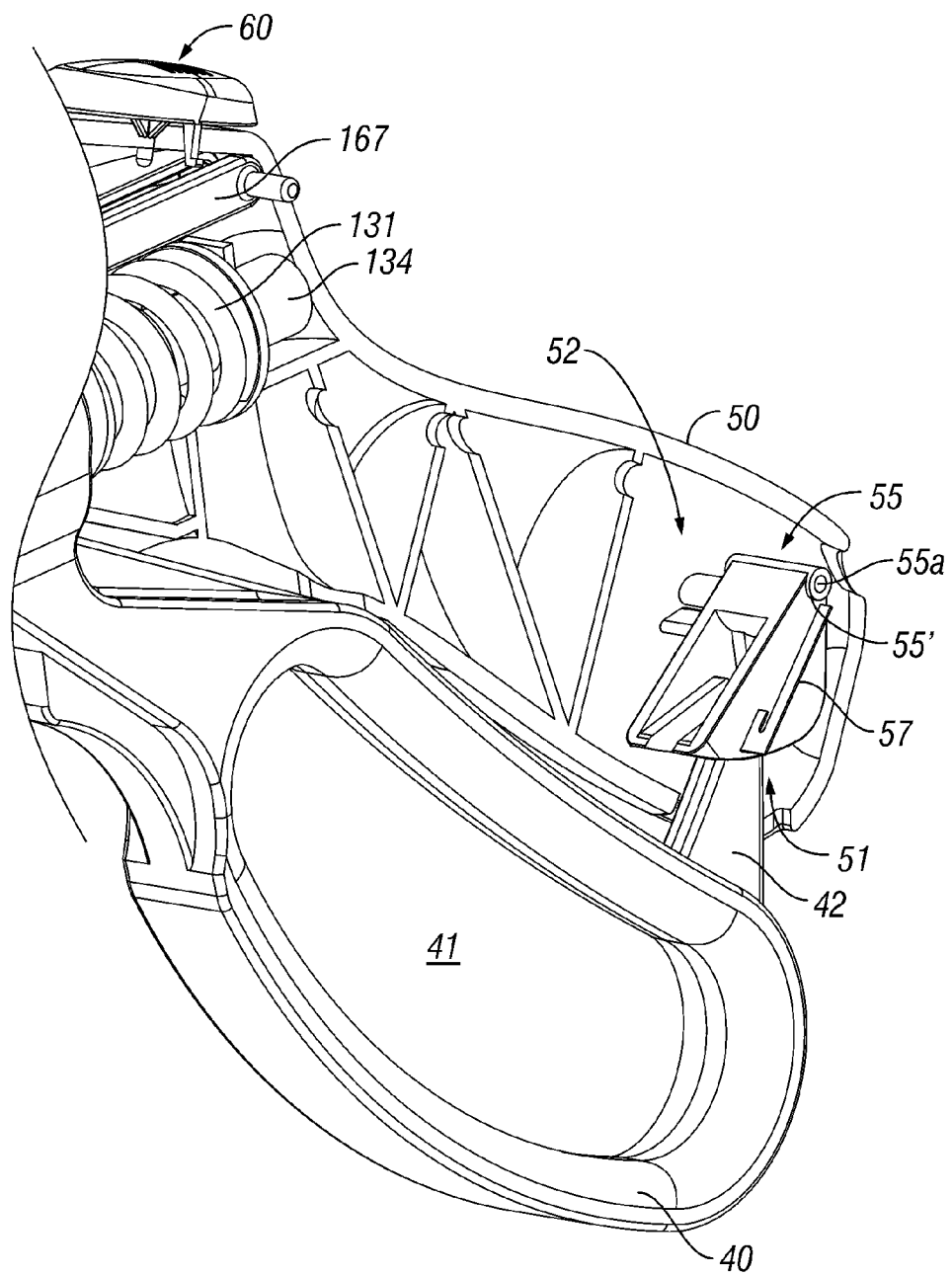
FIG. 5D is a greatly-enlarged, perspective view of the handle assembly in closed configuration.

As best illustrated in FIGS. 5D and 12, housing halves 20a and 20b when assembled form an internal cavity 52 that predefines the channel 51 within fixed handle 50 adjacent the railway 55 that reciprocates t-shaped pin 44 therein. Once assembled, the railway 55 is seated within cavity 52 in registration with entrance pathway 51 for reciprocation of the flange 42. Flange 42 and the housing halves 20a and 20b are designed to facilitate accurate and consistent reception of the t-shaped pin 44 into railway 55.

During movement of the flange 42 along the entrance to channel 51, the t-shaped pin 44 rides through passage 53 along railway 55 and is forced into a catch basin or seat 55' to lock the handle 40 relative to handle 50. When the user releases the handle 40, the catch basin 55' retains the t-shaped pin 44 in a secured position relative to the handle 50 as explained in further detail below. Railway 55 may be seated on one or pivot elements 55a that allows the railway 55 to pivot upon reception of the t-shaped pin 44 therethrough. A spring element 57 biases the railway 55 to return to the original reception position once the t-shaped pin 44 is seated. The railway 55, gain, may pivot in response to release of the t-shaped pin 44 from catch basin 55'. It is envisioned that actuation of the handle 40 along with the inter-cooperating elements of the drive assembly 130 close the jaw members 110 and 120 about tissue with a predeterminable and consistent closure pressure to affect a tissue seal. As mentioned above, closure pressures for sealing large tissue structures preferably fall within the range of about 3 kg/cm$^2$ to about 16 kg/cm$^2$.

When handle 40 is regrasped, the t-shaped pin 44 is forced out of or disengaged from the catch basin 55' and moves along an exit pathway to release handle 40 from channel 51. A spring or other biasing member 57 may be employed to facilitate securing the flange 42 within the catch basin 55' and also configured to facilitate release of the flange 42 from catch basin 55' upon re-grasping of the handle 40.

As explained in more detail below, once actuated, handle 40 moves in a generally arcuate fashion towards fixed handle 50 about pivot pins 45a and 45b that forces driving assembly 130 proximally which, in turn, pulls reciprocating sleeve 134 in a generally proximal direction to close jaw members 110 and 120 relative to one another.

As best shown in FIGS. 5A, 5B and 11, the drive assembly 130 mounts atop the proximal portion of the drive sleeve 134. A pair of retaining rings or clips 131' and 131" (See FIG. 11) cooperate with a corresponding pair of relieved portions 133a and 133b disposed on the drive sleeve 134 to mount the drive assembly 130 atop the drive sleeve 134 such that relative movement of the drive assembly correspondingly moves the drive sleeve 134. As handle 40 pivots about pivot point 45 and moves relative to handle 50 and flange 42 is incorporated into channel 51 of fixed handle 50, the driving flanges 47a and 47b, through the mechanical advantage of the above-the-center pivot point, force the drive assembly 130 proximally against spring 131.

As a result thereof, drive sleeve 134 reciprocates proximally which, in turn, closes the jaw members 110 and 120. It is envisioned that the utilization of an over-the-center pivoting mechanism will enable the user to selectively compress the coil spring 131a specific distance which, in turn, imparts a specific load on the reciprocating sleeve 134 that is converted to a rotational torque about the jaw pivot pin 95. As a result, a specific closure force can be transmitted to the opposing jaw members 110 and 120.

FIGS. 5A and 5B show the initial actuation of handle 40 towards fixed handle 50 that causes the pin 44 of flange 42 to move generally proximally and upwardly along entrance pathway 51. During movement of the flange 42 along the entrance pathway 51, respectively, the t-shaped pin 44 rides through passageway 53 along railway 55 as explained above. Once the desired position for the sealing site is determined and the jaw members 110 and 120 are properly positioned, handle 40 may be compressed fully such that the t-shaped pin 44 of flange 42 seats within catch basin 55'. Once pin 44 clears an edge or passes a predetermined point in the passageway 53 at the edge of the catch basin 55', releasing movement of the handle 40 and flange 42 is redirected into a catch basin 55'.

More particularly, upon a slight reduction in the closing pressure of handle 40 against handle 50, the handle 40 returns slightly distally towards entrance pathway 51 but is re-directed to seat within catch basin 55'. At this point, the release or return pressure between the handles 40 and 50 that is attributable and directly proportional to the release pressure associated with the compression of the drive assembly 130 causes the pin 44 of flange 42 to settle or lock within catch basin 55'. Handle 40 is now secured in position within fixed handle 50 which, in turn, locks the jaw members 110 and 120 in a closed position against the tissue.

As mentioned above, the jaw members 110 and 120 may be opened, closed and rotated to manipulate tissue until sealing is desired. This enables the user to position and re-position the forceps 10 prior to activation and sealing. As illustrated in FIG. 1A, the end effector assembly 100 is rotatable about longitudinal axis "A-A" through rotation of the rotating assembly 80. As explained in more detail below, it is envisioned that the unique feed path of the cable leads 325a and 325b through the rotating assembly 80, along shaft 12 and, ultimately, to the jaw members 110 and 120 enables the user to rotate the end effector assembly 100 about 180 degrees across the clockwise and counterclockwise directions without tangling or causing undue strain on cable leads 325a and 325b. As can be appreciated, this facilitates the grasping and manipulation of tissue.

As best shown in FIGS. 5A, 5B, 6A, 9A, 9B, 11 and 12, trigger assembly 70 mounts atop movable handle 40 and cooperates with the knife assembly 160 to selectively translate knife 190 through a tissue seal. More particularly, the trigger assembly 70 includes a U-shaped finger actuator 71 having a pair upwardly-extending flanges 71a and 71b. A pivot pin 179 extends through a pair of apertures 162a and 162b in each of the flanges 71a and 71b, respectively, to mount the trigger assembly 70 to a knife carriage 165 as explained in more detail below. Finger actuator 71 is selectively pivotable within a pre-defined slot 21 disposed within housing 20 (See FIG. 6A). More particularly, a pair of pivots 77a and 77b is disposed on either side of the finger actuator 71 and are configured to mount between housing halves 20a and 20b to pivot the finger actuator within slot 21.

The knife assembly 160 includes a reciprocating knife bar 167 that mounts atop the drive sleeve 134 and between upwardly extending flanges 71a and 71b. Knife bar 167 includes a t-shaped proximal end 167' and a cuff 137 disposed at the distal end thereof. Cuff 137 is dimensioned to encapsulate drive sleeve 134 when the knife assembly 160 is assembled. A spring 76 biases the cuff in a proximal-most orientation. Proximal end 167' is dimensioned to mount and slidingly reciprocate within a slot 167" formed by housings 20a and 20b at assembly (See FIG. 12). A locking cap 137a and a mounting pin 179 secure the cuff 137 to the proximal end 193b of the knife rod 193 through aperture 197 disposed therein such that proximal movement to the finger actuator 71 results in distal movement of the knife bar 193. Cuff 137 and cap 137a also allow 360 degrees of rotation of the drive sleeve 134 therethrough.

As mentioned above, a knife carriage 165 mounts to the upwardly extending flanges 71a and 71b of the finger actuator 71. More particularly, the distal end 162 of the knife carriage 165 is t-shaped and includes two laterally extending pins 162c and 162d that engage apertures 162a and 162b, respectively, in flanges 71a and 71b. The proximal end 161 of the knife carriage 165 includes an aperture 161a defined therein that mates with a detent 167a that extends transversally through knife carriage 165.

As best illustrated in FIGS. 5A-7, when the handle 40 is disposed in a spaced-apart or open configuration relative to handle 50, flange 49' that extends from handle 40 prevents actuation of the trigger assembly 70. More particularly, finger actuator 71 is prevented from being actuated proximally by flange 49' when the jaw members 110 and 120 are open. As can be appreciated, this prevents premature actuation of the knife 190 when tissue is not grasped between jaw members 110 and 120. When handle 40 is selectively moved relative to handle 50, a gap 21 is formed between the flange 49' and the finger actuator 71 (See FIG. 5B). Thus, the user is free to selectively actuate the knife 190 by squeezing the finger actuator 71 proximally within gap 21.

Figure 6A:
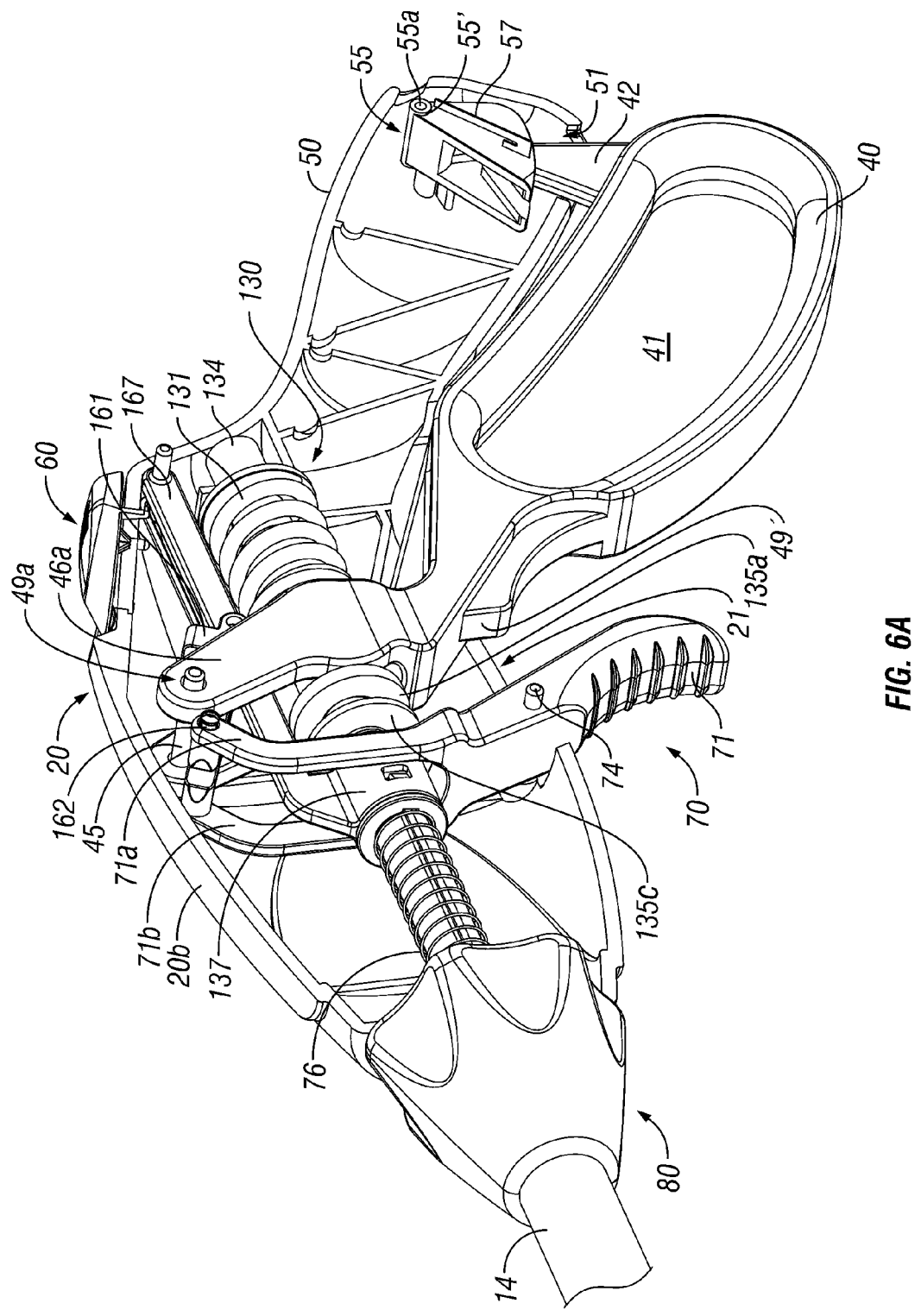
FIG. 6A is an internal, perspective view of the endoscopic forceps of FIG. 1B with the internal working components of the forceps exposed and the trigger shown in an un-actuated position.
Figure 6B:
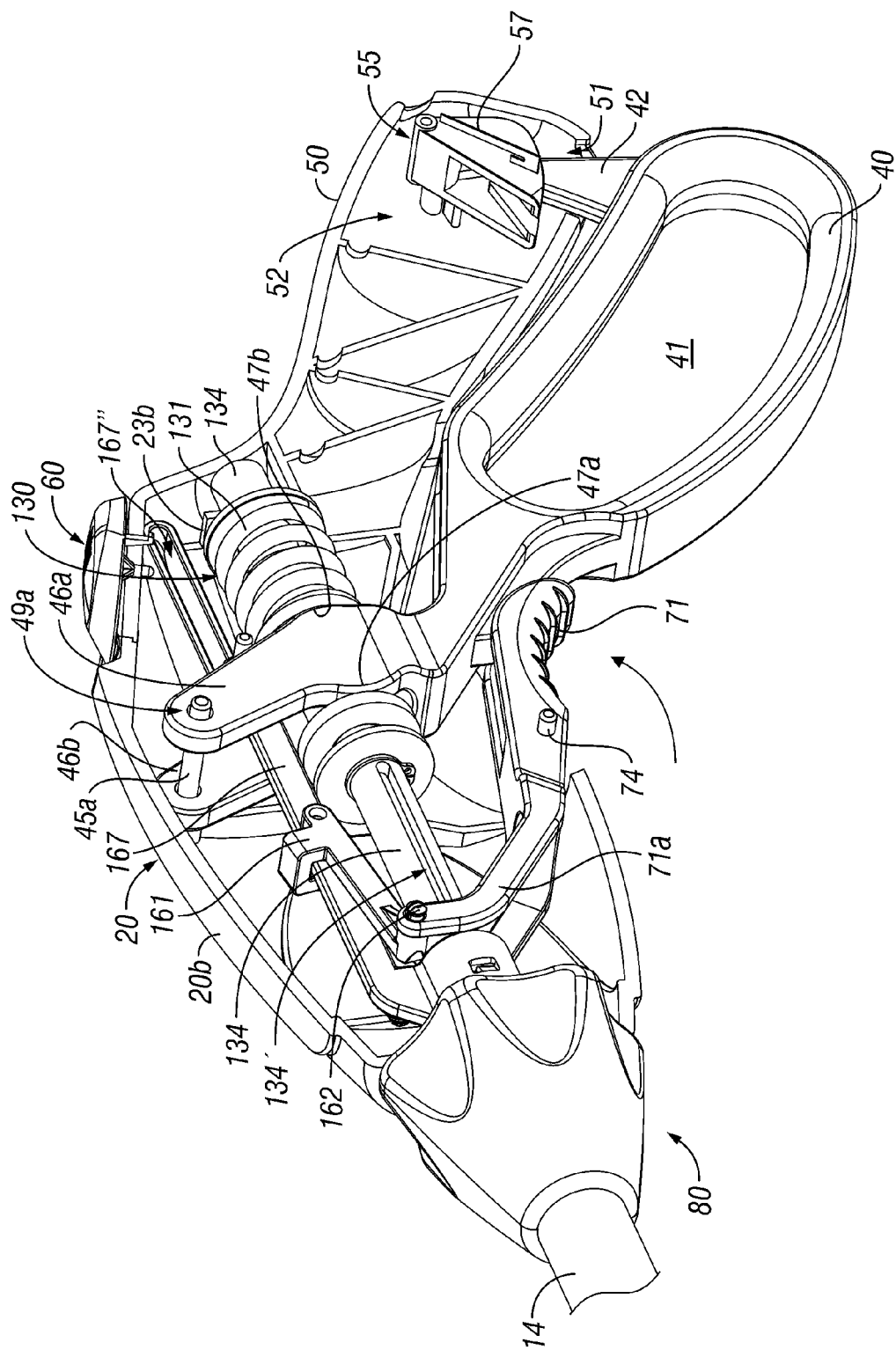
FIG. 6B is an internal, perspective view of the endoscopic forceps of FIG. 1B with the internal working components of the forceps exposed and the trigger shown in an actuated position.
Figure 6C:
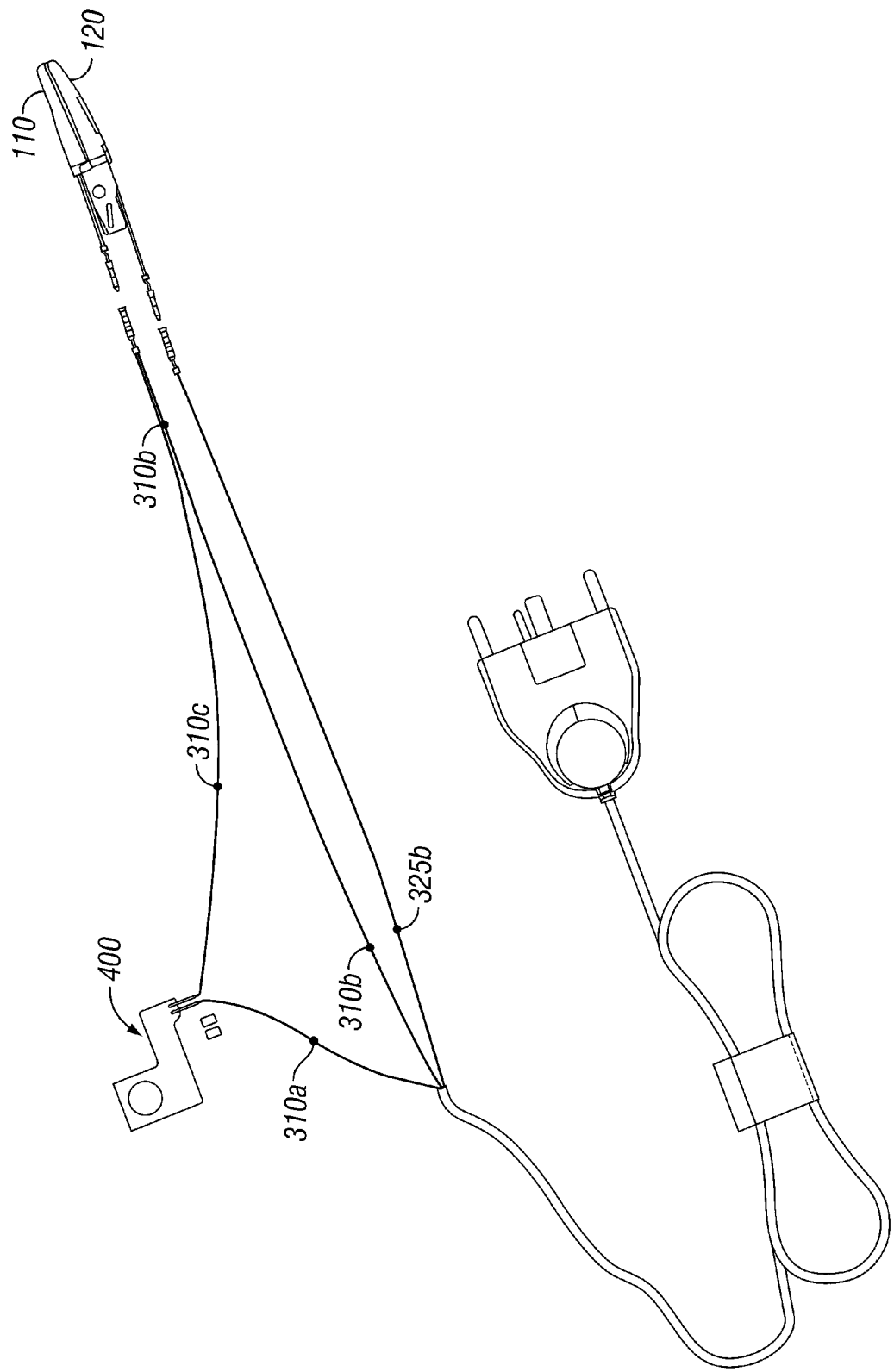
FIG. 6C is a schematic representation of the electrical configuration for the trigger assembly.
Figure 7:
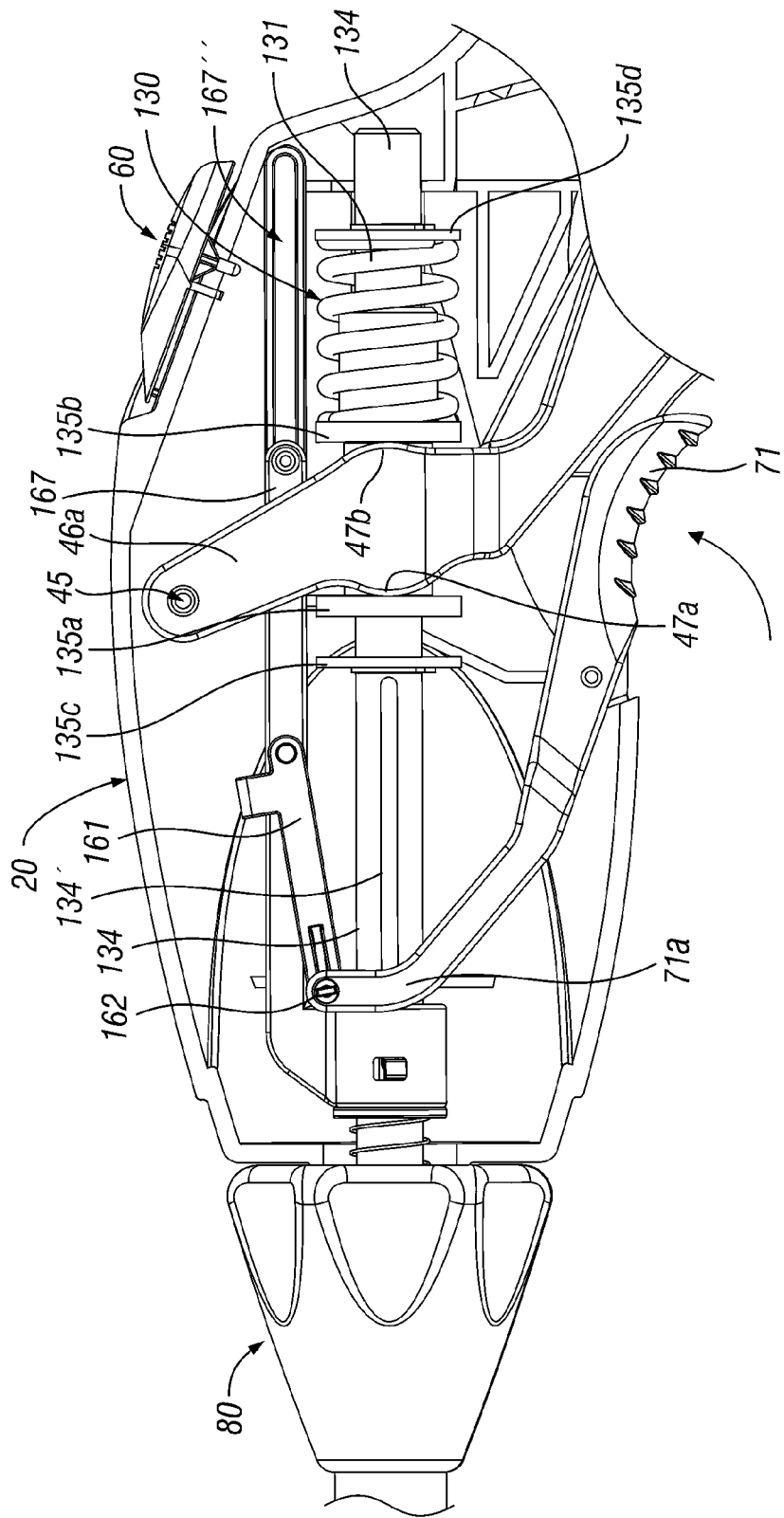
FIG. 7 is an internal, side view of the endoscopic forceps of FIG. 1B with the trigger shown in an actuated position.
Figure 8A:
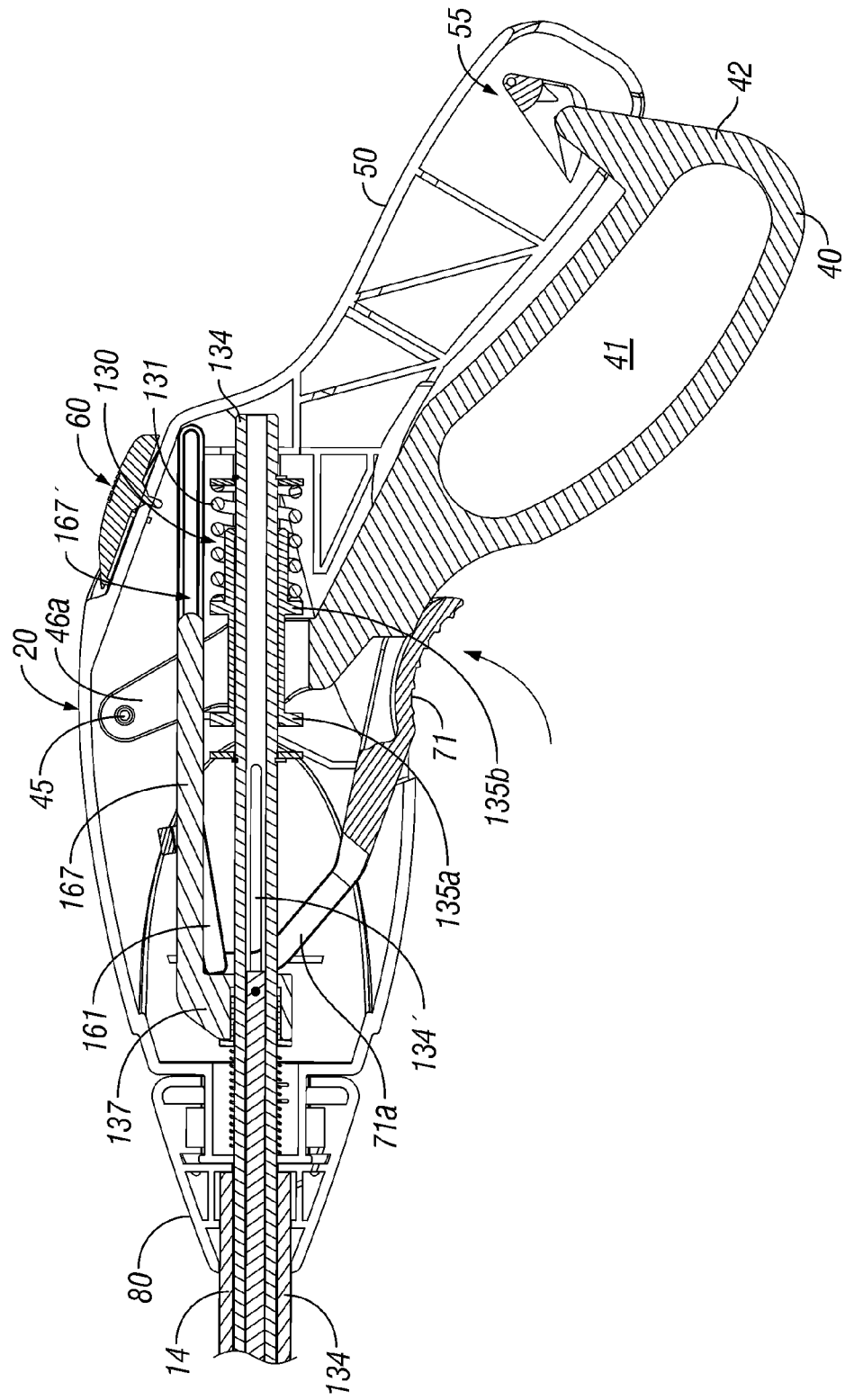
FIG. 8A is a side cross-sectional view showing the trigger in an actuated position.
Figure 9A:
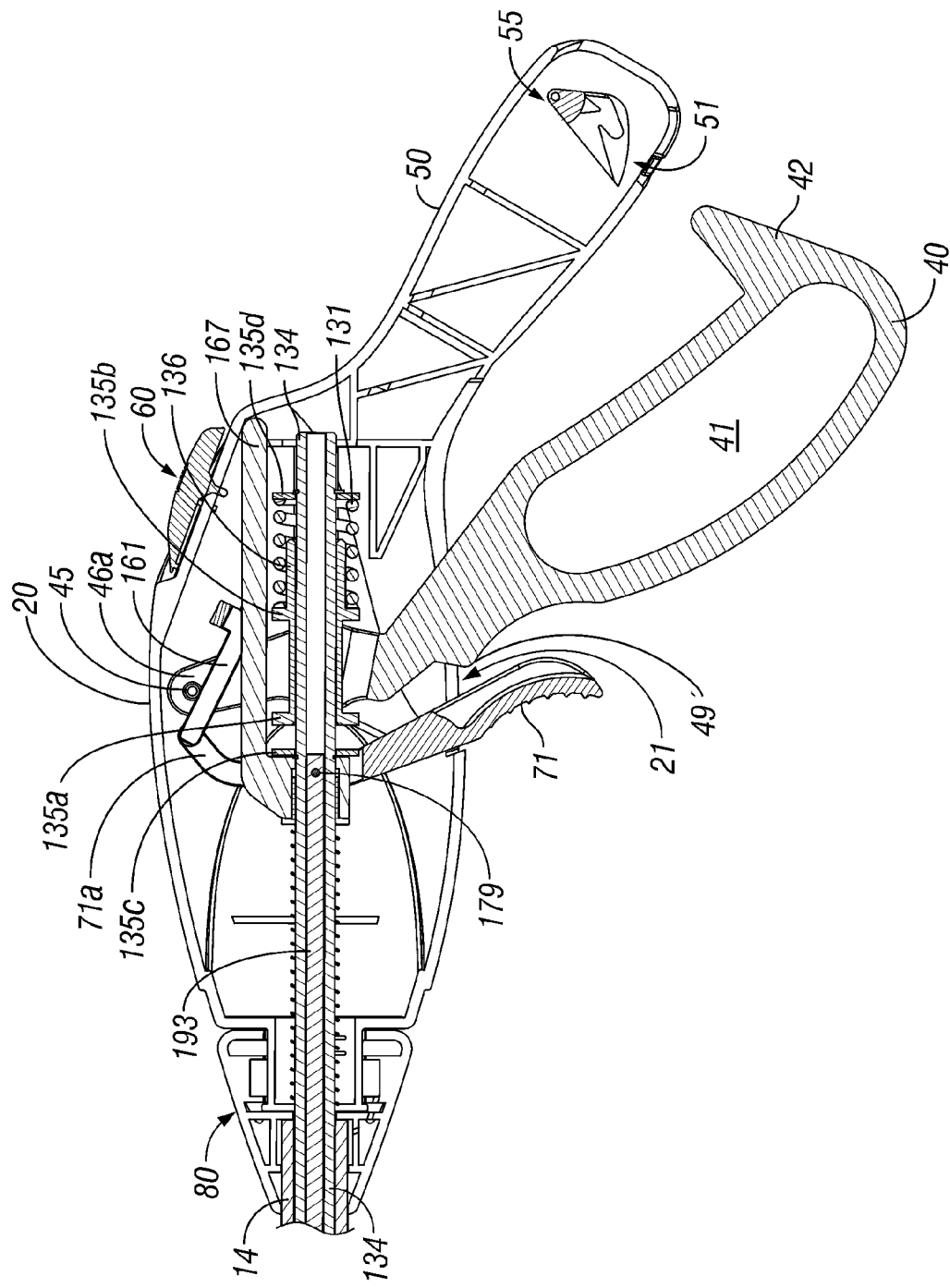
FIG. 9A is side cross-sectional view of the housing showing both the trigger and the handle un-actuated.
Figure 9B:
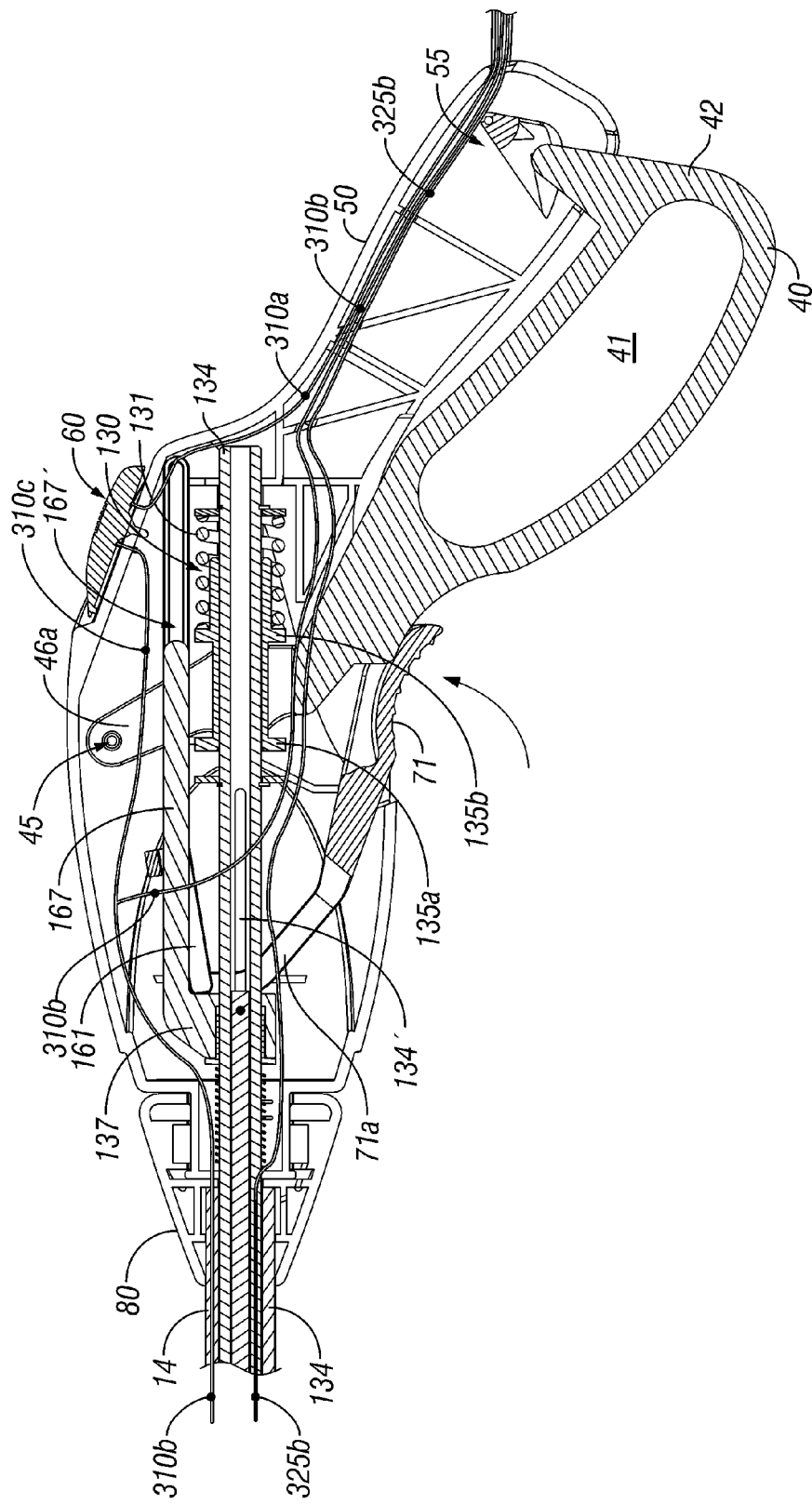
FIG. 9B is side cross-sectional view of the housing showing both the trigger and the handle actuated.
Figure 10A:
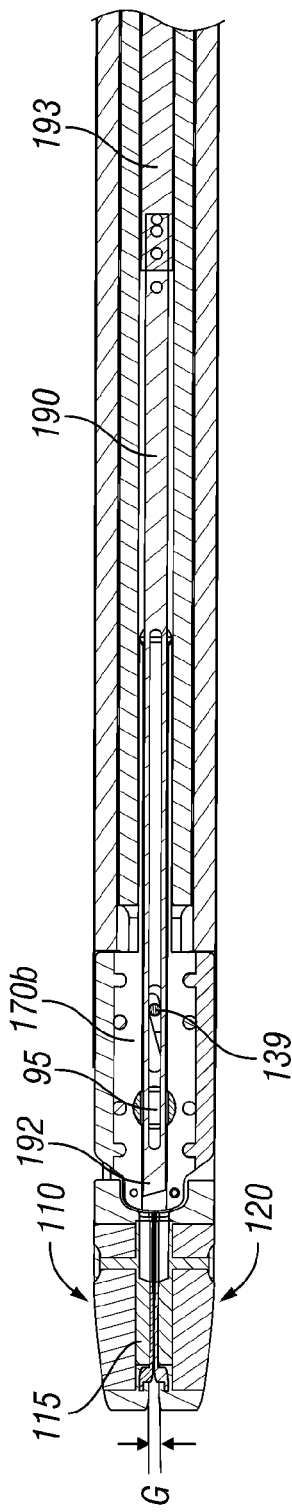
FIG. 10A is an enlarged, side cross-sectional view showing the end effector in a closed position and the knife in an unactuated position.
Figure 10B:
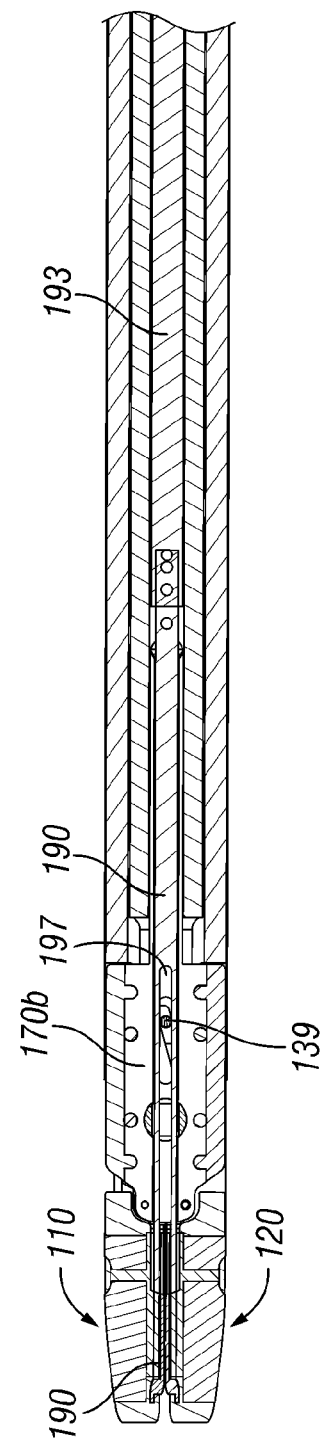
FIG. 10B is an enlarged, side cross-sectional view showing the end effector in a closed position and the knife in an actuated position.
Figure 10C:
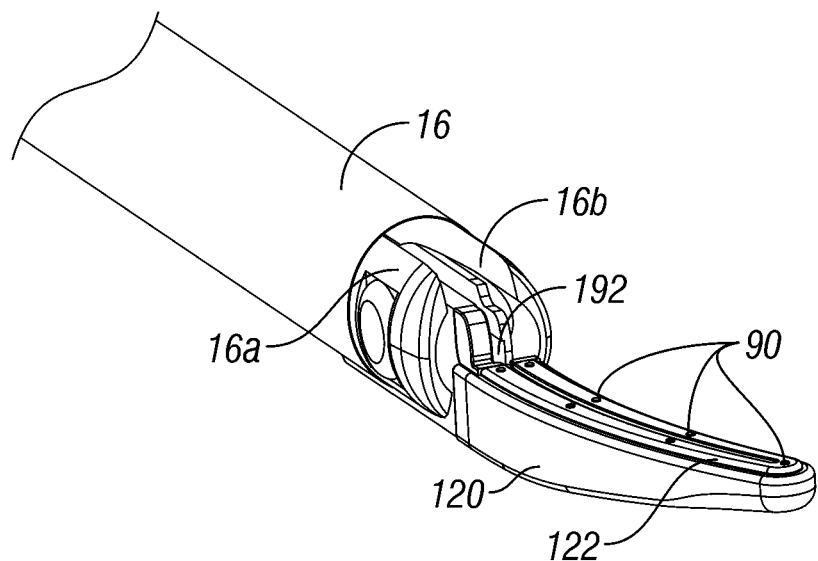
FIG. 10C is an enlarged, front perspective view of a bottom jaw member of the end effector assembly showing the knife in an unactuated position.
Figure 10D:
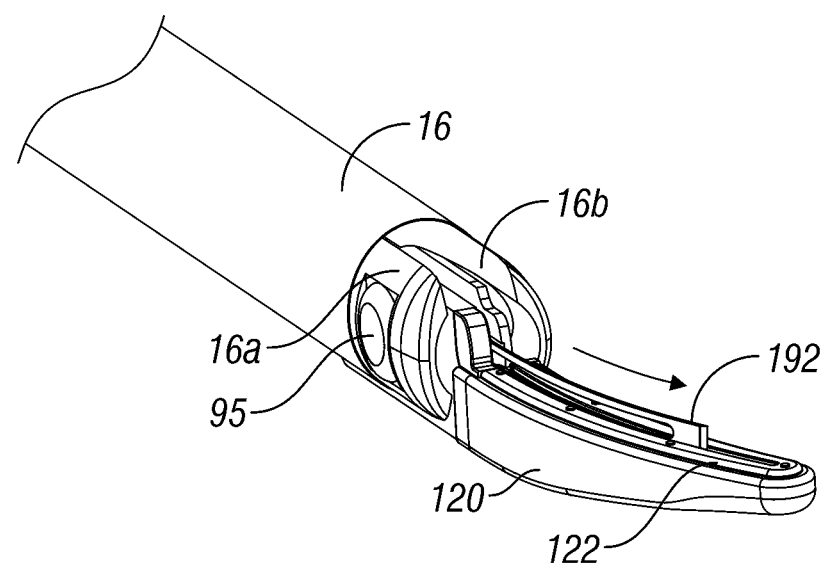
FIG. 10D is an enlarged, front perspective view of the bottom jaw member showing the knife in an actuated position.

As best shown in FIGS. 6B, 7 and 8A, once the clearance is provided by movement of handle 40, proximal movement of the finger actuator 71 about pivot 74 results in distal translation of the knife bar 167 which, in turn, results in distal translation of the knife rod 193 and knife 190. More particularly, when finger actuator 71 is squeezed proximally, the U-shaped flanges 71a and 71b rotate about pivot 74 to abut cuff 137 and essentially throw the knife carriage 165 forward which, in turn, carries the knife bar 167 forward to force the knife rod 193 distally. Slot 167" is configured to smoothly guide the knife bar 167 distally through the forward and return stroke. As shown in FIGS. 10A and 10BC, distal translation of the knife rod 193 translates the knife 190 through channel 115 in the jaw members 110 and 120. As mentioned above, the knife rod 193 mounts the knife 190 via one or more mechanically interfacing elements or may be affixed in any known manner in the art. A slot 197 defined within the knife 190 provides clearance for pin 139 of the drive sleeve 134 during reciprocation of the knife 190. Upon release of finger actuator 71, spring 76 biases the knife assembly back to a proximal-most position. It is envisioned that the knife bar 167 provides variable mechanical advantage and linear advantage when triggering the knife 190. In addition, the incorporation of the knife bar 167 significantly reduces friction loss and provides smoother mechanical cutting than previously known methods.

Turning now in detail to the operation of the drive assembly as best seen in FIGS. 5A, 5B, 11 and 12, drive assembly 130 includes reciprocating sleeve 134, drive housing 135, spring 131, drive rings 135a and 135b, drive stops 135c and 135d and retaining rings 131' and 131" that all cooperate to form the drive assembly 130. It is envisioned that stop 135c may be removed and ring 131" would perform stop 135c's intended function. The proximal end 132 of the reciprocating sleeve 134 is positioned within an aperture 135' defined through the drive housing 135 to permit selective reciprocation of the drive sleeve 134 therethrough upon actuation of the movable handle 40. The spring 131 is assembled atop the drive housing 135 between a rear stop 135d and ring 135b such that movement handle 40 about pivot 45 moves the entire drive assembly 130 and sleeve 134 proximally which, in turn, pulls cam pin 139 proximally to close the jaw members 110 and 120. Once the jaw members 110 and 120 close about tissue, the drive assembly 130 essentially bottoms out (i.e., further proximal movement of the reciprocating sleeve is prevented) and further movement of handle 40 about pivot 45 compresses spring 131 resulting in additional closure force on the tissue. Moreover, spring 131 also tends to bias the jaw members 110 and 120 and the movable handle 40 in an open configuration.

Turning back to FIG. 12 that shows the exploded view of the housing 20, rotating assembly 80, trigger assembly 70, movable handle 40 and fixed handle 50, it is envisioned that all of these various component parts along with the shaft 12 and the end effector assembly 100 are assembled during the manufacturing process to form a partially and/or fully disposable forceps 10. For example and as mentioned above, the shaft 12 and/or end effector assembly 100 may be disposable and, therefore, selectively/releasably engageable with the housing 20 and rotating assembly 80 to form a partially disposable forceps 10 and/or the entire forceps 10 may be disposable after use.

As best seen in FIGS. 5A, 5B and 13, once assembled, spring 131 is poised for compression atop drive housing 135 upon actuation of the movable handle 40. More particularly, movement of the handle 40 about pivot pins 45a and 45b reciprocates the flange 42 into fixed handle 50 and forces drive assembly 130 to compress spring 131 against the rear stop 135d to reciprocate the sleeve 134.

As mentioned above, the trigger assembly 70 is initially prevented from firing by the locking flange 49' disposed on movable handle 40 that abuts against the trigger assembly 70 prior to actuation. It is envisioned that the opposing jaw members 110 and 120 may be rotated and partially opened and closed without unlocking the trigger assembly 70 which, as can be appreciated, allows the user to grip and manipulate the tissue without premature activation of the knife assembly 160. As mentioned below, only when the t-shaped pin 44 of flange 42 is completely reciprocated within channel 51 of the fixed handle 50 and seated within pre-defined catch basin 55' will the locking flange 49' allow full activation of the trigger assembly 70. The operating features and relative movements of these internal working components of the forceps 10 are shown by phantom representation and directional arrows and are best illustrated in the various figures.

It is envisioned that the mechanical advantage of the over-the-center pivot will enable the user to selectively compress the coil spring 131a specific distance which, in turn, imparts a specific load on the reciprocating sleeve 134. The reciprocating sleeve's 134 load is converted to a torque about the jaw pivot 95. As a result, a specific closure force can be transmitted to the opposing jaw members 110 and 120. As mentioned above, the jaw members 110 and 120 may be opened, closed and rotated to manipulate tissue until sealing is desired without unlocking the trigger assembly 70. This enables the user to position and re-position the forceps 10 prior to activation and sealing. More particularly, as illustrated in FIG. 1A, the end effector assembly 100 is rotatable about longitudinal axis "A-A" through rotation of the rotating assembly 80.

Once the desired position for the sealing site is determined and the jaw members 110 and 120 are properly positioned, handle 40 may be compressed fully such that the t-shaped pin 44 of flange 42 clears a pre-defined railway edge located atop the railway 55. Once end 44 clears the railway edge, the end 44 is directed into catch basin 55' to lock the handle 40 relative to handle 50. The release or return pressure between the handles 40 and 50 that is attributable and directly proportional to the release pressure associated with the compression of the drive assembly 130 causes the end 44 of flange 42 to settle or lock within catch basin 55'. Handle 40 is now secured in position within fixed handle 50 which, in turn, locks the jaw members 110 and 120 in a closed position against the tissue.

At this point the jaws members 110 and 120 are fully compressed about the tissue. Moreover, the forceps 10 is now ready for selective application of electrosurgical energy and subsequent separation of the tissue, i.e., as t-shaped end 44 seats within catch basin 55', locking flange 49' moves into a position to permit activation of the trigger assembly 70.

As the t-shaped end 44 of flange 42 seats within catch basin 55', a proportional axial force on the reciprocating sleeve 134 is maintained which, in turn, maintains a compressive force between opposing jaw members 110 and 120 against the tissue. It is envisioned that the end effector assembly 100 and/or the jaw members 110 and 120 may be dimensioned to off-load some of the excessive clamping forces to prevent mechanical failure of certain internal operating elements of the end effector 100.

As can be appreciated, the combination of the mechanical advantage of the over-the-center pivot along with the compressive force associated with the compression spring 131 facilitate and assure consistent, uniform and accurate closure pressure about the tissue within the desired working pressure range of about 3 kg/cm$^2$ to about 16 kg/cm$^2$ and, desirably, about 7 kg/cm$^2$ to about 13 kg/cm$^2$. By controlling the intensity, frequency and duration of the electrosurgical energy applied to the tissue, the user can treat tissue, i.e., seal tissue.

As mentioned above, two mechanical factors play an important role in determining the resulting thickness of the sealed tissue and effectiveness of the seal, i.e., the pressure applied between opposing jaw members 110 and 120 and the gap distance "G" between the opposing sealing surfaces 112, 122 of the jaw members 110 and 120 during the sealing process. However, thickness of the resulting tissue seal cannot be adequately controlled by force alone. In other words, too much force and the two jaw members 110 and 120 would touch and possibly short resulting in little energy traveling through the tissue thus resulting in a bad tissue seal 450. Too little force and the seal would be too thick.

Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness that is an indication of a good seal.

In one embodiment, the electrically conductive sealing surfaces 112 and 122 of the jaw members 110 and 120, respectively, are relatively flat to avoid current concentrations at sharp edges and to avoid arcing between high points. In addition and due to the reaction force of the tissue when engaged, jaw members 110 and 120 can be manufactured to resist bending. For example, the jaw members 110 and 120 may be tapered along the width thereof that is advantageous for two reasons: 1) the taper will apply constant pressure for a constant tissue thickness at parallel; 2) the thicker proximal portion of the jaw members 110 and 120 will resist bending due to the reaction force of the tissue.

As mentioned above, at least one jaw member, e.g., 120, may include one or more stop members 90 that limit the movement of the two opposing jaw members 110 and 120 relative to one another. In one embodiment, the stop members 90 extend from the sealing surface 122 a predetermined distance according to the specific material properties (e.g., compressive strength, thermal expansion, etc.) to yield a consistent and accurate gap distance "G" during sealing (FIG. 10B). It is envisioned for the gap distance between opposing sealing surfaces 112 and 122 during sealing ranges from about 0.001 inches to about 0.006 inches and, desirably, between about 0.002 and about 0.005 inches. In one embodiment, the non-conductive stop members 90 are molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 90. Several thermal spraying techniques are contemplated that involve depositing a broad range of heat resistant and insulative materials on various surfaces to create stop members 90 for controlling the gap distance between electrically conductive surfaces 112 and 122.

As energy is being selectively transferred to the end effector assembly 100, across the jaw members 110 and 120 and through the tissue, a tissue seal forms isolating two tissue halves. At this point and with other known vessel sealing instruments, the user may remove and replace the forceps 10 with a cutting instrument (not shown) to divide the tissue halves along the tissue seal. As can be appreciated, this is both time consuming and tedious and may result in inaccurate tissue division across the tissue seal due to misalignment or misplacement of the cutting instrument along the ideal tissue cutting plane.

As explained in detail above, the present disclosure incorporates knife assembly 160 which, when activated via the trigger assembly 70, progressively and selectively divides the tissue along an ideal tissue plane in a precise manner to effectively and reliably divide the tissue into two sealed halves. The knife assembly 160 allows the user to quickly separate the tissue immediately after sealing without substituting a cutting instrument through a cannula or trocar port. As can be appreciated, accurate sealing and dividing of tissue is accomplished with the same forceps 10.

It is envisioned that knife blade 190 may also be coupled to the same or an alternative electrosurgical energy source to facilitate separation of the tissue along the tissue seal. Moreover, it is envisioned that the angle of the trip of the knife blade 190 may be dimensioned to provide more or less aggressive cutting angles depending upon a particular purpose. For example, the knife blade 190 may be positioned at an angle that reduces "tissue wisps" associated with cutting. Moreover, the knife blade 190 may be designed having different blade geometries such as serrated, notched, perforated, hollow, concave, convex etc. depending upon a particular purpose or to achieve a particular result. It is envisioned that the knife assembly 160 generally cuts in a progressive, uni-directional fashion (i.e., distally).

Once the tissue is divided into tissue halves, the jaw members 110 and 120 may be opened by re-grasping the handle 40 as explained below. Re-initiation or re-grasping of the handle 40 again moves t-shaped pin 44 of flange 42 generally proximally.

As best shown in FIG. 13, the proximal portions of the jaw members 110 and 120 and the distal end 16 of shaft 12 may be covered by a resilient or flexible insulating material 185 to reduce stray current concentrations during electrosurgical activation. An insulating boot (not shown) may also be positioned atop the proximal portions of the jaw members 110 and 120 to further reduce current concentrations and stray currents from damaging adjacent tissue. Details relating to one envisioned insulating boot 220 are described with respect to commonly-owned U.S. Provisional Application Ser. No. 60/722,213 entitled "INSULATING BOOT FOR ELECTROSURGICAL FORCEPS", the entire contents of which being incorporated by reference herein.

Switch 60 is ergonomically dimensioned and conforms to the outer shape of housing 20 (once assembled). Switch 60 is designed to electromechanically cooperate with a flex circuit 400 (See FIG. 6C) to allow a user to selectively activate the jaw members 110 and 120. It is contemplated that a flex circuit design facilitates manufacturing due to the circuit unique ability to conform as needed into tightly spaced areas. It is also envisioned that the switch 60 permits the user to selectively activate the forceps 10 in a variety of different orientations, i.e., multi-oriented activation or toggle-like activation. As can be appreciated, this simplifies activation. It is envisioned that switch 60 may also be designed as a so called "dome switch" that also provides tactile feedback to the user when activated.

When switch 60 is depressed, trigger lead 310b carries the first electrical potential to jaw member 110 thus completing a bipolar circuit. More particularly, when switch 60 is depressed and flex circuit 400 is activated, the generator recognizes a voltage drop across leads 310a and 310c that initiates activation of the generator to supply a first electrical potential to jaw member 110 and a second electrical potential to jaw member 120. Switch 60 acts as a control circuit and is protected or removed from the actual current loop that supplies electrical energy to the jaw members 110 and 120. This reduces the chances of electrical failure of the switch 60 due to high current loads during activation. A footswitch (not shown) that may also be utilized with the forceps 10, also operates in a similar manner, i.e., upon activation of the footswitch, the generator recognizes a voltage drop across the input and output leads of the footswitch which, in turn, signals the generator to initiate electrosurgical activation of the jaw members 110 and 120.

It is envisioned that a safety switch or circuit (not shown) may be employed such that the switch cannot fire unless the jaw members 110 and 120 are closed and/or unless the jaw members 110 and 120 have tissue held therebetween.

In the latter instance, a sensor (not shown) may be employed to determine if tissue is held therebetween. In addition, other sensor mechanisms may be employed that determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

The jaw members 110 and 120 are electrically isolated from one another such that electrosurgical energy can be effectively transferred through the tissue to form seal. The cable leads 310b and 325b are held loosely but securely along the cable path to permit rotation of the jaw members 110 and 120 about longitudinal axis "A" (See FIG. 1A). More particularly, cable leads 310b and 325b are fed through respective halves 80a and 80b of the rotating assembly 80 in such a manner to allow rotation of the shaft 12 (via rotation of the rotating assembly 80) in the clockwise or counter-clockwise direction without unduly tangling or twisting the cable leads 310b and 325b. The presently disclosed cable lead feed path is envisioned to allow rotation of the rotation assembly approximately 180 degrees in either direction.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

It is also contemplated that the forceps 10 (and/or the electrosurgical generator used in connection with the forceps 10) may include a sensor or feedback mechanism (not shown) that automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

Moreover, it is contemplated that the trigger assembly 70 may include other types of recoil mechanism that are designed to accomplish the same purpose, e.g., gas-actuated recoil, electrically-actuated recoil (i.e., solenoid), etc. It is also envisioned that the forceps 10 may be used to cut tissue without sealing. Alternatively, the knife assembly 70 may be coupled to the same or alternate electrosurgical energy source to facilitate cutting of the tissue.

It is envisioned that the outer surface of the end effector assembly 100 may include a nickel-based material, coating, stamping, metal injection molding that is designed to reduce adhesion between the jaw members 110 and 120 with the surrounding tissue during activation and sealing. Moreover, it is also contemplated that the conductive surfaces 112 and 122 of the jaw members 110 and 120 may be manufactured from one (or a combination of one or more) of the following materials: nickel-chrome, chromium nitride, MedCoat 2000 manufactured by The Electrolizing Corporation of OHIO, inconel 600 and tin-nickel. The tissue conductive surfaces 112 and 122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings that include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

As can be appreciated, locating the switch 60 on the forceps 10 has many advantages. For example, the switch 60 reduces the amount of electrical cable in the operating room and eliminates the possibility of activating the wrong instrument during a surgical procedure due to "line-of-sight"

activation. Moreover, it is also envisioned that the switch 60 may be configured such that it is mechanically or electromechanically decommissioned during trigger activation to eliminate unintentionally activating the device during the cutting process. It is also envisioned that the switch 60 may be disposed on another part of the forceps 10, e.g., the fixed handle 50, rotating assembly 80, housing 20, etc.

It is also envisioned that the forceps 10 may be equipped with an automatic, electro-mechanical release mechanism (not shown) that releases the tissue once an end seal is determined (i.e., end-tone signal from the generator). For example, an electromechanical interface may be configured to automatically release the t-shaped pin 44 from catch basin 55 upon an end tone condition.

It is also contemplated that the forceps 10 may be dimensioned to include a trigger assembly 70 that operates in lieu of the switch assembly 60 to activate the forceps to seal tissue while also advancing the knife 190 to divide the tissue across the seal. For example, the trigger assembly 70 could be configured to have two stages: a first or initial stroke stage that activates the generator to selectively seal tissue; and a second or subsequent stage that advances the knife through the tissue. Alternatively, another embodiment may include a trigger assembly that simultaneously activates the jaw members 110 and 120 to seal tissue and advances the knife 190 through the tissue during activation.

It is also envisioned that the rotating assembly 80 may be equipped with one or more mechanical interfaces that are rotatable with or within the rotating assembly 80 and that are configured to produce tactile and/or audible feedback to the user during rotation. The tactile and/or audible feedback (i.e., a "click") may be configured to correspond to a particular degree of rotation of the end effector assembly 100 about the axis "A". It is also contemplated that one or more types of visual indicia may also be employed with the rotating assembly 80 to correspond to the amount or degree of rotation of the end effector assembly 100 and may be designed correspond to or relate to the audible and/or tactile feedback depending upon a particular purpose.

Another envisioned version of the forceps 10 may include a telescoping shaft that allows the user to selectively regulate the length of the instrument for particular surgical purposes. For example, it is envisioned that the shaft may include two slidingly reciprocatable and extendible elements that upon exertion (i.e., pulling, twisting, or by virtue of a mechanical lever on the handle) either lengthen or shorten the size of the elongated shaft 12 depending upon a particular surgical purpose.

Moreover, it is also contemplated that the diameter of shaft 12 may be selectively expandable depending upon a particular surgical purpose or to provide rigidity of the forceps 10 inside the surgical cavity or to enhance the sealing effect of the shaft through a trocar. More particularly, it is contemplated that the shaft 12 may be configured to expand upon exertion (i.e., twisting or rotating one element inside another (iris-like), sliding a mechanical lever, an inflatable system, a mechanically expanding system or other types of known expansion systems). As a result, the surgeon can selectively expand the outer diameter of the shaft 12 to enhance the rigidity of the shaft 12 within a trocar and/or enhance the sealing effect of the shaft 12 within the trocar to reduce the possibility of pressure leakage from surgical cavity during use. Moreover, a single forceps may be selectively adaptable to work with differently-sized trocars and/or cannulas that may prove advantageous for particular operations and other surgical procedures.

It is also contemplated that the forceps 10 may be configured such that handle 50 is selectively replaceable or selectively positionable depending upon user preference. For example, handle 50 may be selectively detached and replaced with another handle 50 that is of different dimension (i.e., size, weight, angle, orientation to user's hand, etc.) that facilitates handling during surgical procedures. Alternatively, handle 50 may be selectively positionable relative to the housing 20 (i.e., the angle of the handle to the housing is adjustable) to facilitate handling and use during particular surgical procedures or for user comfort.

It is also envisioned that the forceps may be configure to include a visual indicator (which cooperates with the "end tone" indicator on the generator) to provide visual confirmation of a successful seal (e.g., a green LED indicator). The visual indicator (not shown) may be employed on or in connection with the end effector assembly 100 or shaft 12 that is in line-of-site of the surgeon during use. The visual indicator may also be designed to warn the user of a mis-seal condition or a re-grasp condition (e.g., a red LED indicator). Alternatively, the visual indicator may also be configured to provide progressive feedback of the formation of the seal during the sealing process. For example, a series of LEDs may be employed on the end effector assembly 100 (or shaft 12) that progressively illuminate through the sealing process to provide visual feedback to the user regarding the status of the seal. Moreover, it is envisioned that one or both jaw members may include visual markings that indicate the end of a seal and/or the length of the seal cut.

It is also envisioned that the guide element 170 (See FIG. 14) may be configured to not only guide the knife 190 into the knife channel 115 disposed between the jaw members 110 and 120, but may also be dimensioned to precisely space the jaw members 110 and 120 relative to one another about the pivot 95. Moreover, the guide element 170 may be configured to include one or more grooves of tracks (not shown) to guide the electrical connections or wires 310b and 325b through the end effector assembly 100. The guide element 170 may also be configured to limit the distal movement of the drive rod 193 for the knife 190 which, in turn, limits the overall travel of the knife 190 through the knife channel 115.

It is also contemplated that the stem 95a of the pivot pin 95 may include a stepped diameter that securely compresses the jaw members 110 and 120 together when mechanically secured with the cap 95b. Moreover, the pivot may be dimensioned to include a pass through or aperture 96 that allows translation of the knife therethrough. The two-piece pivot 95 including stem 95a and cap 95b may be assembled during the manufacturing process by any one of several known manufacturing techniques including: laser or heat-based welding, press-fit mechanical interaction (or other mechanically interlocking geometry, adhesives, chemical bonding, etc.

It is also envisioned that the shaft may be dimensioned to enhance visibility and/or non-symmetric depending upon a particular purpose. For example, it is contemplated that the shaft may be generally oval in dimension thereby providing uni-directional strength in one dimension versus another and maximized visibility to the operating site in one direction versus another. Alternatively, the shaft may be other geometric configurations depending upon a particular purpose, I-beam, square, polygonal, etc.

It is also envisioned that the end effector assembly 100 is optimized for reengaging long tissue sections and visibility of the operating site. The jaw members 110 and 120 may also be dimensioned to include distal ends configured for gross or blunt dissection.

The inclusion of a knife blade in bipolar forceps has been problematic in that it is difficult to provide a knife blade having enough flexibility to move within a knife slot channel curve while being resistant to buckling during activation. Further, it has been difficult to design a knife blade that does not add to the overall height of the front profile of the forceps, and/or is pre-disposed within the structural jaw of the forceps prior to activation. Moreover, it has been problematic to design a knife blade durable enough to cut tissue while having the ability to go around or through the cam pin. It is envisioned that these design features are now obtainable by providing a knife blade 190 having specific parameters in accordance with the present disclosure.

Figure 15A:
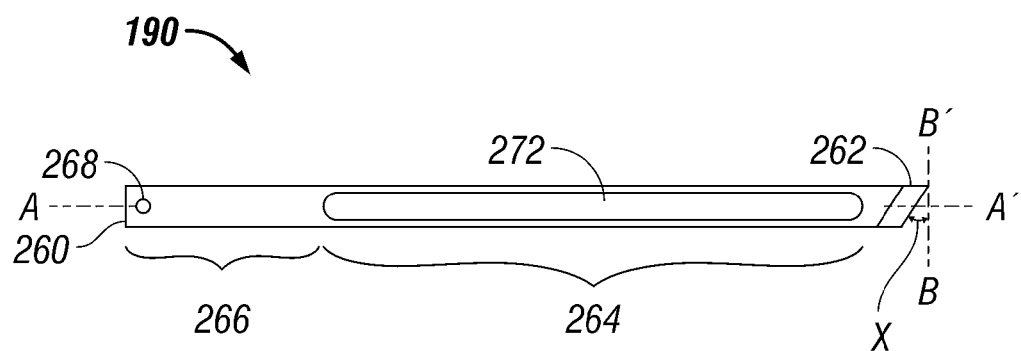
FIG. 15A is side view of a knife blade in accordance with the present disclosure.

Referring now to FIG. 15A, one embodiment of knife blade 190 is shown in accordance with the present disclosure having proximal end 260, distal end 262, web section 264, and knife rod attachment section 266. Rod attachment section 266 is compatible with an over-molding process for connecting the knife blade 190 to a blade rod (not shown in FIG. 15A). For example, aperture 268 defined in proximal end 260 is configured to fortify the over-molding process by providing a space where a mold will set when cured. Still referring to FIG. 15A, distal end 262 is shown having a slicing angle X. As mentioned above, it is envisioned that the slicing angle X of the tip of the knife blade 190 may be dimensioned to provide more or less aggressive cutting angles X depending upon a particular purpose. For example, where an aggressive cutting angle is desired, angle X may be about 10° to about 30° relative to vertical axis B-B'. In particular embodiments, a suitable slicing angle is about 15° relative to vertical axis B-B'. Also shown in FIG. 15A is slot 272 that is defined within the web section 264 to provide clearance for pin 139 (See FIG. 11) of the drive sleeve 134 (See FIG. 11) during reciprocation of the knife 190. In embodiments, web section 264 has a length of about 1.6 inches to about 2.1 inches and an aspect ratio greater than about 0.25. In other embodiments, blade 190 has a length of about 3.8 to about 4.5 inches along longitudinal axis A-A' defined therethrough. In still other embodiments, blade 190 also has a thickness of about 0.008-0.010 inches, and blade 190 has a height of about 0.100 inches.

Figure 15B:
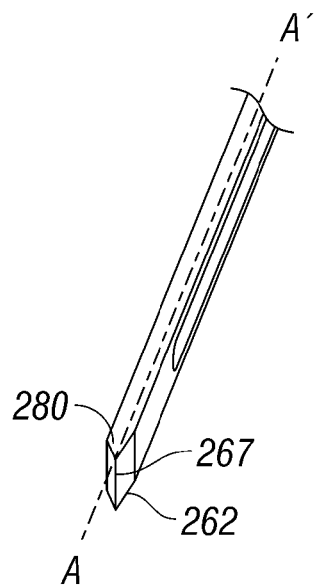
FIG. 15B is a front perspective view of the knife blade of FIG. 15A.

Referring now to FIG. 15B a front perspective view of blade 190 is shown. Distal end 262 is configured to generally converge to form a distal edge 267 having a grind angle, bevel or chamfer 280 shown between the outer portion of distal edge 267 and longitudinal axis A-A'. Suitable angles in accordance with the present disclosure include angles of about 10° to about 30° relative to the longitudinal central axis A-A'.

Blade 190 may be made of a variety of materials that provide high strength, and high flexibility. Furthermore, blade 190 may be made of razor blade stainless steel (4-40 or 4-20 stainless steel) with a thickness of about 0.008 inches to about 0.010 inches. The blade 190 may also be made of high carbon steel material such as A-2, O-1, D-2, and Damascus steel, high carbon stainless steel material such as ATS-34, BG-42, S3OV, 154CM, 420HC, and 440C. In particular embodiments, blade 190 may be made of surgical stainless steel material such as steels designated as 440-A and 440-B. Blade 190 may also be made of titanium, and ceramic materials such as zirconium oxide. It is further envisioned that knife blade 190 may be manufactured using a photo-chemical etching process with a machine ground cutting edge. Suitable materials for making blade 190 through this process, include any of the previously mentioned materials as well as aluminum, beryllium copper, brass, copper alloys, nickel silver, phosphorous bronze, stainless steel, steel, and combinations thereof.

Figure 16:
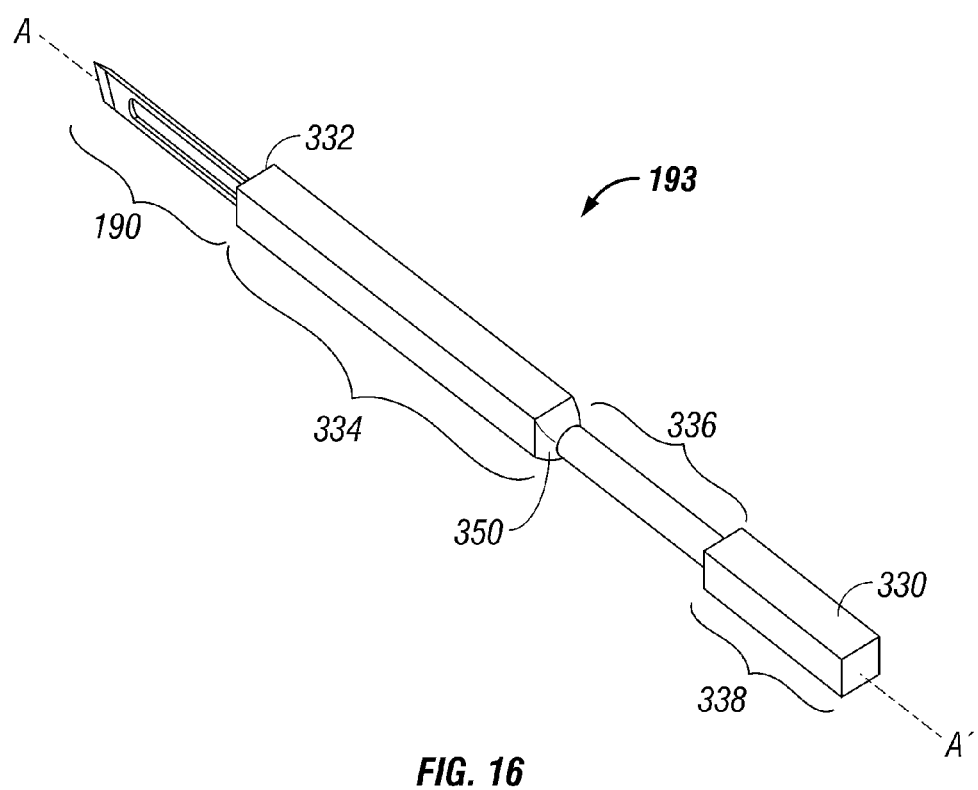
FIG. 16 is a rear perspective view of a knife rod in accordance with the present disclosure with a knife blade of FIG. 15A attached thereto.

As described above, knife rod 193 mounts to the proximal end 260 of knife 190 via one or more mechanically interfacing elements or affixed in any known manner in the art such as an over-molding process. Referring to FIG. 16, knife rod 193 is shown having a proximal end 330, distal end 332, first longitudinal section 334 containing distal end 332, second longitudinal section 338 containing proximal end 330, and third longitudinal section 336. Blade 190 is connected to the distal end 332 of the knife rod 193 (See FIG. 11).

Figure 17A:
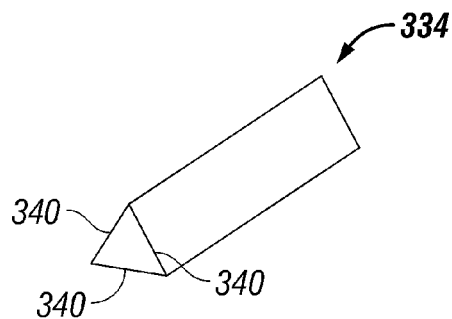
FIG. 17A is a front cross-sectional view of one possible first longitudinal section of the knife rod of FIG. 16.
Figure 17B:
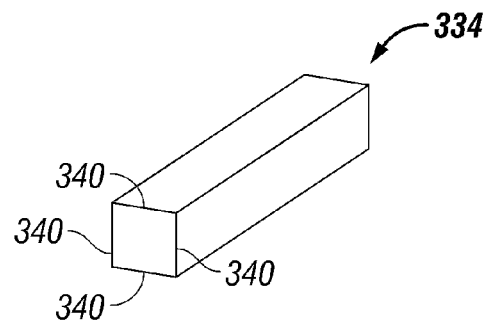
FIG. 17B is a front cross-sectional view of another envisioned first longitudinal section of the knife rod of FIG. 16.
Figure 17C:
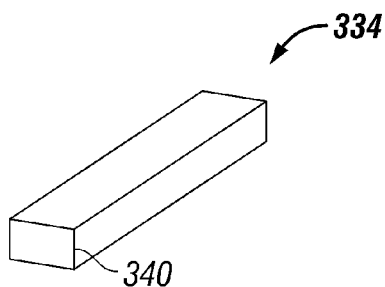
FIG. 17C is a front cross-sectional view of another envisioned first longitudinal section of the knife rod of FIG. 16.
Figure 17D:
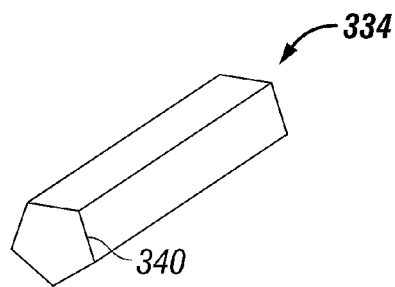
FIG. 17D is a front cross-sectional view of another envisioned first longitudinal section of the knife rod of FIG. 16.
Figure 17E:
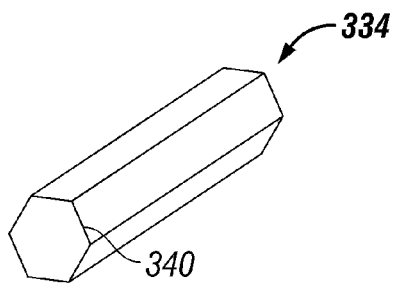
FIG. 17E is a front cross-sectional view of another envisioned first longitudinal section of the knife rod of FIG. 16.
Figure 17F:
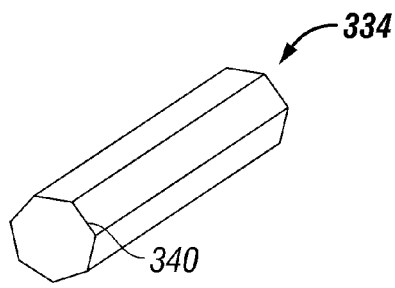
FIG. 17F is a front cross-sectional view of another envisioned first longitudinal section of the knife rod of FIG. 16.
Figure 17G:
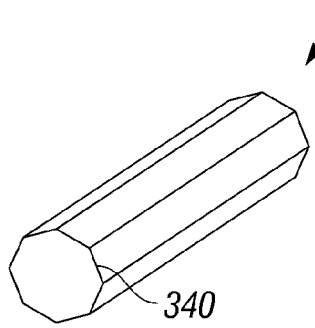
FIG. 17G is a front cross-sectional view of another envisioned first longitudinal section of the knife rod of FIG. 16.
Figure 17H:
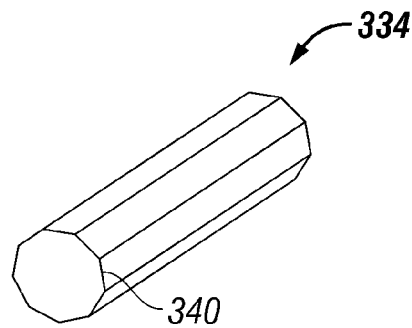
FIG. 17H is a front cross-sectional view of another envisioned first longitudinal section of the knife rod of FIG. 16.
Figure 17I:
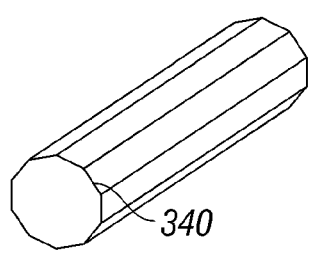
FIG. 17I is a front cross-sectional view of another envisioned first longitudinal section of the knife rod of FIG. 16.
Figure 17J:
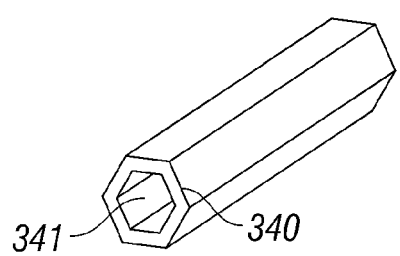
FIG. 17J is a front cross-sectional view of another envisioned first longitudinal section of the knife rod of FIG. 16.

First longitudinal section 334 includes a clocking feature to interact with the inner workings of the forceps and drive sleeve 134 (See FIG. 11) to ensure alignment of the knife rod 193 therein. As used herein, "clocking feature" refers to the ability of a rod to be aligned within a linked mechanism. Accordingly, the clocking feature enables the blade rod to mechanically interface on another component moving adjacent to the rod such that it rotates or moves in a similar direction. It is envisioned that the first longitudinal section 334 has a plurality of edges in order to provide a clock effect. For example, the first longitudinal section 334 has a predetermined cross-sectional shape and may further include a solid or hollow cross-sectional profile. Referring now to FIGS. 17(A-L) various envisioned front perspective cross-sectional views of the first longitudinal section 334 are shown having a plurality of edges 340. For example, FIG. 17A shows first longitudinal section 334 having a multi-sided cross-section having three edges 340. Moreover, FIG. 17A shows the first longitudinal section 334 having a cross-section with triangular dimensions. FIG. 17B shows the first longitudinal section 334 having a square cross-section with four peripheral edges 340. FIG. 17C shows the first longitudinal section 334 having a rectangular cross-section. FIG. 17D shows the first longitudinal section 334 having a pentagonal cross-section with five peripheral edges 340. FIG. 17E shows the first longitudinal section 334 having a hexagonal cross-section with six peripheral edges 340. FIG. 17F shows the first longitudinal section 334 having a heptagonal cross-section with seven peripheral edges 340. FIG. 17G shows the first longitudinal section 334 having an octagonal cross-section with eight peripheral edges 340. FIG. 17H shows the first longitudinal section 334 having a nonagonal cross-section with nine peripheral edges 340. FIG. 17I shows the first longitudinal section 334 having a decagonal cross-section with ten peripheral edges 340.

Figure 17K:
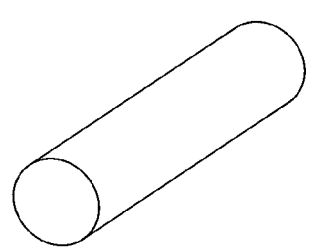
FIG. 17K is a front cross-sectional view of another envisioned first longitudinal section of the knife rod of FIG. 16.
Figure 17L:
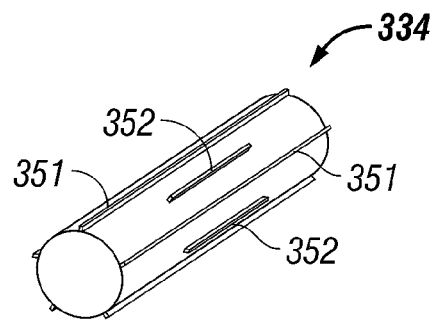
FIG. 17L is a front cross-sectional view of another envisioned first longitudinal section of the knife rod of FIG. 16.

As shown best in FIGS. 17A-17I, the first longitudinal section 334 or portion of the knife bar may have a solid symmetrical cross-sectional profile. Alternatively, as shown best in FIG. 17J it is envisioned that the first longitudinal section 334 has a hollow symmetrical cross-section, e.g., the cross-section may include one or more longitudinal voids 341. FIG. 17K shows the first longitudinal section 334 with a substantially round cross-section. The first longitudinal section 334 may include one or more flange 351 extending from the first longitudinal section to allow a substantially circular cross-section for clocking purposes. Flange 351 may extend along the length of first longitudinal section 334 and/or extend only a along a portion of the longitudinal length of the longitudinal section 334 such as flange 352. It is envisioned that the first longitudinal section 334 has a length of about 2 to about 5 inches along its longitudinal axis A-A'. First longitudinal section 334 may have a thickness of 0.7 inches to about 0.20 inches.

Figure 19:
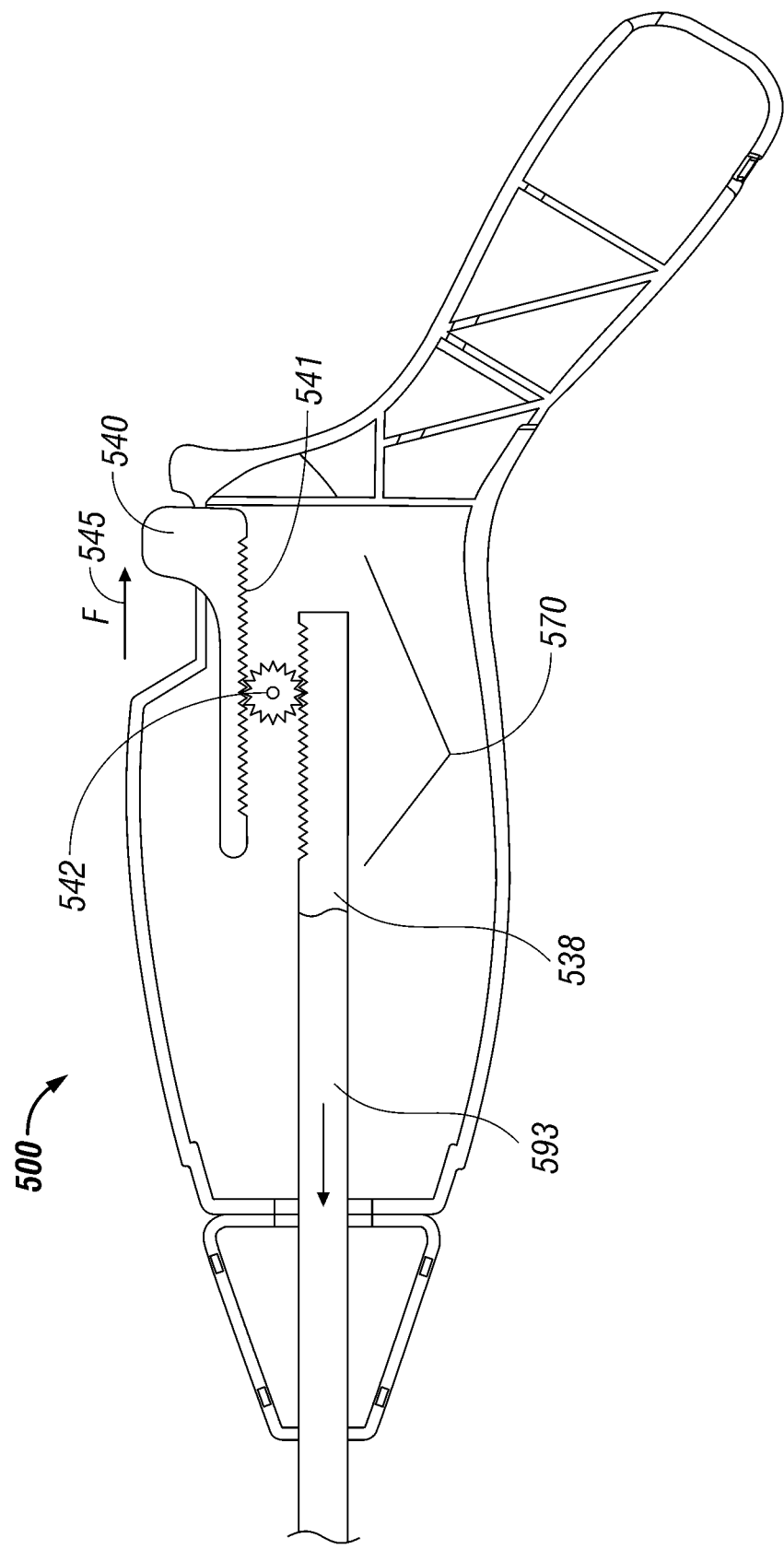
FIG. 19 is a schematic side view showing an alternative third knife activating mechanism in accordance with the present disclosure.
Figure 21:
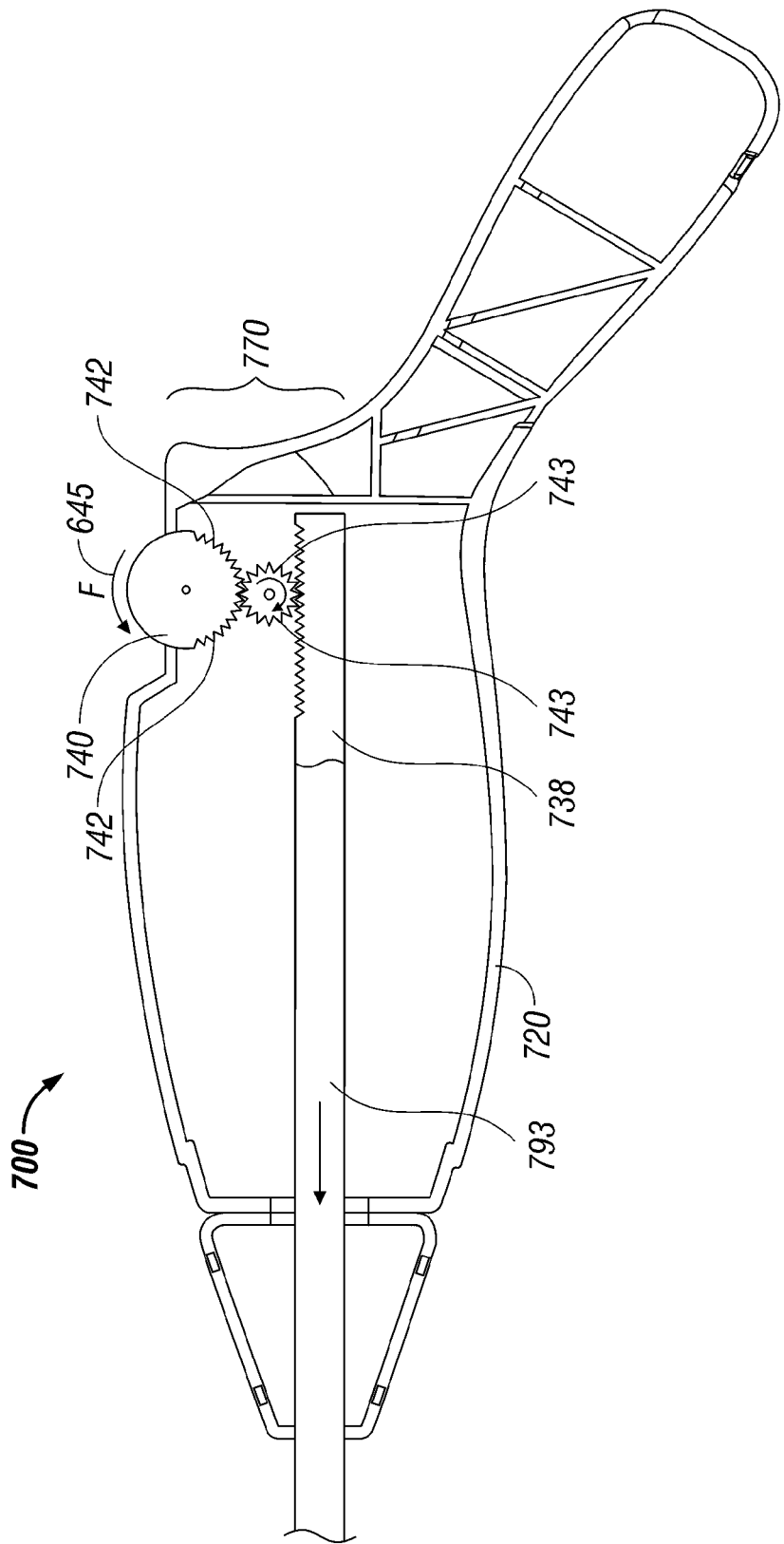
FIG. 21 is a schematic side view showing an alternative fifth knife activating mechanism in accordance with the present disclosure.

Referring back to FIG. 16, second longitudinal section 338 is made of a predetermined shape and material suitable for interaction with the inner working components of the forceps device 10. For example, as best seen in FIG. 19 and FIG. 21, the shape of the second longitudinal section may be suitable for interacting with gears such as toothed or pegged wheels meshed together to transmit motion and force from a finger activated assembly. For example, it is envisioned that the second longitudinal section is shaped to: form a connection in a bevel gear, form a portion of a gear such as a worm gear or a combination of a gear meshed with the thread, form a toothed rack for a rack and pinion set, or a single gear where a pinion meshes with the second longitudinal section to convert rotary motion to back and forth motion. It is also envisioned that the second longitudinal section may be an extension of the first longitudinal section with no variations in shape. The second longitudinal section 338 may have a length of about 1 inch to about 2 inches along its longitudinal axis A-A'. In embodiments, second longitudinal section may have a thickness of about 0.15 inches to about 0.5 inches and particularly 0.160 inches.

Referring to FIG. 16, the knife rod 193 may optionally include a third longitudinal section 336 having a substantially circular cross-section. The third longitudinal section 336 may be narrower than the first longitudinal section 334. A tapered portion 350 may also be included between to the first longitudinal section 334 and the third longitudinal section 336. It is envisioned that the third longitudinal section 336 has a length of about 1 inch to about 4 inches along the longitudinal axis A-A'. In particular embodiments, third longitudinal section may have a thickness of about 0.20-0.05 inches.

The inclusion of the trigger assembly described above may be problematic depending upon the particular manual dexterity of the user. For example depending upon the skill and/or preferences of some surgeons, some users may find increased manual dexterity when operating an alternative knife activating mechanism such as a thumb activator. Accordingly it is desirable to provide alternative knife activation mechanisms to the trigger assembly described above. Suitable alternatives to the trigger mechanism include various finger activating devices such as a thumb slide cutter with levers, thumb slide with rack and pinion, thumb wheel, thumb wheel with cutter levers, thumb wheel cutter with gears, and combinations of these mechanisms.

Figure 18:
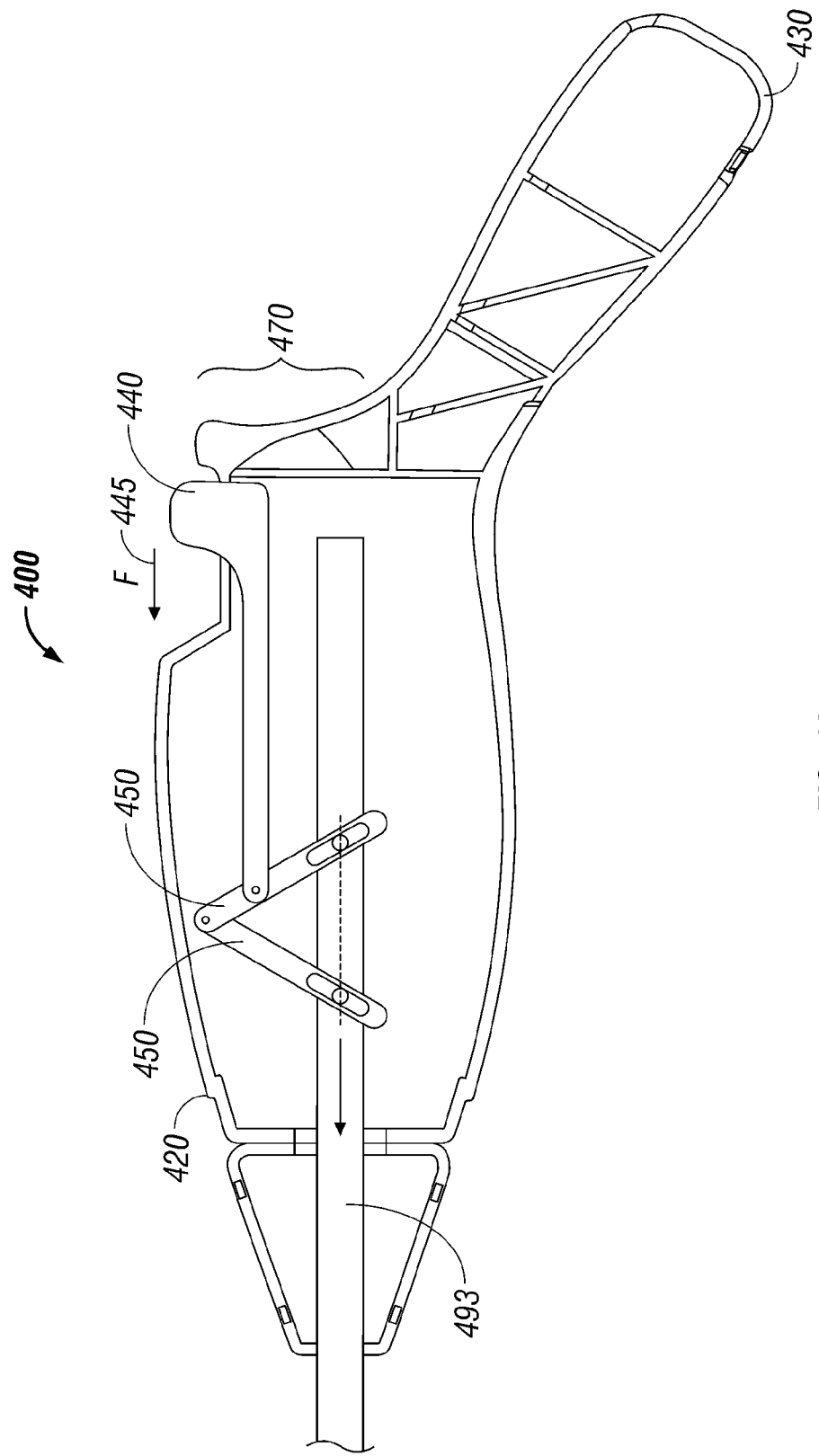
FIG. 18 is a schematic side view showing an alternative second knife activating mechanism in accordance with the present disclosure.

Turning now to FIG. 18, one embodiment of a bipolar forceps 400 is shown for use with various surgical procedures and generally includes a housing 420, a handle assembly 430, a knife activating assembly 470 suitable for operating end effector assembly 100 that cooperates to grasp, seal and divide large tubular vessels and large vascular tissues. Thumb lever 440 is shown connected to a series of levers 450 in communication with knife rod 493. When the user pushes distally on thumb lever 440 in the direction of arrow 445, the force is transferred through the lever 450 into knife rod 493. Consequently the knife rod 493 moves distally and actuates the knife (not shown in FIG. 18). Conversely, pulling proximally on the thumb lever 450 will pull on levers 450 and move knife rod 493 proximally, retracting the knife (not shown in FIG. 18). A spring (not shown) may also be provided that biases the knife in a proximal-most position.

Turning now to FIG. 19, another embodiment of a bipolar forceps 500 is shown having a knife activating assembly 570 suitable for operating end effector assembly 100. Thumb lever 540 is shown shaped with a rack surface 541 connected to a pinion 542 in communication with the second longitudinal rack surface 538 of knife rod 593. When the user pulls on thumb lever 540 in the direction of arrow 545, the force is transferred through the pinion 542 into the second longitudinal section 538 of knife rod 593. Consequently the knife rod 593 moves distally and actuates the knife (not shown in FIG. 19). Conversely, pushing on the thumb lever 540 will rotate piston 542 and move knife rod 593 in a proximal direction and retract the knife (not shown in FIG. 19). A spring (not shown) may also be provided that biases the knife in a proximal-most position.

Figure 20:
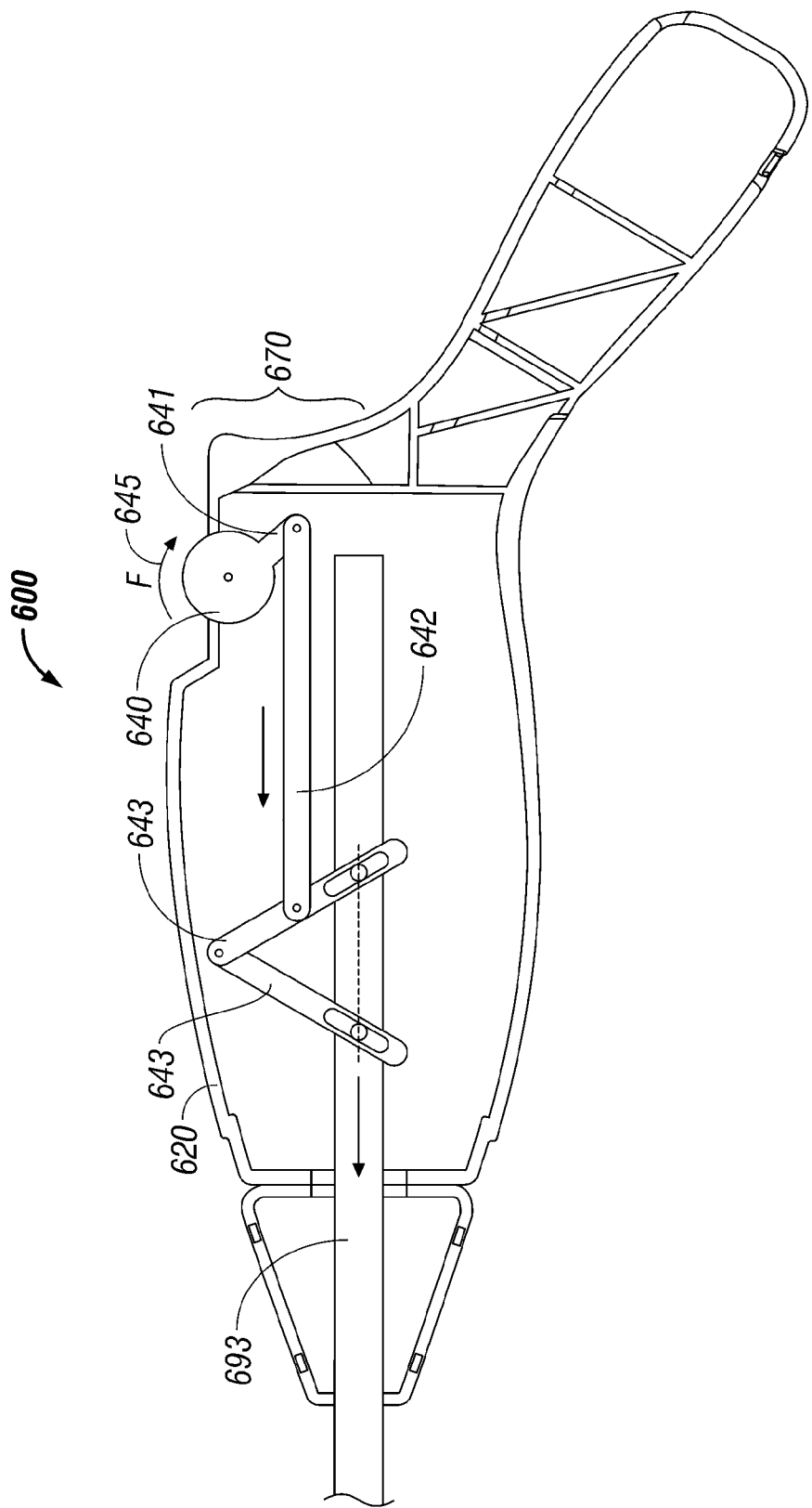
FIG. 20 is a schematic side view showing an alternative fourth knife activating mechanism in accordance with the present disclosure.

Turning now to FIG. 20, another embodiment of a bipolar forceps 600 is shown having a knife activating assembly 670 suitable for operating end effector assembly 100. Thumb wheel 640 is shown shaped with a flange 641 inside the housing 620. Flange 641 is connected to a rod 642 and a series of one or more levers 643 that are in communication with knife rod 693. When the user pulls on thumb wheel 640 in the direction of arrow 645, the force is transferred through flange 641, rod 642, levers 643 and knife rod 693. Consequently the knife rod 693 moves distally and actuates the knife (not shown in FIG. 19). Conversely, pushing the thumb wheel 650 distally will rotate flange 641 proximally and pull levers 643 and knife rod 693 in a proximal direction. Consequently, the knife rod 693 moves proximally and retracts the knife (not shown in FIG. 20).

FIG. 21 shows another embodiment of a bipolar forceps 700 is shown having a knife activating assembly 770 suitable for operating end effector assembly 100. Thumb wheel 740 is shown shaped with a circular rack 742 inside the housing 720. Rack 742 is connected to a gear 743 which is in turn connected to the second longitudinal rack section 738 of the knife bar 793. When the user moves thumb wheel 740 in the direction of arrow 645, the force is transferred through rack 742, gear 743, and knife rod 793. Consequently the knife rod 793 moves distally and actuates the knife (not shown in FIG. 19). Conversely, moving the thumb wheel 740 opposite arrow 645 will rotate gear 743 and pull knife rod 793 in a proximal direction, and retract the knife (not shown in FIG. 21).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A bipolar forceps, comprising:
   a housing;
   a shaft affixed to the housing having jaw members at a distal end thereof;
   a drive assembly that moves the jaw members relative to one another from a first position wherein the jaw members are disposed in spaced relation relative to one another to a second position wherein the jaw members are closer to one another for manipulating tissue;
   a movable handle rotatable about a pivot to force the drive assembly to move the jaw members between the first and second positions;
   a knife assembly having a movable knife rod that translates a knife blade between the jaw members when the jaw members are disposed in the second position; and
   a knife activating assembly in communication with the knife rod and configured to translate the knife blade upon actuation thereof, the knife activating assembly including first, second and third levers, the first lever actuatable by a user, the third lever in communication with the knife rod, and the second lever being the intermediary lever therebetween, wherein the second and third levers are pivotally coupled to the knife rod.

2. The forceps according to claim 1, wherein the first lever is a thumb lever.

3. The forceps according to claim 2, wherein a portion of the thumb lever is disposed exterior of the housing.

4. The forceps according to claim 2, wherein, when a force is applied to the thumb lever, the knife rod moves distally to actuate the knife blade.

5. The forceps according to claim 1, wherein the first lever is substantially parallel with respect to the knife rod.

6. The forceps according to claim 1, wherein the second and third levers form a substantially inverted V-shaped configuration.

7. The forceps according to claim 1, wherein a length of the second lever is equal to a length of the third lever.

8. The forceps according to claim 7, wherein a length of the first lever is greater than the lengths of the second and third levers.

* * * * *